United States Patent
Sabin et al.

(10) Patent No.: US 8,361,298 B2
(45) Date of Patent: Jan. 29, 2013

(54) MULTICHANNEL PREPARATIVE ELECTROPHORESIS SYSTEM

(75) Inventors: Douglas G. Sabin, Marblehead, MA (US); Todd J. Barbera, Marblehead, MA (US); Paul Chandler Sabin, Needham, MA (US); T. Christian Boles, Bedford, MA (US)

(73) Assignee: Sage Science, Inc., Beverly, MA (US)

( * ) Notice: Subject to any disclaimer, the term of this patent is extended or adjusted under 35 U.S.C. 154(b) by 657 days.

(21) Appl. No.: 12/576,148

(22) Filed: Oct. 8, 2009

(65) Prior Publication Data

US 2010/0126862 A1    May 27, 2010

Related U.S. Application Data

(60) Provisional application No. 61/195,566, filed on Oct. 8, 2008, provisional application No. 61/150,243, filed on Feb. 5, 2009.

(51) Int. Cl.
G01N 27/453    (2006.01)

(52) U.S. Cl. .......................... 204/600; 204/606; 204/627

(58) Field of Classification Search .............. 204/457, 204/627, 630, 606, 612, 618, 615, 600, 469; 422/99, 100, 681, 72, 63, 64, 502; 222/1
See application file for complete search history.

(56) References Cited

U.S. PATENT DOCUMENTS

| | | |
|---|---|---|
| 3,407,133 A | 10/1968 | Oliva et al. |
| 3,533,933 A | 10/1970 | Strauch |
| 3,616,454 A | 10/1971 | Levy et al. |
| 3,980,546 A | 9/1976 | Caccavo |
| 4,175,662 A | 11/1979 | Zold |
| 4,315,812 A | 2/1982 | Karlson |
| 4,375,401 A | 3/1983 | Catsimpoolas |
| 4,545,888 A | 10/1985 | Walsh |
| 4,608,147 A | 8/1986 | Clad |
| 4,655,898 A | 4/1987 | Poulhes et al. |
| 4,707,233 A | 11/1987 | Margolis |
| 4,708,782 A | 11/1987 | Andresen et al. |
| 4,835,263 A | 5/1989 | Nguyen et al. |
| 4,948,481 A | 8/1990 | Mullner |
| 5,062,942 A | 11/1991 | Kambara et al. |
| 5,169,511 A | 12/1992 | Allington et al. |
| 5,217,591 A | 6/1993 | Gombocz et al. |
| 5,384,022 A | 1/1995 | Rajasekaran |
| 5,433,837 A | 7/1995 | Brunk et al. |

(Continued)

FOREIGN PATENT DOCUMENTS

| | | |
|---|---|---|
| EP | 0334615 A2 | 9/1989 |
| EP | 0382426 A2 | 8/1990 |

(Continued)

OTHER PUBLICATIONS

Ansorge et al., "A simple field gradient technique which leads to sharpening of bands of DNA and to an increase in the number of receivable bases per gel", *J. of Biochem. Biophys. Meth.*, 10:237-243 (1984).

Boncinelli et al., "An agarose gel resolving a wide range of DNA fragment lengths", *Anal. Biochem.*, 134:40-43 (1983).

Chan et al., "DNA kinetics in microfabricated devices", *Micro Electro Mechanical Systems*, 60-63 (2002).

(Continued)

*Primary Examiner* — Alex Noguerola
*Assistant Examiner* — Gurpreet Kaur
(74) *Attorney, Agent, or Firm* — Mintz Levin Cohn Ferris Glovsky and Popeo, P.C.; Ivor R. Elrifi; Katherine J. Miller

(57) ABSTRACT

The invention provides an electrophoresis cassette, methods for making the electrophoresis cassette, and method of fractionating analytes from a sample based upon electrophoretic mobility in a single application of the sample to an electrophoretic system.

80 Claims, 46 Drawing Sheets

U.S. PATENT DOCUMENTS

| | | | |
|---|---|---|---|
| 5,443,704 A | 8/1995 | Kirkpatrick et al. | |
| 5,538,614 A | 7/1996 | Han | |
| 5,717,602 A | 2/1998 | Kenning | |
| 5,800,690 A | 9/1998 | Chow et al. | |
| 5,801,115 A | 9/1998 | Albers et al. | |
| 5,827,418 A | 10/1998 | Haven et al. | |
| 5,840,169 A | 11/1998 | Andersen | |
| 6,290,831 B1 | 9/2001 | Liran et al. | |
| 6,344,325 B1 | 2/2002 | Quake et al. | |
| 6,366,924 B1 | 4/2002 | Parce | |
| 6,369,893 B1 | 4/2002 | Christel et al. | |
| 6,388,746 B1 | 5/2002 | Eriksson et al. | |
| 6,430,512 B1 | 8/2002 | Gallagher | |
| 6,611,768 B2 | 8/2003 | Gallagher | |
| 6,808,609 B1 | 10/2004 | Soane et al. | |
| 6,834,240 B2 | 12/2004 | Gallagher | |
| 6,867,851 B2 | 3/2005 | Blumenfeld et al. | |
| 6,919,571 B2 | 7/2005 | Lai et al. | |
| 6,964,736 B2 | 11/2005 | Quake et al. | |
| 7,056,746 B2 | 6/2006 | Seul et al. | |
| 7,108,775 B2 | 9/2006 | Bahatt et al. | |
| 7,122,104 B2 | 10/2006 | Cabilly et al. | |
| 7,413,642 B2 | 8/2008 | Hassard et al. | |
| 7,419,784 B2 | 9/2008 | Dubrow et al. | |
| 2002/0187503 A1 | 12/2002 | Harrold et al. | |
| 2003/0151735 A1 | 8/2003 | Blumenfeld et al. | |
| 2003/0170609 A1 | 9/2003 | Rigler | |
| 2004/0011650 A1 | 1/2004 | Zenhausern et al. | |
| 2004/0089546 A1 | 5/2004 | Bahatt et al. | |
| 2005/0205427 A1 | 9/2005 | Boschetti et al. | |
| 2006/0193752 A1 | 8/2006 | Levine | |
| 2007/0284250 A1 | 12/2007 | Magnant et al. | |
| 2007/0286773 A1 | 12/2007 | Schlautmann et al. | |
| 2008/0057557 A1 | 3/2008 | Margalit | |

FOREIGN PATENT DOCUMENTS

| | | |
|---|---|---|
| EP | 1384067 A2 | 1/2004 |
| WO | WO-96/23213 A1 | 8/1996 |
| WO | WO-02/44706 A1 | 6/2002 |
| WO | WO-2005/093388 A1 | 10/2005 |
| WO | WO-2006/031385 A2 | 3/2006 |

OTHER PUBLICATIONS

Chen et al., "An inexpensive microslab gel DNA electrophoresis system with real-time flourescence detection", *Electrophroresis*, 27(2):387-393 (2005).

Costa et al., "Isolation of proteins and nucleic acids by electrophoresis on disposable gel columns", *Electrophoresis*, 17(4):781-783 (1995).

DNA Analysis, The Development of a Portable High-Speed DNA Analysis Device—Paving The Way Towards Point-Of-Care Diagnosis and Advanced Medical Treatment, http://www.azonano.com/Details.asp?ArticleID=1783 (2006).

Girvitz et al., "A rapid and efficient procedure for the purification of DNA from agarose gels", *Analytical Biochemistry*, 106(2):492-496 (1980).

Heller et al., "Microelectrophroresis for the separation of DNA fragments", *Electrophoresis*, 13(1):512-520 (1992).

Inoue et al., "I-shaped microchannel array chip for parallel electrophoretic analyses", *Analytical Chemistry*, 79:2168-2173 (2007).

Johnson et al., "Sizing of DNA fragments by flow cytometry", *Proc. SPIE*, 1895:69-78 (1993).

Kaabouch et al., "An analysis system for DNA gel electrophroresis images based on automatic thresholding and enhancement", *Electro/Information Technology, 2007 IEEE international Conference* on May 17-20, 2007, pp. 26-31.

Khandurina et al., "Micropreparative Fraction Collection in Microfluidic Devices", *Anal. Chem.*, 74(7):1737-1740 (2002).

Kumar et al., "Pyrrolidine Nucleic Acids: DNA/PNA Oligomers with 2-Hydroxy/Aminomethyl-4(thymin-1-yl)pyrrolidine-N-acetic acid", *Organic Letters*, 3(9):1269-1272 (2001).

Lagriffoul et al., "The Synthesis, Co-Oligomerization and Hybridization of a Thymine-Thymine Heterodimer Containing PNA", *Bioorganic and Medical Chemistry Letters*, 4:1081-1082 (1994).

Li et al., "Design of a PMMA Chip for Selective Extraction of Size-Fractioned DNA", *Proceedings of the 1st IEEE International Conference on Nano/Micro Engineered and Molecular Systems*, Zhuhai China, Jan. 18-21, 2006.

Li et al., "Design, simulation and optimization of a miniturized device for size-fractioned DNA extraction", *Electrophoresis*, 28(24):4661-4667 (2007).

Lin et al., "Addressable electric fields for size-fractioned sample extraction in microfluidic devices", *Anal. Chem.*, 77(14):4338-4347 (2005).

Lin et al., "Selective extraction of size-fractioned DNA samples in microfabricated electrophroresis devices", *Journal of Chromatography*, 1010(2):255-268 (2003).

Liu et al., "DNA fragment analysis by an affordable multiple-channel capillary electrophoresis system", *Electrophoresis*, 24(1-2):93-95 (2003).

Lundqvist et al., "Electrophoretic separation and confocal laser-induced fluorescence detection at ultralow concentrations in constricted fused-silica capillaries", *Electrophoresis*, 24(11):1737-1744 (2003).

Marshall et al., "Analytical micro-preparative electrophroresis: Quatitation of phosphoglucose isomerase isoenzymes", *Anal. Biochem.*, 91(1):283-292 (1978).

Minalla et al., "Automated DNA fraction collection on glass microchips", *Micro Total Analysis Systems*, 2:946-948 (2002).

Perkin Elmer, "ABI PRISM 377: DNA Sequencer", *User Manual*, Part No. 903433, Rev. A, (Jan. 1995).

Peterson et al., "Synthesis and oligomerization of Nδ-Boc-Nα-(thymin-1-ylacetyl)ornithine", *Bioorganic and Medical Chemistry Letters*, 6:793-796 (1996).

Petty et al., "Characterization of DNA size determination of small fragments by flow cytometry", *Anal. Chem.*, 67:1755 (1995).

Rampino et al., "Apparatus for gel electrophoresis with continuous monitoring of individual DNA molecules by video epifluorescence microscopy", *Anal. Biochem.*, 194(2):278-283 (1991).

Sun et al., "Electrophroretic chip for high-fidelity fractionation of double-stranded DNA", *Electrophroresis*, 28(10):1572-1578 (2007).

Sutherland et al., "Electronic imaging system for direct and rapid quantation of fluorescence from electrophoretic gels: application to ethidium bromide-stained DNA", *Anal. Biochem.*, 163(2):446-457 (1987).

Tabak et al., "A method for the recovery of DNA from agarose gels", *Nucleic Acids Research*, 5(7):2321-2332 (1978).

Wang et al., "A simple microfluidic system for efficient capillary electrophoresis separation and sensitive fluorimetric detection of DNA fragments using light-emitting diode and liquid-core waveguide techniques", *Electrophoresis*, 26(19):3602-3608 (2005).

Xiao et al., "CE with LED-based detection: An update", 30(1):189-202 (2008).

Zakharov et al., "Recovery of SDS-protein and DNA using commercial automated gel electrophoresis apparatus", *Appl. Theor. Electrophor.*, 5(1):25-29 (1995).

Zalewski et al., "Elctrokinectic sorting and collection of fractions for preparative capillary electrophrosis on a chip", *Lab on a Chip*, 8:801-809 (2008).

Inoue et al. "I-shaped microchannel array chip for parallel electrophoretic analyses." Analytical Chemistry, American Chemical Society, US. vol. 79, No. 5, pp. 2168-2173. Mar. 5, 2007.

Li et al. "Design, simulation, and optimization of a miniaturized device for size-fractioned DNA extraction." Electrophoresis, vol. 28, No. 24, pp. 4661-4667. Dec. 2007.

Lin et al. "Selective extraction of size-fractionated DNA samples in microfabricated electrophoresis devices." Journal of Chromatography, Elsevier Science Publishers B.V., NL. vol. 1010, No. 2, pp. 255-268. Aug. 29, 2003.

Zalewski et al. "Electrophoretic sorting and collection of fractions for preparative capillary electrophoresis on a chip." Lab on a Chip Royal Society of Chemistry UK, vol. 8, No. 5, pp. 801-809. May 2008.

SHAPE OF CONSTRICTION BY CROSS-SECTIONAL VIEW:

EDGE CHARACTERISICS OF A CONSTRICTION:

| ORIFICES AND THEIR NOMINAL COEFFICIENTS | | | | |
|---|---|---|---|---|
| | SHARP EDGED | ROUNDED | SHORT TUBE | BORDA |
| | | | | |
| $C$ | 0.61 | 0.98 | 0.80 | 0.51 |
| $C_c$ | 0.62 | 1.00 | 1.00 | 0.52 |
| $C_v$ | 0.98 | 0.98 | 0.80 | 0.98 |

MULTICHANNEL PREPARATIVE ELECTROPHORESIS SYSTEM

RELATED APPLICATIONS

This application is related to provisional application U.S. Ser. No. 61/195,566, filed Oct. 8, 2008, as well as to the provisional application U.S. Ser. No. 61/150,243, filed Feb. 5, 2009, the contents of which are each herein incorporated by reference in their entirety.

FIELD OF THE INVENTION

This invention relates generally to the field of molecular biology. Systems and methods of the invention are used to prepare and analyze DNA, RNA, and proteins from biological samples.

BACKGROUND OF THE INVENTION

Electrophoretic separation of DNA fragments is used for a number of purposes in molecular and clinical biology and medicine, including next generation DNA Sequencing, medical diagnostics, forensic science and DNA computing.

Preparative gel electrophoresis of DNA has good resolution, adequate capacity and ease of use on a small scale. However, the manual process is both time and labor intensive. Critically, it is difficult to remove the desired DNA fraction from the gel. This removal process routinely entails excising a band or portion from the gel containing the DNA of interest and then extracting it by a variety of chemical and physical means including the use of enzymes, centrifugation, freezing and more. Importantly, these methods substantially reduce the amount of DNA harvested and dilute the resultant DNA into large volumes of fluid, therefore, requiring additional time and expense to re-concentrate it into a smaller, usable, aliquot. This problem is so significant to the field of molecular biology, in fact, that the removal of DNA from gels in small volumes of fluid has spawned a separate industry for making various types of kits, reagents and devices to accomplish the task. However, despite a demonstrated need and the efforts of skilled artisans, a solution has not yet been developed.

SUMMARY OF THE INVENTION

The invention provides compositions including electrophorsis cassettes and preparative electrophoresis systems as well as methods of fractionating analytes from a sample. Electrophoresis cassettes and preparative electrophoresis systems of the invention fractionate nucleic acids or polypeptides of a specified or desired molecular weight or electrophoretic mobility from a biological sample, and subsequently extract the desired nucleic acids or polypeptides from the gel matrix or buffer compositions by drawing them across an analyte and ion permeable barrier and into an elution chamber.

Specifically, the invention provides an electrophoresis cassette containing a plate including at least one macrofluidic separation channel, the channel having a first physically and electrically isolated portion and a second physically and electrically isolated portion; and an elution chamber positioned on one or another of the physically and electrically isolated portions, the chamber comprising at least one an elution cavity and an analyte-impermeable barrier. The elution chamber is attached or removable. For instance, the elution chamber is generated by inserting an elution chamber insert into an elution chamber cavity within the first or second physically and electrically separated portion of the separation channel, inserting a liquid gel matrix composition into the separation channel, solidifying the gel matrix composition, removing the elution chamber insert thereby generating an elution chamber, placing an analyte-impermeable barrier on the distal side of the elution chamber, and filling the elution chamber with an elution buffer composition. The term "solidifying" is meant to describe a process by which either a liquid matrix organizes into a solid gel form (which may be temperature-dependent), or alternatively, a process by which liquid matrix components polymerize to form a solid gel. Regardless of the gel matrix composition used, the composition is injected as a liquid, and subsequently transforms into a solid once inside the cassette.

Alternatively, or in addition, an elution chamber of the above electrophoresis cassette further include at least one of an analyte-permeable barrier, a sample collection chamber including a sample removal port, and an analyte-impermeable barrier.

Furthermore, the elution chamber is removable. In certain embodiments of the elution chamber, the chamber contains, in the direction of electrophoresis, a first removable side, an analyte-permeable membrane, a sample collection chamber, an analyte-impermeable membrane, and a second removable side. The removable sides are removable portions of the sample collection chamber with at least one of an opening, protrusion, or recession for binding either the analyte-permeable or analyte-impermeable membrane to the sample collection chamber. Alternatively, the removable sides are O-rings that fit within a first and second side of the sample collection chamber and bind either the analyte-permeable or analyte-impermeable membrane to the sample collection chamber. A removable elution chamber is also used as an elution chamber insert, as described above. The removable elution chamber is attached to the elution chamber cavity within the first or second physically and electrically isolated portion of the separation channel.

The analyte-permeable barrier of the elution chamber is a hydrophilic membrane or filter. In certain embodiments, the analyte-permeable barrier includes a least one pore having a diameter range of between 0.4 micron to 50 microns, and preferably, of between 0.4 micron to 1 micron.

The analyte-impermeable barrier of the elution chamber is a membrane, filter, film, or any combination thereof. Preferably, the analyte-impermeable barrier is an ultrafiltration membrane or a conductive film. In certain embodiments, the ultrafiltration membrane contains a least one pore having a diameter range of between 0.001 micron to 0.1 micron. Alternatively, or in addition, the ultrafiltration membrane has a molecular weight cutoff of between 1,000 to 30,000 daltons. Preferably, the ultrafiltration membrane has a molecular weight cutoff of between 3,000 to 10,000 daltons. In other embodiments, the analyte-impermeable barrier includes a conductive film having the same charge as the analyte or a conductive film contacted with negatively-charged sulfate groups. In certain aspects, the analyte-impermeable barrier is Nafion.

The electrophoresis cassette also includes a constriction point provided between the separation channel and at least one of the first and second physically and electrically isolated portions.

In certain embodiments of the cassette, at least one macrofluidic separation channel is tapered from one end to the constriction point. Alternatively, or in addition, at least one macrofluidic separation channel is optically-transparent. In other embodiments, the separation channel is optically-transparent on at least one side, on only one side, or on only a portion of one side. For instance, the separation channel is optically-transparent on the bottom side, the top side, or both bottom and top sides. Preferably, optical transparency is maintained along the separation channel from the distal edge of the sample well cavity to the division point.

The electrophoresis cassette contains between 1 and 5 macrofluidic separation channels. Alternatively, the cassette contains between 1 and 9 or between 1 and 13 macrofluidic separation channels. The maximum number of macrofluidic separation channels contained in the electrophoresis cassette is determined by the ability of a detection system to read the cassette, and in theory, no maximum number exists, however, a practical range of is between 25-33 macrofluidic channels.

The electrophoresis cassette also contains a buffer reservoir for each of the macrofluidic separation channels.

The electrophoresis cassette includes a cover for the plate. In one aspect, the cover includes a configuration that corresponds to the configuration of the top of the plate. In another aspect, the cover includes at least one of an opening, a protrusion and a recess that align with at least one of the buffer reservoirs. Alternatively, or in addition, the cover includes at least one of an opening, a protrusion and a recess that align with at least one of the macrofluidic channel, the buffer reservoir, the sample well cavity, the sample removal port, the elution reservoir, the waste reservoir, and the first and second physically and electrically isolated portions.

Moreover, the electrophoresis cassette contains at least one of a sample well cavity, an elution reservoir and a waste reservoir. In certain embodiments of the invention, the elution reservoir and the waste reservoir are provided at an end of the first physically and electrically isolated portions and the second physically and electrically isolated portions, respectively.

The electrophoresis cassette further includes a division point provided between the macrofluidic channel and the elution reservoir and the waste reservoir. In certain embodiments of the cassette, the constriction point is the division point.

The macrofluidic channel of the electrophoresis cassette includes at least one of a gel matrix composition, a liquid buffer composition, a solid buffer composition. In aspects, at least one of a gel matrix composition, a liquid buffer composition, a solid buffer composition contains at least one of a fluorophore or a chromophore. The fluorophore is either the analyte or is bound to the analyte. Similarly, the chromophore is either the analyte or is bound to the analyte. An exemplary fluorophore is ethidium bromide, which binds to polynucleic acids and allows detection of the polynucleic acid analyte. Moreover, a polypeptide analyte is a chromophore because it can be detected by mere absorption of ultraviolet light.

At least one macrofluidic separation channel of the electrophoresis cassette contains a gel matrix composition. In one aspect, the gel matrix composition fills a volume of the macrofluidic separation channel, including at least one of the first and second physically and electrically isolated portions. In another aspect, the gel matrix composition defines at least one sample well within at least one sample well cavity.

The macrofluidic separation channel further contains a lens positioned between the sample well cavity and the division point. The lens includes a gel matrix composition. In certain embodiments, the gel matrix composition of the lens contains a higher concentration of a polymer, thereby making the lens denser. The lens takes any shape, including a curve that follows the direction of electrophoresis. Functionally, the lens focuses at least one of an analyte. The lens is positioned proximal or distal to a constriction point or to a detection zone within the separation channel.

Furthermore, at least one macrofluidic channel of the electrophoresis cassette contains a buffer composition. In one aspect, the buffer composition fills a volume of at least one buffer reservoir, at least one sample well, at least one elution reservoir, and at least one waste reservoir.

At least one elution chamber of the electrophoresis cassette contains an elution buffer composition. In one aspect, the elution buffer composition fills a volume of at least one elution chamber.

The electrophoresis cassette of the invention is meant to be compatible with a variety of detection systems. As such, certain embodiments of the cassette contain an integrated electrode array. In this aspect, the cassette contains: a negative electrode positioned between the buffer reservoir and a corresponding end of the separation channel; a positive electrode positioned between an end of the first physically and electrically isolated portion and the elution reservoir; and a positive electrode positioned between an end of the second physically and electrically isolated portion and the waste reservoir.

The electrophoresis cassette further includes a removable seal. Non-limiting examples of seal materials are polymers, adhesive films, and tapes. The seal encloses at least one of an opening, a protrusion and a recess of the cover. Alternatively, or in addition, the seal encloses the entirety of the electrophoresis cassette. Functionally, the seal prevents spillage and evaporation of the buffer and gel matrix compositions contained within the cassette during storage. Moreover, the seal prevents the buffer and gel matrix compositions contained within the cassette from contacting or corroding the electrode array during storage.

Regardless of the features present within the electrophoresis cassette, the cassette is disposable.

The invention also provides a method of making an electrophoresis cassette, including: providing the above electrophoresis cassette, wherein the cassette further contains at least one of a buffer reservoir insert, a sample well insert, and a waste reservoir insert, and a cover, wherein the buffer reservoir insert includes a vent, wherein the buffer reservoir insert traverses an opening in the cover plate aligned with the buffer reservoir, wherein the sample well insert traverses an opening in the cover plate aligned with the sample well cavity, wherein the waste reservoir insert includes an injection port, and wherein the waste reservoir insert traverses an opening in the cover plate aligned with the waste reservoir; inserting a gel matrix composition through the injection port; solidifying the gel matrix composition, wherein the gel matrix composition transforms from a liquid to a solid; removing the buffer reservoir insert, sample well insert, and waste reservoir insert, wherein a buffer reservoir, a sample well, an elution reservoir, and a waste reservoir are generated; filling the buffer reservoir, the elution reservoir, and the waste reservoir with a buffer composition; filling the elution chamber with an elution buffer composition; and sealing the electrophoresis cassette.

In one aspect the above method further includes the steps of: providing a casting fixture, wherein the fixture includes a front plate that contacts the top of the cassette, wherein the front plate contains at least one opening that aligns with at least one of the vent of the buffer reservoir insert and the separation channel, and a back plate that contacts the bottom of the cassette, wherein the back plate contains at least one opening; attaching the casting fixture to electrophoresis cassette, wherein the back plate contacts the bottom of the electrophoresis cassette and the front plate contacts the top of the electrophoresis cassette, and wherein the back and front plates are attached to each other; wherein the casting fixture is provided and attached prior to the injecting step and, detaching the casting fixture from the electrophoresis cassette prior to the removing step.

According to this method, the buffer reservoir insert fills a volume of the buffer reservoir. Moreover, the sample well insert fills a volume of the sample well cavity. Furthermore, the waste reservoir insert fills a volume of the waste reservoir.

In one aspect of this method the casting fixture is horizontal or vertical during the inserting and solidifying steps.

The cassette provided for this method contains between 1 and 5 macrofluidic separation channels. Alternatively, the cassette contains between 1 and 9 or between 1 and 13 macrofluidic separation channels.

The invention also provides a detection system for detecting a property of an analyte within a sample including: the above-described electrophoresis cassette; an electrode array comprising at least one of a negative electrode and a positive electrode, wherein the negative electrode aligns with a position on the cassette between the buffer reservoir and a corresponding end of the separation channel, and wherein the positive electrode aligns with a physically and electrically isolated portion of the separation channel; a detector positioned near the separation channel of the electrophoresis cassette, wherein the detector detects a property of an analyte; a processor configured to activate or deactivate power to at least one positive electrode based upon a signal received from the detector; and a power module comprising at least one of a power supply and a relay to provide power to at least one of the processor, the negative electrode and at least one positive electrode.

In certain embodiments of this system, the detected property is an optical property of an analyte. Exemplary optical properties include, but are not limited to, the emission or absorption of light. Furthermore, the detected property includes magnetism, radiation, temperature, color, energy, or changes in any of the above.

The sample of this system contains a detectable label, such as a magnetic, paramagnetic, radioactive, enzymatic, immunological, or optical label. Non-limiting examples of optical labels are fluorescent and light-absorbing compounds. In one aspect, the sample contains a fluorescent compound and the analyte forms a complex with the fluorescent compound. In another aspect, the fluorescent compound or the analyte is a fluorophore. In another embodiment, the sample comprises a light-absorbing compound and the analyte forms a complex with the light-absorbing compound. Alternatively, the light-absorbing compound or the analyte is a chromophore.

The analyte of this system is a sample or a molecular weight marker.

In a preferred embodiment of this system, the detector detects a property of the molecular weight marker within a first macrofluidic channel and sends a signal to the processor. Subsequently, the processor receives the signal from the detector and applies an algorithm to determine the molecular weight of at least one of an analyte at the division point of a second macrofluidic channel.

The invention provides a method of fractionating analytes within a sample, including: providing an electrophoresis cassette described herein, wherein the cassette further comprises at least one of a buffer reservoir insert, a sample well insert, and a waste reservoir insert, and a cover, wherein the buffer reservoir insert includes a vent, wherein the buffer reservoir insert traverses an opening in the cover plate aligned with the buffer reservoir, wherein the sample well insert traverses an opening in the cover plate aligned with the sample well cavity, wherein the waste reservoir insert includes an injection port, and wherein the waste reservoir insert traverses an opening in the cover plate aligned with the waste reservoir; inserting a gel matrix composition through the injection port; solidifying the gel matrix composition, wherein the gel matrix composition transforms from a liquid to a solid; removing the buffer reservoir insert, sample well insert, and waste reservoir insert, wherein a buffer reservoir, a sample well, an elution reservoir, and a waste reservoir are generated; filling the buffer reservoir, an elution reservoir, and a waste reservoir with a buffer composition; filling the elution chamber with an elution buffer composition; and inserting the electrophoresis cassette into a detection system described herein; programming the processor of the detection system to selectively activate the positive electrode of the electrode array aligned with the physically and electrically isolated portion of the separation channel comprising the elution chamber when the processor determines that at least one of an analyte of the desired molecular weight is traversing the division point of the separation channel; applying the sample to the sample well; applying a voltage across the electrophoresis cassette; collecting analytes of the sample having a desired electrophoretic mobility in the elution chamber, thereby fractionating analytes within a sample.

This method further includes the steps of: providing a casting fixture, wherein the fixture includes a front plate that contacts the top of the cassette, wherein the front plate comprises at least one opening that aligns with at least one of the vent of the buffer reservoir insert and the separation channel, and a back plate that contacts the bottom of the cassette, wherein the back plate comprises at least one opening; attaching the casting fixture to electrophoresis cassette, wherein the back plate contacts the bottom of the electrophoresis cassette and the front plate contacts the top of the electrophoresis cassette, and wherein the back and front plates are attached to each other; wherein the casting fixture is provided and attached prior to the injecting step and, detaching the casting fixture from the electrophoresis cassette prior to the removing step.

In one aspect of this method, the sample contains a molecular weight marker. In another aspect of this method, the analyte is a polynucleic acid or a polypeptide. Moreover, the polynucleic acid contains deoxyribonucleic acid (DNA) or ribonucleic acid (RNA). Alternatively, or in addition, the polynucleic acid is double or single stranded. In certain aspects, the polypeptide is native or denatured.

In one aspect of this method, the sample contains at detectable compound. Exemplary detectable compounds are magnetically-, paramagnetically-, radioactively-, enzymatically-, immunologically-, or optically-detectable. Optically-detectable compounds are, for example, fluorescent and light-absorbing compounds. In certain embodiments, the sample contains at least one of a complex of an analyte and a fluorescent compound. In one aspect, the fluorescent compound is a fluorophore. In another aspect, the analyte is a fluorescent compound or fluorophore. Alternatively, or in addition, the sample contains at least one of a complex of an analyte and a light-absorbing compound. In one embodiment, the light-absorbing compound is a chromophore. In another embodiment, the analyte is a light-absorbing compound or chromophore.

According to this method, at least one of the gel matrix composition, the buffer composition, or the elution buffer composition comprises at least one of a fluorophore that complexes to at least one of an analyte. Moreover, at least one of the gel matrix composition, the buffer composition, or the elution buffer composition comprises at least one of a chromophore that complexes to at least one of an analyte.

According to this method, the processor of the detection system selectively activates the positive electrode of the electrode array aligned with the physically and electrically isolated portion of the separation channel comprising the elution chamber when an analyte having a specified electrophoretic mobility is detected and wherein the specified electrophoretic mobility is distinct for each macrofluidic channel.

The invention provides a composition containing an electrophoresis cassette, the electrophoresis cassette including: (a) a channel plate including a macrofluidic channel, wherein the macrofluidic channel comprises, from proximal to distal, a buffer reservoir, a first end of a separation channel, a sample well cavity, a constriction point, a division point, an elution chamber cavity, a second physically and electrically isolated end of the separation channel, a third physically and electrically isolated end of the separation channel, an elution reservoir, and a waste reservoir; (b) an elution chamber including, from proximal to distal, an analyte-permeable barrier, a sample collection chamber having a sample removal port, and an analyte-impermeable barrier, wherein the elution module is attached to the elution chamber cavity; (c) a cover plate that contacts the top of the channel plate, wherein the cover plate contains at least one of an opening, a protrusion, and a recess that align, from proximal to distal, with the buffer reservoir, the sample well cavity, the elution chamber, a combination of the second physically and electrically isolated end of the separation channel and the elution reservoir, and a combination of the third physically and electrically isolated end of the separation channel and the waste reservoir; (d) a gel matrix composition that fills the macrofluidic separation channel and defines a sample well within the sample well cavity; (e) a liquid buffer composition that fills the buffer reservoir, the sample well, the elution reservoir, and the waste reservoir; (f) an elution buffer composition that fills the elution chamber; and (g) a seal that encloses the electrophoresis cassette.

DETAILED DESCRIPTION

Figure 1A:
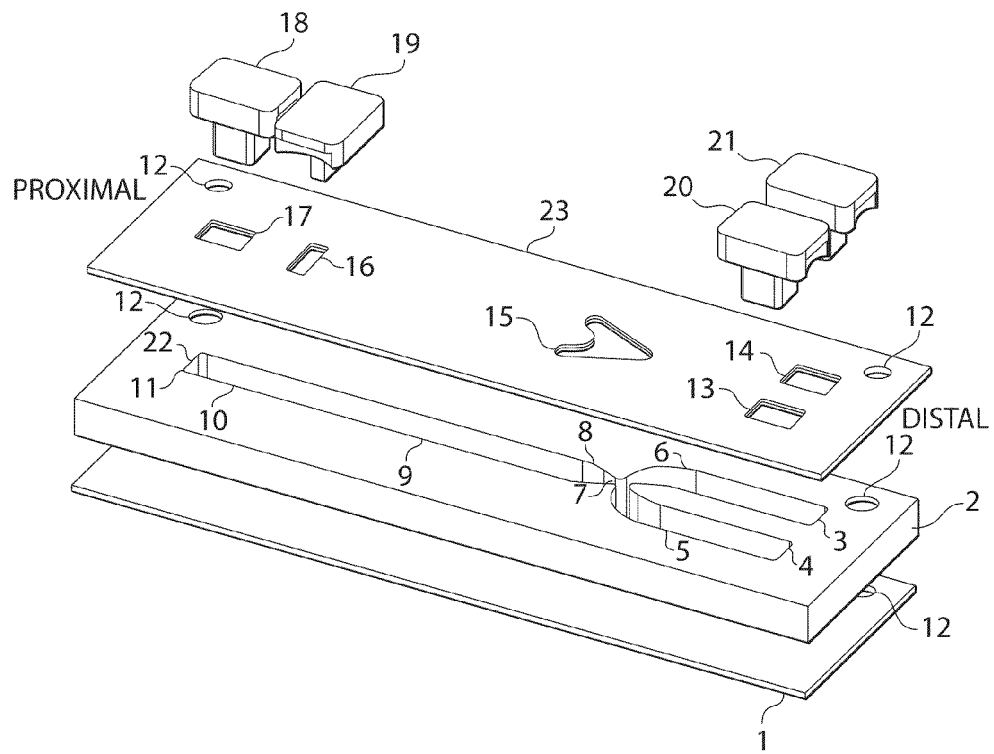
FIG. 1A is an illustration of the electrophoresis cassette used for Example 1.
Figure 1B:
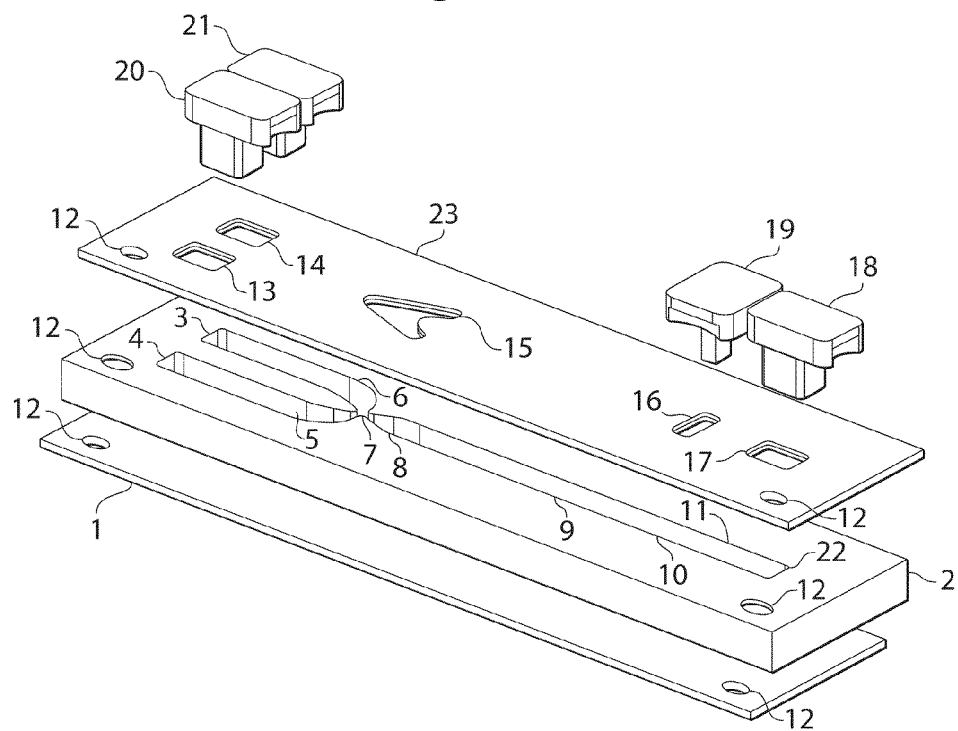
FIG. 1B is the illustration of FIG. 1, shown from an alternate perspective.

It is a common practice in biological experimentation to separate macromolecules such as proteins and nucleic acids, e.g., DNA or RNA, for analytical and preparative purposes using electrophoresis. Electrophoresis separates biomolecules by charge and/or size via mobility through a separating matrix in the presence of an electric field. Gel separating matrices are typically prepared from agarose for nucleic acid separation and polyacrylamide for protein separation. In capillary electrophoresis, the matrices may be gels or solutions (e.g., linear polyacrylamide solution).

Gel separating matrices are typically made by pouring a liquid phase material into a mold formed by glass plates or separating matrix casting molds. In slab gel electrophoresis, for example, finger shaped outcroppings in plastic material form "combs" that are embedded in the top of the separating matrix. Sample loading wells are formed when the combs are removed from the solidified separating matrix. Loading these wells is typically a time consuming and technically challenging task. Dense solutions such as glycerol or polyethylene glycol are often added to samples prior to electrophoresis to prevent samples from mixing with electrode buffers and floating out of the wells.

Samples, generally in an aqueous buffer, are applied to the separating matrix and electrodes in electrical contact with the separation matrix are used to apply an electric field. The field induces charged materials, such as nucleic acids and proteins, to migrate toward respective anode or cathode positions. Electrophoresis is usually completed in about 30 minutes to several hours.

The migration distances for the separated molecular species depend on their relative mobility through the separating matrix. Mobility of each species depends on hydrodynamic size and molecular charge. Proteins are often electrophoresed under conditions where each protein is complexed with a detergent or other material that imparts a negative charge to proteins in the sample. The detergent causes most or all of the proteins to migrate in the same direction (toward the electrophoresis anode). Samples are stained prior to, during, or after a separation run to visualize the nucleic acids or proteins within the gel. The location of the various components in the gel is determined using ultraviolet light absorbance, autoradiography, fluorescence, chemiluminescence, or any other well known means of detection. To determine the molecular weight and relative concentration of unknown nucleic acids or proteins, the band positions and intensities are typically compared to known molecular standards.

Electrophoresis cassettes and systems of the invention separate, condense, detect, analyze, and collect desired fractions of analytes within a biological sample. As described in the figures provided, and defined, in part, in Table 1, the cassettes and systems of the invention includes distinctive features and corresponding functions.

Exemplary electrophoresis cassettes are molded from a plastic, such as polystyrene and its derivatives, or PMMA. Alternatively, the electrophoresis cassette is molded using any optically clear polymer. Electrophoresis cassettes are either molded as one contiguous piece, or they are assembled from multiple pieces, each molded from plastic or an appropriate optically clear plastic that are connected to form a contiguous piece.

Electrophoresis cassettes of the invention include macrofluidic channels, rather than microfluidic channels or nanochannels, to direct and fraction samples. The use of macrofluidic channels is essential to ensure that a sufficient amount of an analyte or sample is prepared or analyzed within a single application of the sample to the cassette such that the collected fraction can be used directly for further manipulation and analysis. For example, an isolated analyte or fraction is subsequently sequenced or inserted into a vector or cell.

Figure 1C:
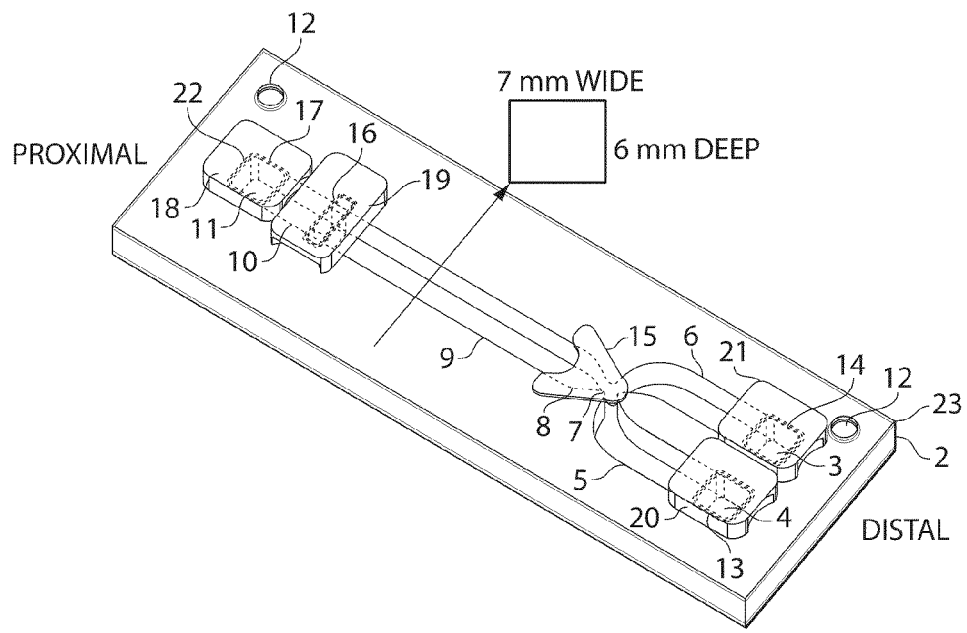
FIG. 1C is an illustration of an electrophoresis cassette providing dimensions of separation channel. Inserts are shown as transparent outlines. In an exemplary embodiment, the length from the distal edge of the sample well to the division point is approximately 53 mm.
Figure 1D:
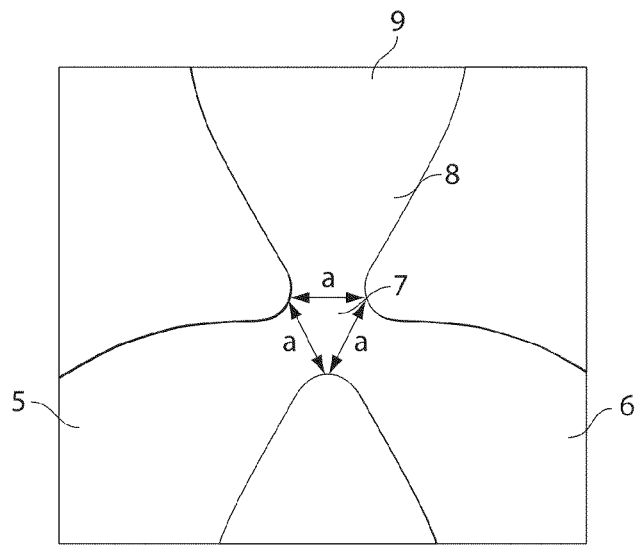
FIG. 1D is a schematic representation of the front view of channel plate at the division point of the separation channel. Length of a is, for example, 1.75 mm.

Macrofluidic channels of the invention have a minimal demonstrated width of 2 mm, which occurs at either the constriction point or division point of the channel (FIG. 1C). The greatest demonstrated width of the macrofluidic channels of the invention is 7 mm (FIG. 1C), which occurs near the sample well cavity of the separation channel. In most embodiments the depth of the macrofluidic channel is uniform, at approximately 6 mm (FIG. 1C). However, these dimensions increase and decrease within preferred ranges. The preferred width of a macrofluidic channel ranges from between 2 mm to 10 mm and the preferred depth of a macrofluidic channel ranges from between 2 mm to 10 mm.

Macrofluidic channels of the invention include physically and electrically isolated portions. The term "physically isolated" is meant to describe a channel arrangement in which one portion of the channel is separated from another portion of the channel by a physical barrier such that the analyte contained in one portion cannot intermix with the analyte contained in another portion. The term "electrically isolated" is meant to describe a channel arrangement in which the electrode positioned at one portion of the channel is controlled separately from the electrode positioned at another portion of the channel. The use of electrically and physically isolated channels both prevents contamination of the selected fractions, which can occur in gel slab systems that lack any barriers between lanes, and improves directional elution of selected fragments.

Macrofluidic channels also contain cavities and reservoirs. The term "cavity" is used to describe a portion of the channel that is reserved for either the attachment of a structure, the insertion of a structure within its volume, of the generation of a structure. A structure is formed, for instance by the placement of the sample well insert into the sample well cavity, the injection and solidification of a gel matrix composition, and the removal of the sample well insert. The term "reservoir" is meant to describe a cavity that is filled with a buffer composition.

Elution chambers of the invention include analyte-permeable and analyte-impermeable barriers. The term "analyte-permeable" is meant to describe any barrier that is permeable to ions, polynucleic acids, and polypeptides, but not to, any other component of the gel matrix composition or buffer composition. The term "analyte-impermeable" is meant to describe any barrier that is permeable to ions, but impermeable to polynucleic acids, polypeptides, any other component of the gel matrix composition, buffer composition, or elution composition.

One of the superior properties of the electrophoresis cassette of the invention is the collection analyte, or fraction thereof, in an elution buffer composition. Other preparative electrophoresis systems require the user to extract, for example, a DNA fraction, from a gel or membrane following electrophoresis. This secondary DNA extraction step is time-consuming and significantly decreases the overall yield of DNA obtained from that fraction. In contrast, electrophoresis systems of the invention integrate the steps of polynucleotide or polypeptide separation and collection by providing an elution chamber, which simultaneously fractions and extracts the polynucleotide or polypeptide analyte into any desired elution buffer.

Macrofluidic channels also include one or more engineered constriction points. Constriction points enable and improve the isolation of an analyte within sample. Physical parameters of the constriction point vary among exemplary electrophoresis cassettes and separation channels. Constriction points within existing preparative electrophoresis systems have been used to hold a vertical gel in place and reduce the volume of eluting liquid before capture. In contrast, the physical constriction of the separation channel within the electrophoresis cassettes of the invention produces an electric field gradient. In a basic embodiment, a small bore hole drilled in a plastic block serves as a constriction point.

Figures 34, 35:
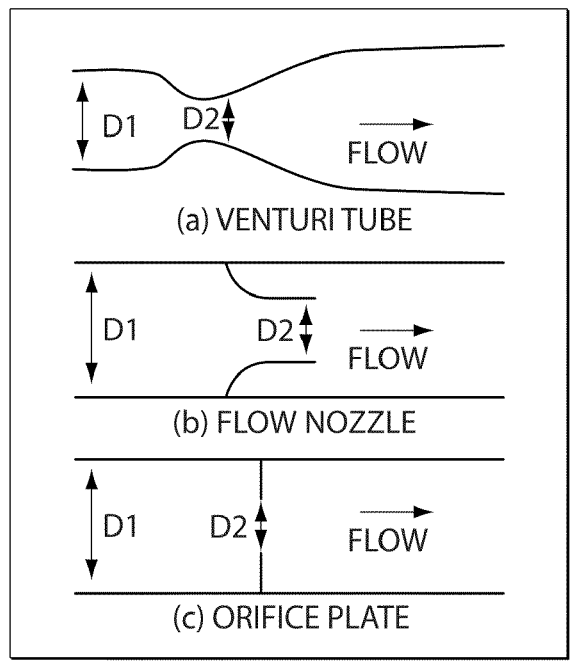
FIG. 34 is a schematic diagram of exemplary shapes of a constriction point within the separation channel of an electrophoresis cassette.
FIG. 35 is a schematic diagram of exemplary edge characteristics of a constriction point within the separation channel of an electrophoresis cassette.

Features of the constriction, or constriction point, vary between electrophoresis cassettes and between separation channels of a multichannel cassette. For example, the shape of the constriction by cross-sectional view is either a venturi tube, flow nozzle, or orifice place, as shown in FIG. 34. The placement of the constriction point within the separation channel varies. When the electrophoresis cassette is divided in half horizontally, through the separation channel, the constriction point is positioned either within the top or bottom half of the channel. When the electrophoresis cassette is divided in half vertically, through the separation channel, the constriction point is positioned either within the left or right half of the channel. Alternatively, the constriction point is located in the center of the separation channel, considered from either above-referenced perspective. From a perspective directly facing the constriction point, or a head-on perspective, the shape of the constriction is circular, oval, square, or rectangular. The cross-sectional area occupied by the constriction in comparison with the cross-sectional area of the separation channel, either upstream or downstream of the division or branch point varies. In certain embodiments the cross-sectional area occupied by the constriction occupies 90%, 80%, 70%, 60%, 50%, 40%, 30%, 20%, 10%, 5%, or any percentage point in between of the cross-sectional area of the separation channel. Additional parameters that vary between separation channels of a multichannel electrophoresis cassette or between electrophoresis cassettes include, but are not limited to, the length of the constriction, the gradient of the taper and/or flare of the constriction, the symmetry or asymmetry of the constriction, and the material used to form the constriction, as well as the texture/uniformity of that material.

The constriction point of the macrofluidic separation channel can also be the division point. Alternatively, the macrofluidic separation channel contains at least one division point. The term "division point" is meant to describe a point at which the macrofluidic channel splits or branches into one or more physically and electrically isolated portions.

Macrofluidic channels contain at least one of a gel matrix composition, a liquid buffer composition, or a solid buffer composition. Gel matrix compositions contain a polymerizing compound, such as agarose or polyacrylamide, for the separation of polynucleic acids and polypeptides, respectively. Polymerizing compounds are provided at percentages ranging from 0.01%-99.9%. Electrophoresis buffer compositions known in art are used herein. Buffer solutions are preferably electrolyte solutions.

Electrophoresis cassettes optionally contain electrodes that are either disposable or reusable. Disposable electrodes are integrated into the cassettes and made from epoxy with conductive particles, inks, or rubber. Reusable electrodes are made of coated titanium or platinum probes.

Samples, Analytes, and Fractions

Electrophoresis cassettes and detection systems of the invention fractionate, analyze, and collect polynucleic acid and polypeptide analytes or fractions within a sample.

The term "sample" describes a plurality of molecules that can be separated using gel electrophoresis. The term "fraction" describes a subset of the plurality of molecules within a sample. A fraction is defined or determined by size. Alternatively, a fraction is defined or determined by any physical property that causes it to migrate at a faster or slower rate than other components or fractions of a sample when driven to migrate through a buffer composition of the invention by the force of an electric field (i.e., electrophoretic mobility).

An exemplary sample includes, but is not limited to, a nucleic acid, an oligonucleotide, a DNA molecule, a RNA molecule, or any combination thereof. Alternatively, or in addition, a sample includes, but is not limited to, an amino acid, a peptide, a protein, or any combination thereof. For example, a sample is a whole cell lysate, or the DNA or protein fraction of a cell lysate.

Nucleic acids are derived from genomic DNA, double-stranded DNA (dsDNA), single-stranded DNA (ssDNA), coding DNA (or cDNA), messenger RNA (mRNA), short interfering RNA (siRNA), short-hairpin RNA (shRNA), microRNA (miRNA), single-stranded RNA, double-stranded RNA (dsRNA), a morpholino, RNA interference (RNAi) molecule, mitochondrial nucleic acid, chloroplast nucleic acid, viral DNA, viral RNA, and other organelles with separate genetic material. Furthermore, samples include nucleic acid analogs that contain modified, synthetic, or non-naturally occurring nucleotides or structural elements or other alternative/modified nucleic acid chemistries known in the art. Additional examples of nucleic acid modifications include the use of base analogs such as inosine, intercalators (U.S. Pat. No. 4,835,263) and minor groove binders (U.S. Pat. No. 5,801,115). Other examples of nucleic acid analogs and alternative/modified nucleic acid chemistries known in the art are described in Current Protocols in Nucleic Acid Chemistry, John Wiley & Sons, N.Y. (2002).

PNA oligomers are included in exemplary samples or fractions of the invention. PNA oligomers are analogs of DNA in which the phosphate backbone is replaced with a peptide-like backbone (Lagriffoul et al., Bioorganic & Medicinal Chemistry Letters, 4: 1081-1082 (1994), Petersen et al., Bioorganic & Medicinal Chemistry Letters, 6: 793-796 (1996), Kumar et al., Organic Letters 3(9): 1269-1272 (2001), WO96/04000).

Polypeptides or proteins are complex, three-dimensional structures containing one or more long, folded polypeptide chains. Polypeptide chains are composed of a plurality of small chemical units called amino acids. Naturally occurring amino acids have an L-configuration. Synthetic peptides can be prepared employing conventional synthetic methods, using L-amino acids, D-amino acids or various combinations of L- and D-amino acids. The term "peptide" describes a combination two or more amino acids. Naturally occurring amino acids have an L-configuration. Peptides having fewer than ten amino acids are "oligopeptides," whereas peptides containing a greater number of amino acid units are "polypeptides." Any reference to a "polypeptide" also includes an oligopeptide. Further, any reference to a "peptide" includes polypeptides and oligopeptides. Each different arrangement of amino acids forms a different polypeptide chain.

The term "nucleic acid molecule" describes the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogues thereof, such as phosphorothioates and thioesters, in either single stranded form, or a double-stranded helix. The term nucleic acid molecule, and in particular DNA or RNA molecule, refers only to the primary and secondary structure of the molecule, and does not limit it to any particular tertiary forms. Thus, this term includes double-stranded DNA found, in linear or circular DNA molecules (e.g., restriction fragments), plasmids, and chromosomes. A "recombinant DNA molecule" is a DNA molecule that has undergone a molecular biological manipulation. (see Sambrook et al. Molecular Cloning, A Laboratory Manual, Cold Spring Harbor Laboratory Press).

Samples are combined with a reagent that imparts a net negative charge, denatures a peptide or protein, or digests a DNA or RNA molecule prior to application to an electrophoresis system. These reagents are known in the art. Furthermore, samples are combined with agents that impart fluorescent, magnetic, or radioactive properties to the sample or fractions thereof for the purpose of detection. In one embodiment of the system, a dsDNA sample is mixed with ethidium bromide, applied to the electrophoresis cassette, and fractions of the sample are detected using an ultrabright green LED.

All standard and specialty buffers known in the art are used with samples, and fractions thereof, as well as to make the buffer compositions the fill the electrophoresis cassettes of the system.

Regarding polypeptides, the term "native" is meant to describe a non-denatured polypeptide. Polypepide analytes of the invention are native or denatured.

Detection System

Detection systems of the invention are compact and automated. These systems are designed and intended for desktop or bench-top use. Furthermore, electrophoresis cassettes of these systems are disposable.

Systems include at least one electrophoresis cassette with means to fractionate, detect, analyze, and collect a polynucleic acid or polypeptide analyte or fraction within a sample.

Systems also include a detection module with means to detect and analyze, for instance, to quantify, a signal. Exemplary signals include, but are not limited to, visible light, fluorescent light, magnetic fields, and radioactivity. Detection modules are positioned at a detection zone or constriction point of the separation channel of an electrophoresis cassette. Alternatively, the position of the detection module is shifted towards the entry or exit points of the constriction. The constriction point or detection zone is proximal to the sample well. The detector tracks a marker and the processor determines, based upon the size, speed, electrophoretic mobility, and/or timing of the marker, when an analyte of the desired molecular weight or electrophoretic mobility will traverse the division point.

Included in these systems is an illumination source that is either independently incorporated into the system or incorporated into the detection module. The illumination source uses ultra bright light emitting diode (LED) in combination with a filter set and one or more photodiodes, for instance.

The detection module of the system, which optionally includes an illumination source, is coupled with a microprocessor control system. The microprocessor control system includes a microprocessor, software, and a set of relays with means to control a voltage switching scheme that differentially activates a combination of the negative and at least one positive electrode in order to divert a sample or fraction thereof to an intended collection point at the end of the separation channel. In another aspect of the invention, a laptop is substituted for the use of an incorporated microprocessor. Exemplary software for controlling these systems is developed for use on a laptop or with the incorporated microprocessor.

Systems further include an integrated or separate power source.

Systems of the invention are designed to such that the separation channels of the incorporated electrophoresis cassettes are positioned horizontally with respect to a table- or desktop. Alternatively, the system is configured such that the separation channels of the incorporated electrophoresis cassettes are positioned vertically with respect to a table- or desktop.

TABLE 1

Figure Reference Numbers

| Reference Number | Structure |
|---|---|
| 1 | Base plate |
| 2 | Channel plate |
| 3 | Waste reservoir |
| 4 | Elution reservoir |
| 5 | First physically and electrically isolated portion of separation channel |
| 6 | Second physically and electrically isolated portion of separation channel |
| 7 | Division Point |
| 8 | Constriction Point |
| 9 | Separation channel |
| 10 | Sample well cavity |
| 11 | Buffer reservoir |
| 12 | Alignment excision |
| 13 | Elution reservoir insert opening |
| 14 | Waste reservoir insert opening |
| 15 | Constriction and division point opening |
| 16 | Sample well insert opening |
| 17 | Buffer reservoir insert opening |
| 18 | Buffer reservoir insert |
| 19 | Sample well insert |
| 20 | Elution reservoir insert |
| 21 | Waste reservoir insert |
| 22 | End of separation channel |
| 23 | Cover plate |
| 24 | DNA sample |
| 25 | Desired analyte or fraction |
| 26 | Groove |
| 27 | First removable end of elution chamber |
| 28 | Sample collection chamber of elution chamber |
| 29 | Sample collection port of elution chamber |
| 30 | Second removable end of elution chamber |
| 31 | Gasket |
| 32 | Analyte-permeable barrier (e.g. Durapore Membrane) |
| 33 | Analyte-impermeable barrier (e.g. Nafion Membrane) |
| 34 | Elution chamber spacer |
| 35 | Elution chamber wedge |
| 36 | Sample collection channel |
| 37 | O-ring |
| 38 | DNA Marker |
| 39 | Negative Electrode |
| 40 | Sample well |
| 41 | Positive Electrode |
| 42 | Connector |
| 43 | Elution chamber opening in cover |
| 44 | Alignment protrusion |
| 45 | Elution chamber cavity |
| 46 | Elution chamber |
| 47 | Elution reservoir and waste reservoir cavity |
| 48 | Waste reservoir insert |
| 49 | Vent |
| 50 | Injection Port |
| 51 | Electrophoresis cassette |
| 52 | Processor board for power module |
| 53 | Input/Output connector |
| 54 | Single computer board |
| 55 | Optics housing |
| 56 | Photodetector |
| 57 | Photodetector processor board |
| 58 | Hard disk drive |
| 59 | Light-emitting diode |
| 60 | Casing of detector system |
| 61 | Light-emitting diode |
| 62 | Emission filter |
| 63 | Light-focusing filter |
| 64 | Dichronic mirror |
| 65 | Excitation filter |

EXAMPLES

Example 1

Size Fractionation of Genomic DNA by Agarose Gel Electrophoresis in Y-Shaped Cassette The Y-shaped cassette used for this experiment is illustrated in FIG. 1. The channel plate and cover were machined from polycarbonate, the base was fused silica, and the molding inserts used to form buffer and sample wells were machined from Teflon. To cast the gel cassette, the channel plate was coated front and back with a thin coating of a dielectric silicone sealant to prevent leakage of buffer and electrical current. The base and cover were pressed against the channel plate and held together with binder clips throughout casting and electrophoresis.

The electrophoresis gel used was 2% agarose (SeaKem LE agarose, Lonza) in 0.5×KBB buffer (1×KBB buffer is 12.4 g/liter Tris base, 14 g/liter TAPS acid, 0.048 g/liter EDTA free acid). The gel and liquid buffer contained 1.5 ug/ml ethidium bromide, to enable visualization of the DNA by fluorescence under UV transillumination. The agarose was heated in water until dissolved and then cooled to approximately 60° C. Buffer and ethidium were added and the solution was thoroughly mixed. The cassette was filled in a horizontal position, with all well-forming inserts removed, until the cassette was slightly overfilled. The well-forming inserts were immediately installed. The triangular gap in the cassette cover which is located over the channel constriction was covered with a glass coverslip. Care was taken to avoid introduction of bubbles or silicone sealant into the channel.

The cassette was allowed to solidify for approximately 1 hour at room temperature. The well-forming inserts were removed from the cassette and all wells were filled with electrophoresis buffer (0.5×KBB buffer with 1.5 ug/ml ethidium bromide). The cassette was placed in a horizontal position on a UV transilluminator (Fotodyne, 300 nm peak output). A high voltage electrophoresis power supply (E-C apparatus) was connected to platinum electrodes in the buffer reservoirs of the cassette.

A sample of calf thymus DNA (Sigma Chemical) was digested to completion with BfuCI (New England Biolabs). Two ug of digested DNA was dissolved in 40 ul of 40% sucrose, 10 mM Tris-HCl, pH 8.0, 1 mM EDTA, and loaded in the sample well of the cassette.

Electrophoresis was carried out at a constant voltage of 100 V. The negative electrode was connected to the single buffer reservoir upstream from the sample well. The positive electrode was connected to buffer reservoir of the waste leg of the cassette initially. The electrophoresis buffer reservoirs were exchanged with fresh buffer every 10 minutes during the run.

Figure 2A:
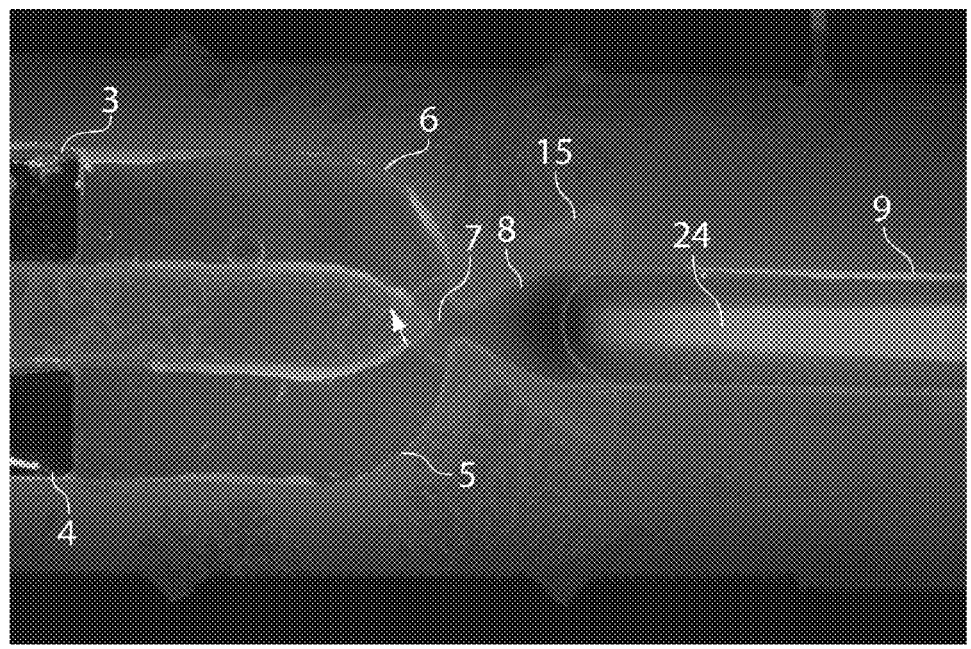
FIG. 2A-L is a series of photographs showing the fractionation of genomic DNA by size differentiation over time using the electrophoresis cassette of FIG. 1 and Example 1. The arrow indicates the direction of electrophoresis at the division point, i.e. the arrow points in the direction of the positive electrode that is differentially activated.
Figure 2B:
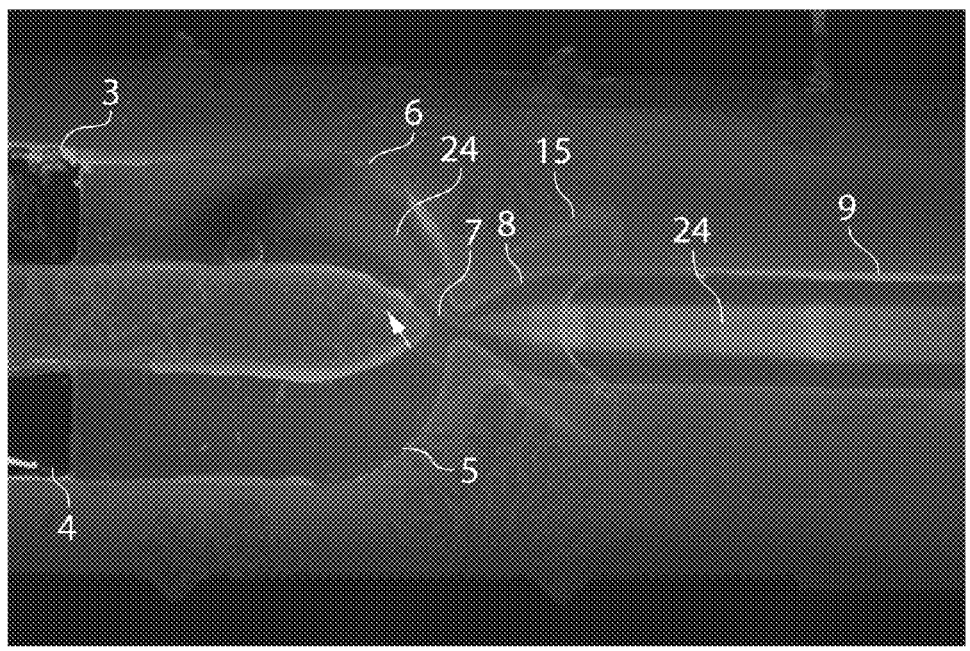
Figure 2C:
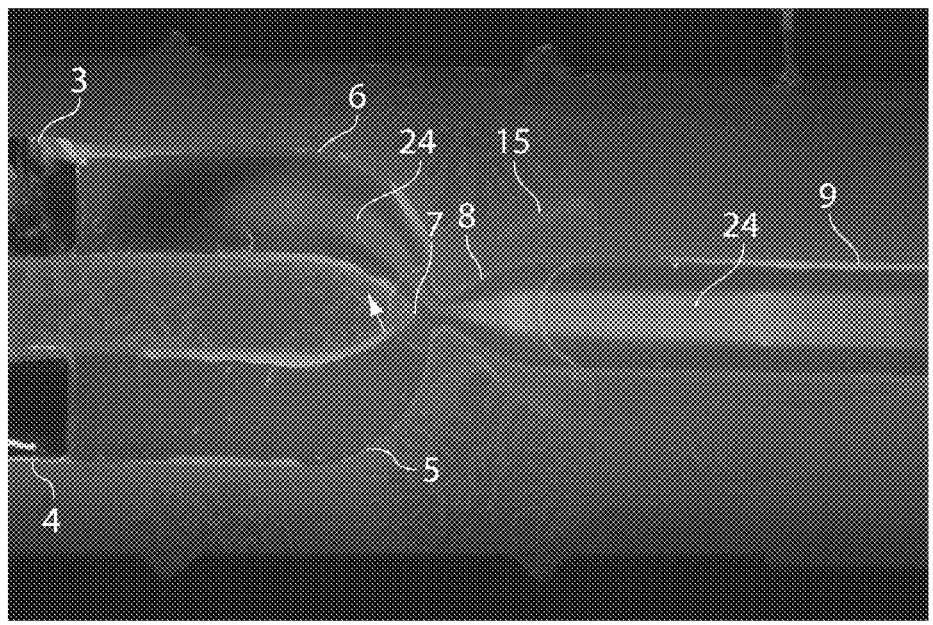
Figure 2D:
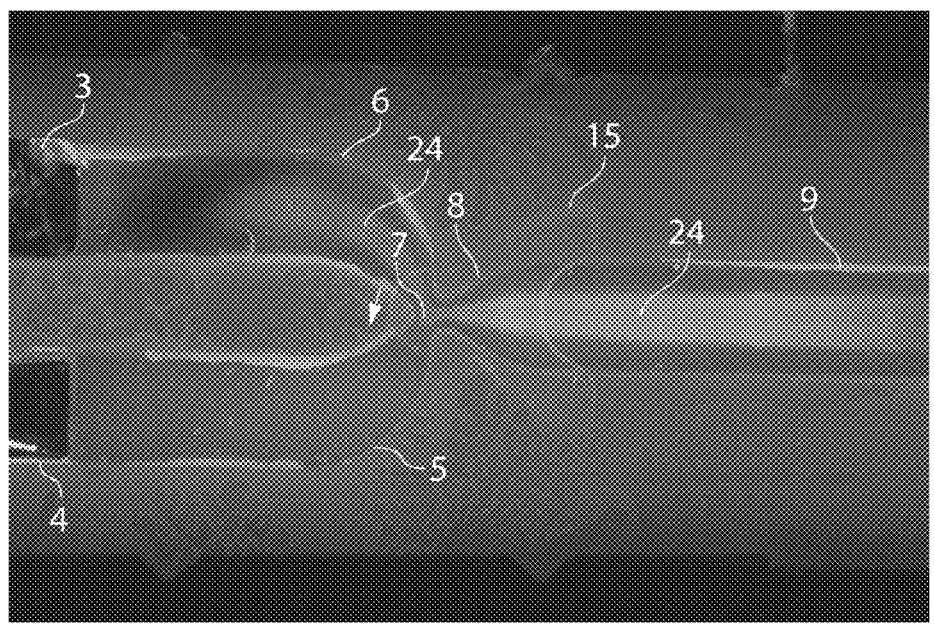
Figure 2E:
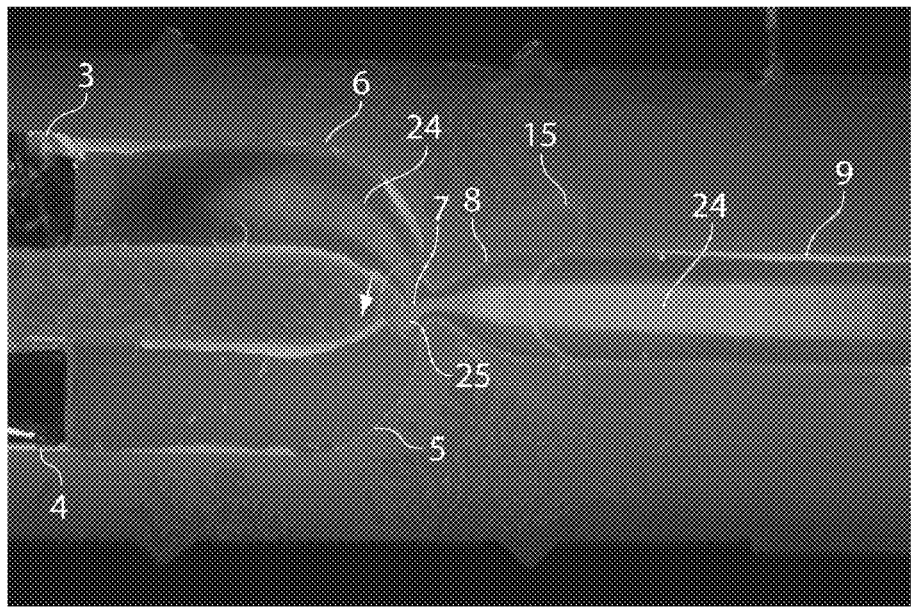
Figure 2F:
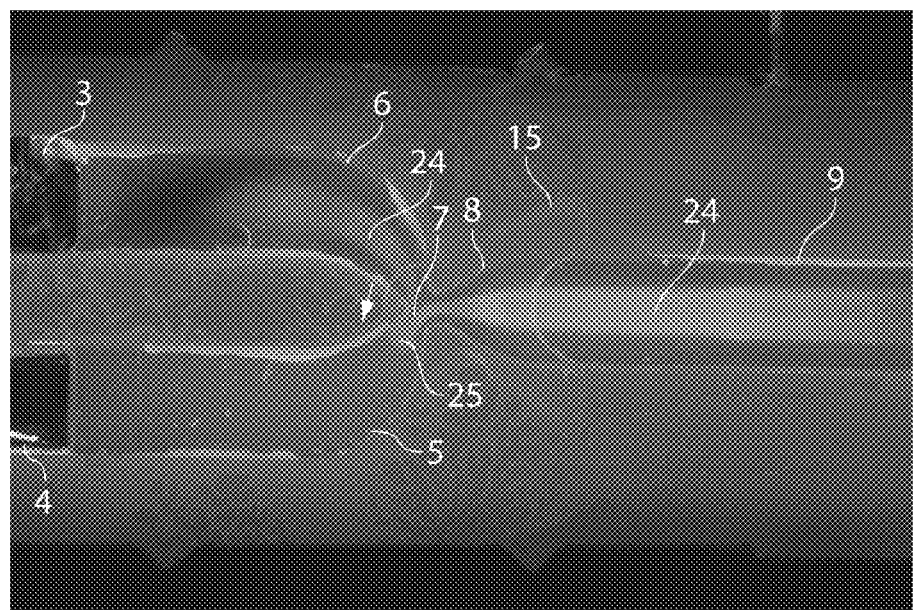
Figure 2G:
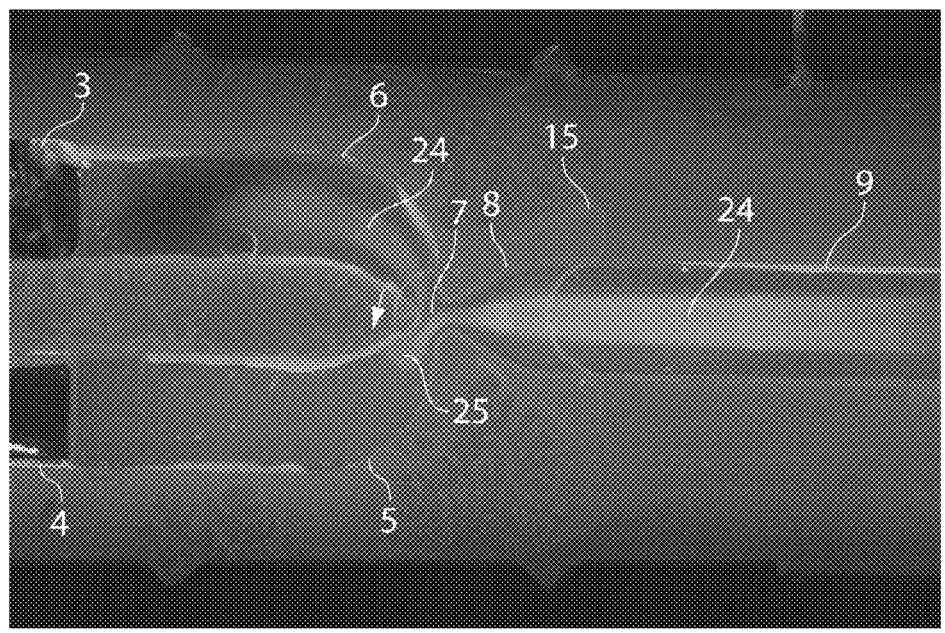
Figure 2H:
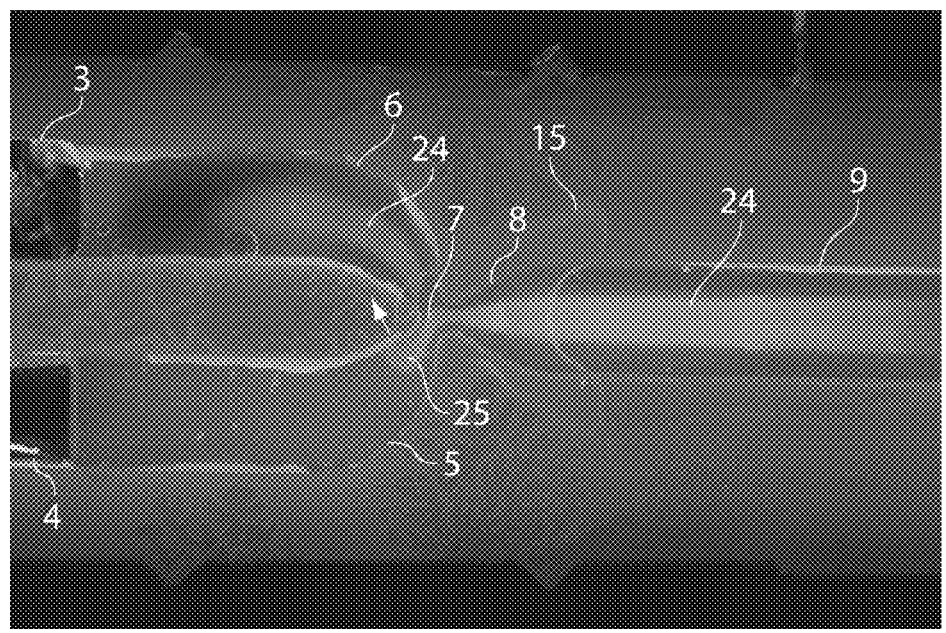
Figure 2I:
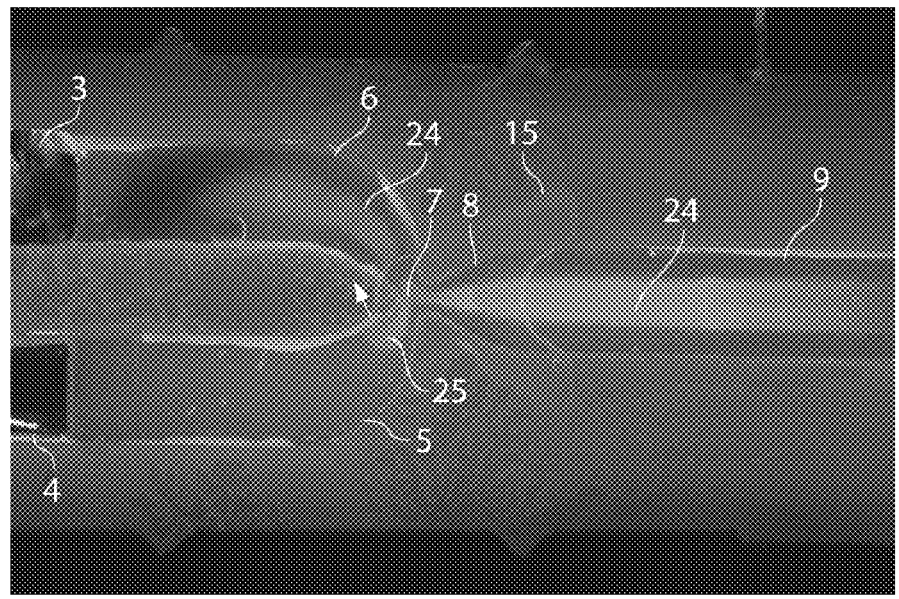
Figure 2J:
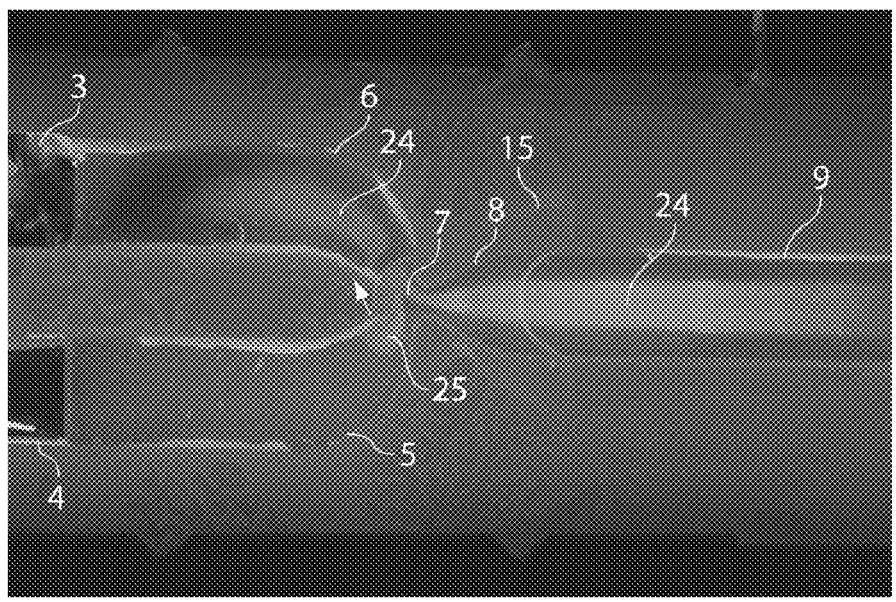
Figure 2K:
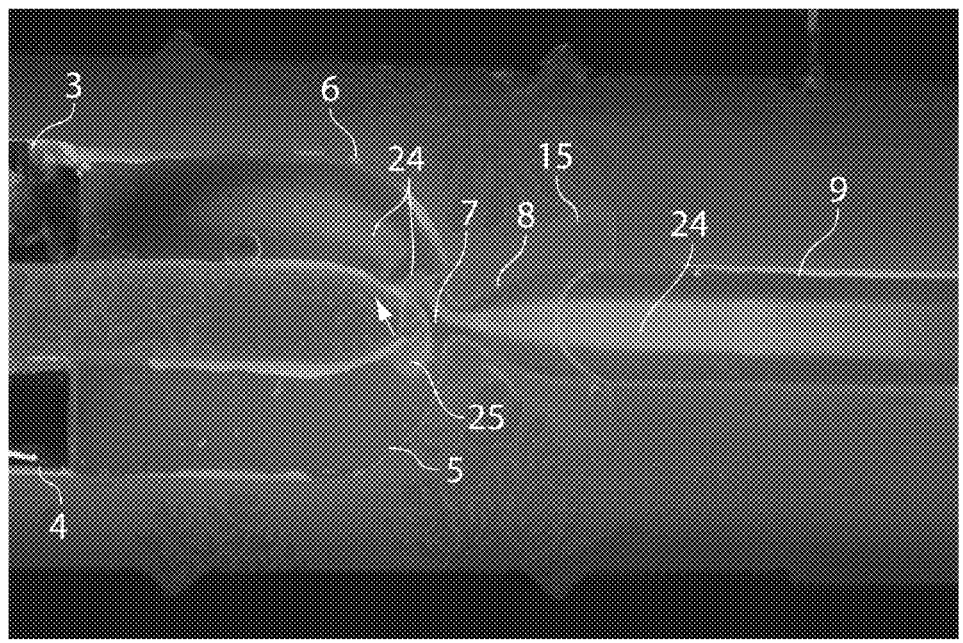

Electrophoresis was carried out using the waste leg electrode for 57 minutes (see images FIG. 2A-C). At that point, waste leg electrode was disconnected, and the purification leg electrode was connected to the power supply for 2 minutes (see images FIGS. 2D-G). After 2 minutes, the purification leg electrode was disconnected and the waste leg electrode was reconnected. Electrophoresis was continued into the waste leg for approximately 3-4 more minutes (see images FIGS. 2H-L). Then power was turned off. The cassette was unclamped and the cover was removed. The gel in the separation channel was cut away from the gel in the purification and waste legs of the cassette near the narrowest point of the legs. The separation channel gel was discarded and the separation channel was refilled with electrophoresis buffer.

Figure 2L:
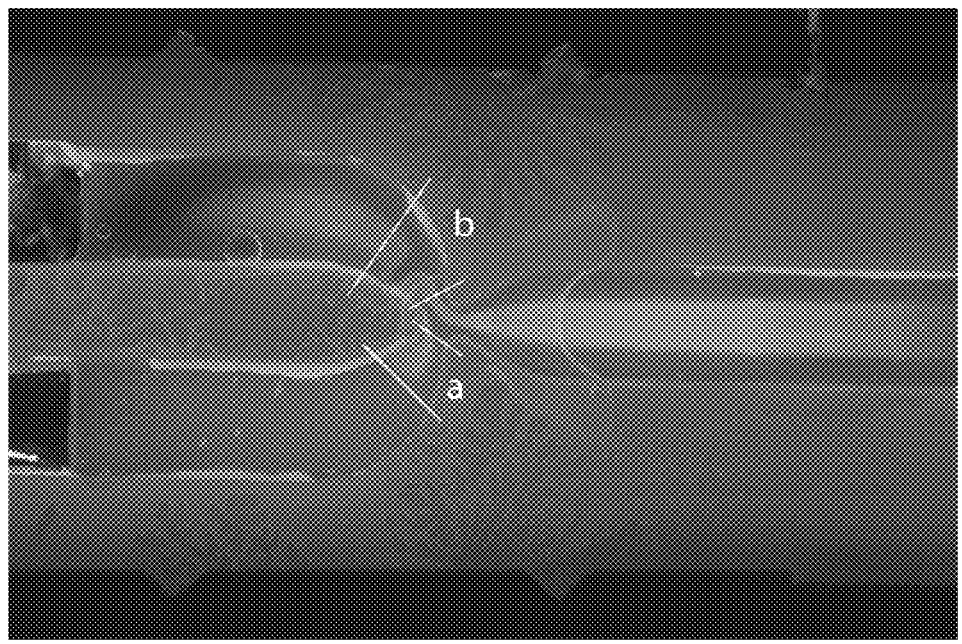

DNA in the waste and purification channels was isolated by electrophoresing the DNA onto strips of DEAE ion-exchange membrane (Sartorius Stedim) were inserted into thin horizontal slits in the gel just downstream of the desired DNA fractions (see FIG. 2L). Electrophoretic capture of the DNA on the membranes was carried out at 100 V for approximately seven minutes. Purification leg DNA was isolated first and sample membrane was removed to prior to isolation of DNA from the waste leg.

Figure 2M:
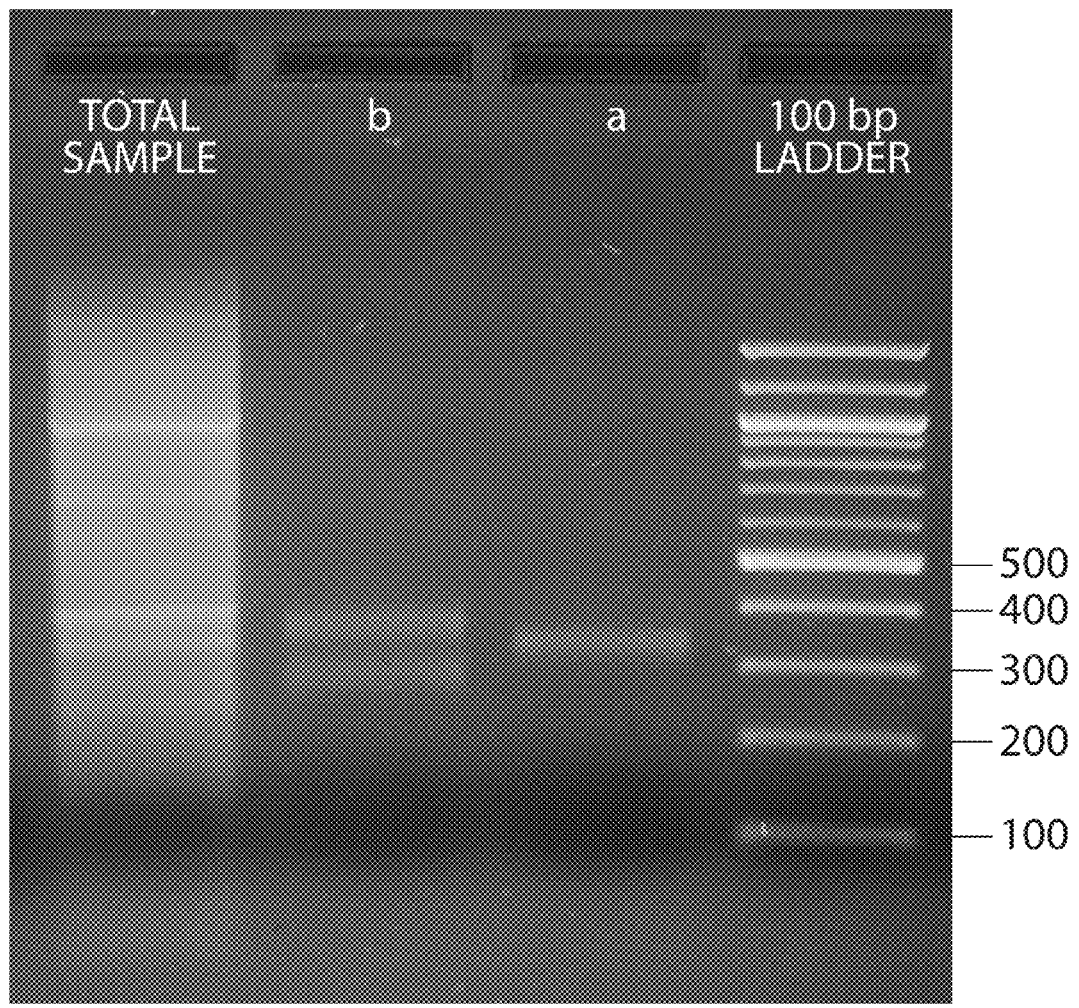
FIG. 2M is a photograph of a 2% agarose gel, in which the results of the fractionation of FIG. 2A-L were analyzed. The purified fraction collected in the elution chamber measured 344±20 base pairs (bp).

DNA was recovered from ion-exchange membranes, by immersing membranes in 0.4 ml 1×KBB and 1M NaCl at 65° C. for 30 minutes. After removal of ion-exchange strips from tubes, 10 ul of 0.25% linear polyacrylamide was added to each tube and vortexed to mix. DNA was precipitated with 1 ml ethanol to each tube. DNA pellets were rinsed in 100% ethanol, and air dried. DNA samples were resuspended in 15 ul TE buffer (10 mM Tris-HCl, pH 8.0, 1 mM EDTA), and mixed with 15 ul of 40% sucrose in TE buffer. Entire amount was loaded onto 2% analytical slab agarose gel in 0.5×KBB with 1.5 ug/ml ethidium bromide. The image of the analytical gel is shown in FIG. 2M. The DNA recovered from the purification leg measures approximately 344 bp with an edge to edge band width of approximately 40 bp. The DNA from the waste leg shows almost complete absence of DNA in the region of 340 bp, indicating good purification efficiency into the purification leg.

Example 2

Figure 3A:
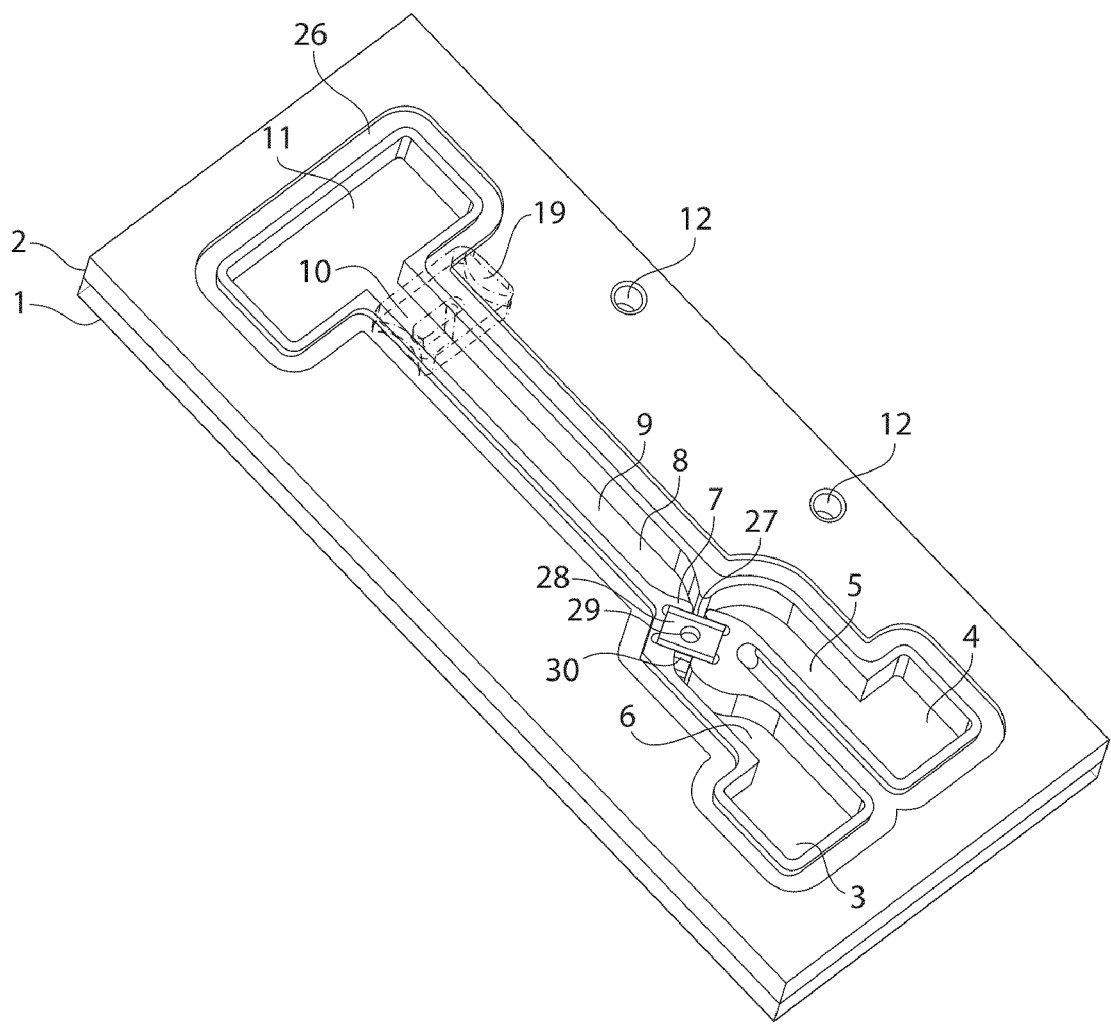
FIG. 3A is an illustration of a preparative electrophoresis cassette with an elution chamber.
Figure 3B:
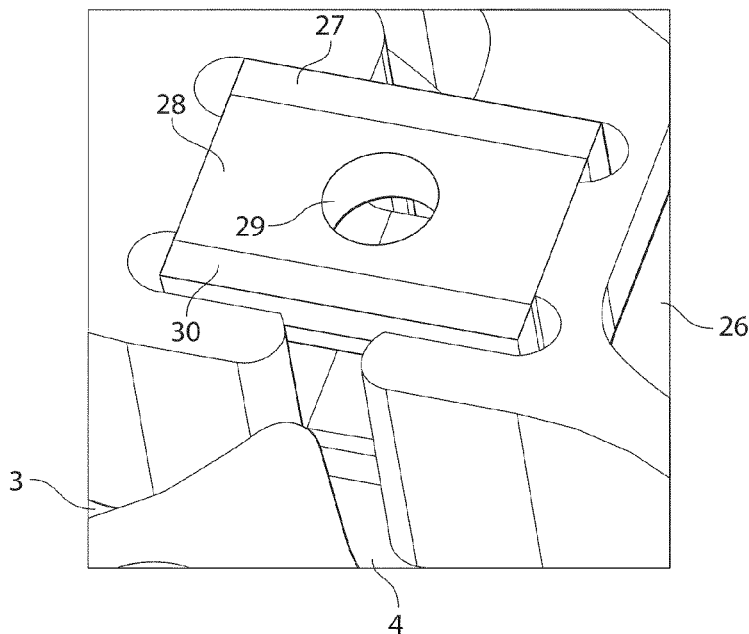
FIG. 3B is an illustration of a preparative elution chamber from the perspective of the separation channel.
Figure 3C:
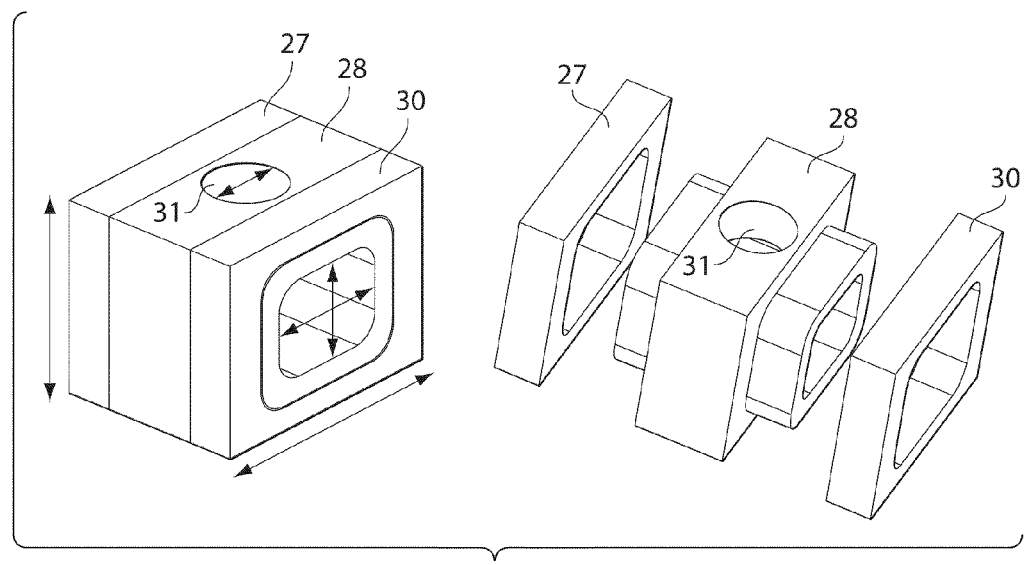
FIG. 3C is a pair of photographs of a preparative elution chamber. Left Panel: Exemplary dimensions for the elution chamber are as follows: diameter of sample collection port=2.5 mm, height of elution chamber=6 mm, width of elution chamber=8 mm, depth of elution chamber=6 mm. With respect to the opening in the side of the elution chamber, exemplary dimensions are as follows: the width=4 mm, height=3 mm. Right Panel: Disassembled view of elution chamber showing a first removable side, a sample collection chamber and a second removable side. The sample collection chamber contains a sample collection port, which is located, for instance, on the top side of the chamber.

Size Fractionation of Genomic DNA by Agarose Gel Electrophoresis in Y-Shaped Cassette with Liquid Filled Elution Chamber In order to demonstrate recovery of fractionated size-selected DNA in a liquid filled buffer chamber, the device of FIG. 1 was modified to include a membrane-bounded chamber in the purification channel. The cassette with elution chamber is shown in FIGS. 3A-C. The dimensions of the separation channel and waste channel were similar to the cassette of FIG. 1.

Figure 4A:
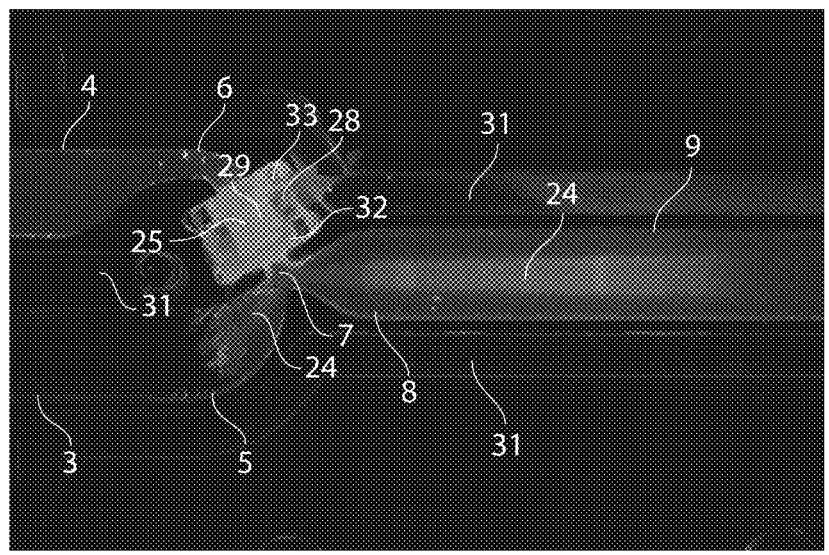
FIG. 4A is a photograph of an electrophoresis cassette combined with the elution chamber of FIG. 3 and Example 2.

The elution chamber was a rectangular plastic channel (polycarbonate) that was bounded on the front side (the side proximal to the separation channel, see FIG. 4A, 3B) by a membrane that is porous to DNA, and low in nonspecific DNA binding (Durapore SVLP, Millipore, 5 um pore size). On the back side of the chamber (the side proximal to the (+) electrode, see FIG. 4A, 3B), a membrane that is non-porous to DNA and low in nonspecific DNA binding was installed (Nafion 117, Ion Power). The membranes were tightly sealed over the faces of the elution chamber by rectangular plastic frames that snap over the protruding lip of the chamber (see FIG. 3C). The top surface of the elution chamber has a small circular hole which was used for filling and emptying the channel with a standard handheld micropipettor (FIGS. 3C and 4A). The volume of the fully assembled elution chamber was approximately 90 ul.

The cassette was assembled as described in Example 1, with the exceptions that dielectric silicone sealant was not used between the channel plate and the top cover. In this example, the top surface of the channel plate was sealed with a cast silicone gasket, which is labeled in FIGS. 3C and 4A.

The agarose gel (same composition as in Example 1) was cast with an empty, membrane-free elution chamber inserted into the cassette. After the gel solidified, the top plate was removed and the gel column was sliced across the front and back openings of the gel elution chamber. The elution module was removed and the gel was cleaned from the inside of the module. Nafion and Durapore membranes were assembled onto the chamber, and it was reinserted into the cassette. Dielectric silicone sealant was used on the side and bottom exterior surfaces of the elution chamber to prevent electrical leaks around the elution chamber. The assembled cassette was clamped with binder clips as in Example 1.

The sample was 2 ug BfuCI-digested calf thymus genomic DNA. Electrophoresis was carried out at constant voltage of 100 V. The waste channel electrode was used for 1 hr and 9 minutes, and then voltage was switched to the purification channel for 5 minutes. Following this, voltage was switched back to the waste channel for an additional 3 minutes before terminating electrophoresis.

After the run, 90 ul of buffer was removed from the elution chamber with a hand-held micropipette. Eluted sample was ethanol precipitated as described in example 1. To estimate the efficiency of DNA recovery by the process, DNA in the gel of the waste leg was isolated in the vicinity of the "gap" in the DNA pattern (caused by the removal of DNA into the purification channel). DNA was extracted from the gel slice using a commercial kit (Qiagen Minelute Gel extraction kit).

Figure 4B:
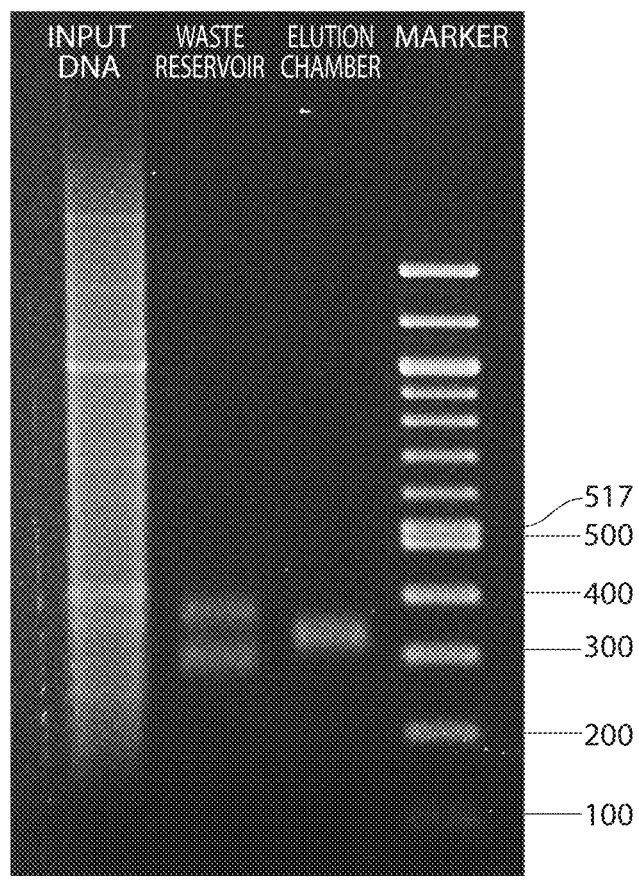
FIG. 4B is a photograph of an agarose gel analysis of fractions collected from the electrophoresis cassette of FIG. 4A.

An analytical 2% agarose gel of the products (see FIG. 4B) shows efficient purification of a DNA band of approximately 300 bp, similar to the results shown in Example 1. In this example, however, the selected DNA product was obtained in liquid buffer directly from the elution chamber, without the need to perform gel extraction. The fractionation process was efficient, as judged by the absence of similar-sized DNA in the sample recovered from the waste channel.

Example 3

Figure 5A:
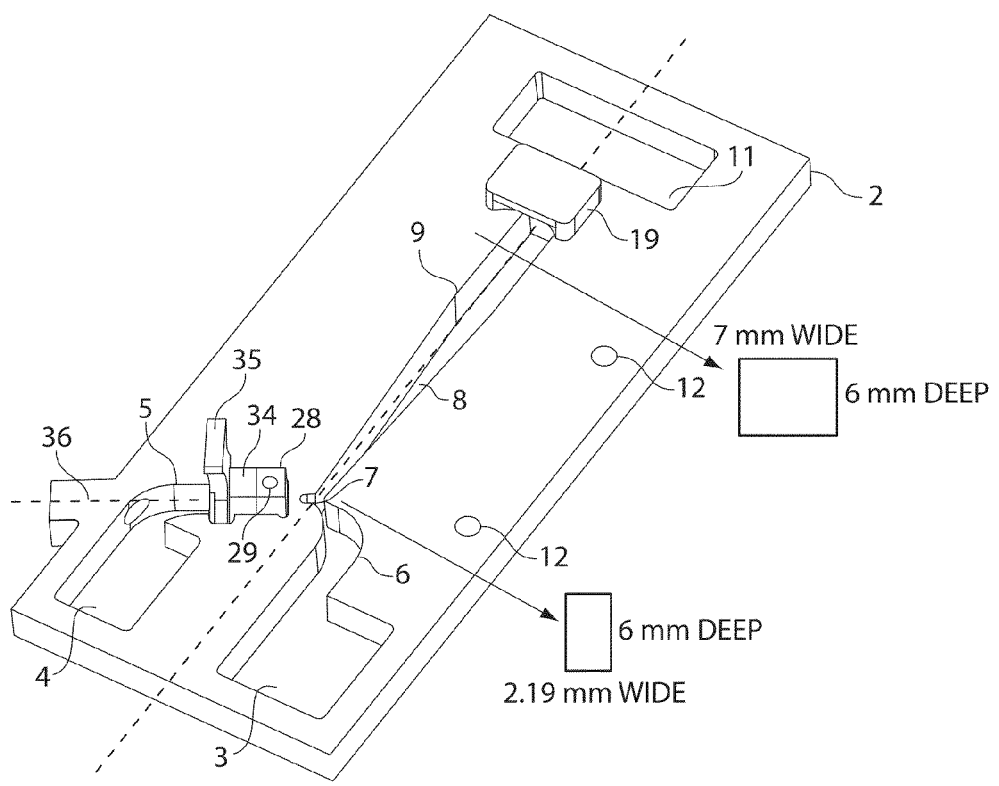
FIG. 5A is an illustration of an electrophoresis cassette with a tapered separation channel combined with an elution chamber including a spacer, wedge, and O-ring seals. In one embodiment, the length of the separation channel from the distal edge of the sample well to the division point is 67 mm.
Figure 5B:
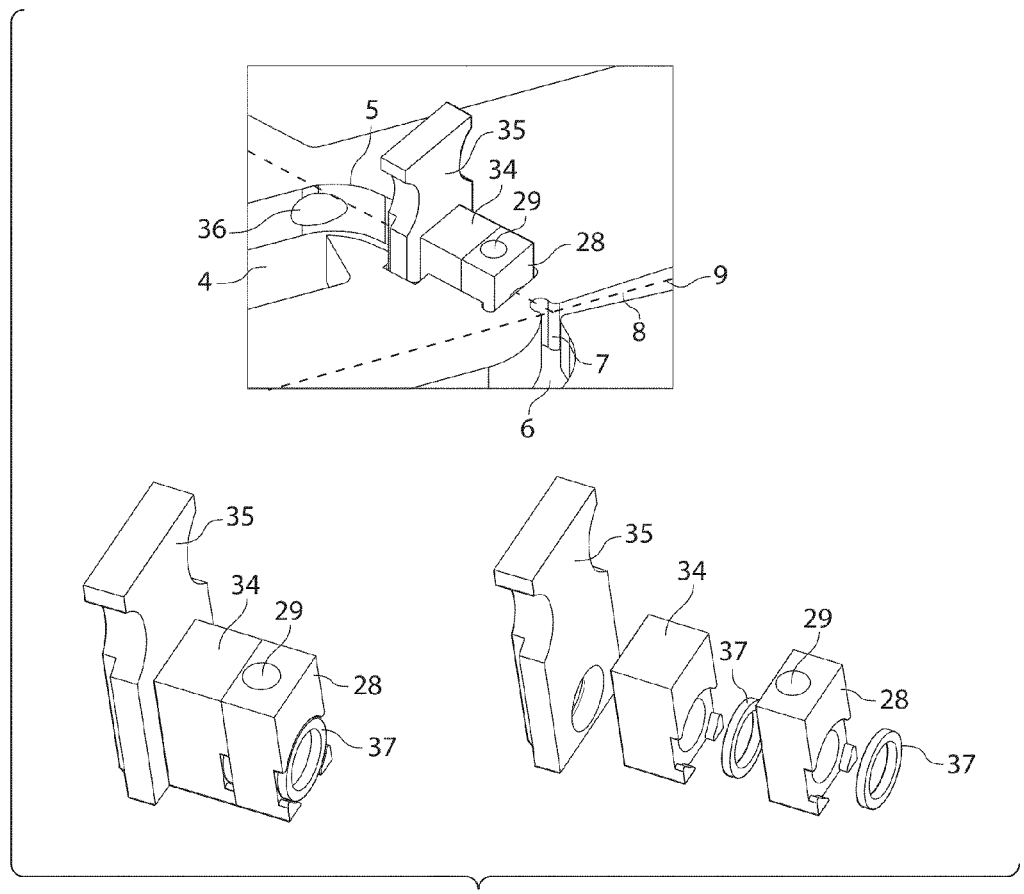
FIG. 5B is a series of illustrations of an elution chamber assembly shown in FIG. 5A. Exemplary dimensions of the elution chamber are as follows: the height of the sample collection chamber and the wedge=10 mm, the depth of the sample collection chamber=4 mm, and the diameter of the O-ring is 4 mm.
Figure 6A:
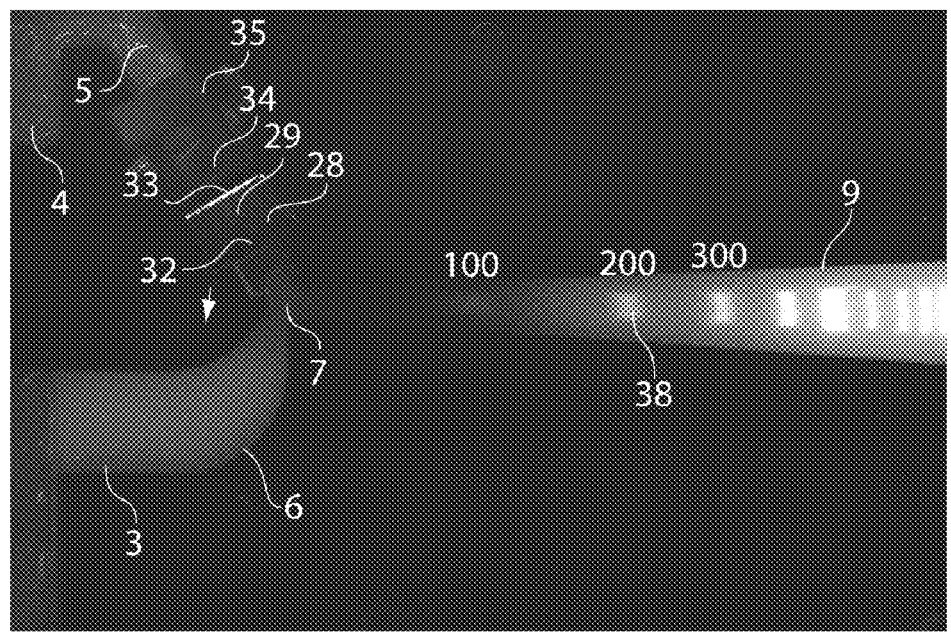
FIG. 6A-F is a series of photographs depicting the capture of a 200 bp fraction, of a DNA ladder over time using the electrophoresis cassette of FIG. 5 and Example 3. Arrow indicates the direction of electrophoresis at the division point.
Figure 6B:
Figure 6C:
Figure 6D:
Figure 6E:
Figure 6F:
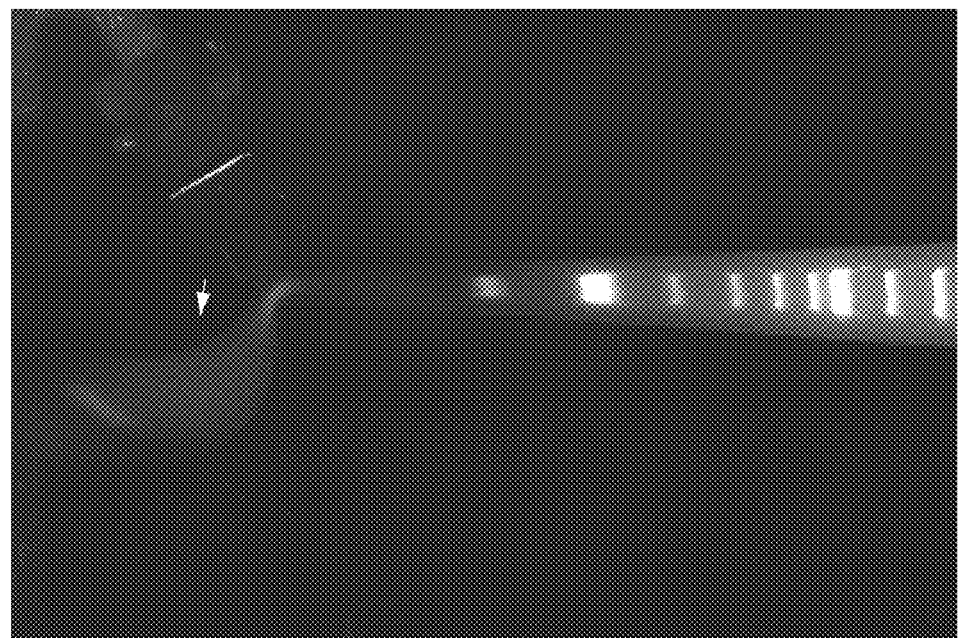

Purification of Specific DNA Band in Cassette with Tapered Channel and Simplified Elution Chamber Design An alternative cassetted design is shown in FIGS. 5A-B. The cassette features a tapered separation channel. As seen in FIGS. 6D-F, DNA bands are compacted from their original thin and wide shape near the sample well into square (or compact rectangular) shapes as they arrive at the three-way channel junction. For this reason, a tapered separation channel should provide improved size resolution in purification when compared with separation channels with rectangular profile like those described in Examples 1 and 2 above.

The elution chamber of this cassette is constructed from three plastic parts shown in FIG. 5B. Compressible O-rings are used to position and seal membranes on either side of the elution chamber, as illustrated in FIG. 5B. The volume of the elution chamber is approximately 50 ul.

To cast the gel used for this example (same gel and buffer formulation as used in Example 1 above), the top and bottom surface of the channel plate was sealed with clear packaging tape (Scotch brand packaging tape, 3M). The purification channel and electrophoresis buffer compartments were left uncovered on the top side of the channel plate. The elution chamber was assembled with a non-porous sheet of PETG sealing the chamber entrance from the separation channel side. The gel was cast through the buffer reservoir of the waste channel, thereby filling the waste and separation channels only. The purification channel contained no gel, except at the entrance to the elution chamber. After the gel solidified, the elution chamber was disassembled and the PETG membrane was discarded. The purification channel was filled with electrophoresis buffer. The elution chamber was reassembled in the buffer-filled purification channel with porous membrane (Durapore BVPP, 1 um pore size, Millipore) on the separation channel side of the chamber, and non-porous membrane (Nafion 117) on the electrode side of the chamber. Care was taken to ensure that no bubbles were trapped in the channel through the elution chamber and spacer.

The sample consisted of 1 ug of a 100 bp DNA marker ladder (100 bp ladder, New England Biolabs). Electrophoresis was carried out a constant voltage of 100 V. The waste channel electrode was used (see FIGS. 6A-D) until the 200 bp marker arrived at the three way junction between separation, purification, and waste channels (approximately 71 minutes into the run, see FIG. 6E). At this point, voltage was switched to the purification channel and the 200 bp band was driven into the elution chamber for 6 minutes (see FIGS. 6E-F). The voltage was switched back to the waste channel for an additional 15 minutes after which the run was terminated.

Figure 6G:
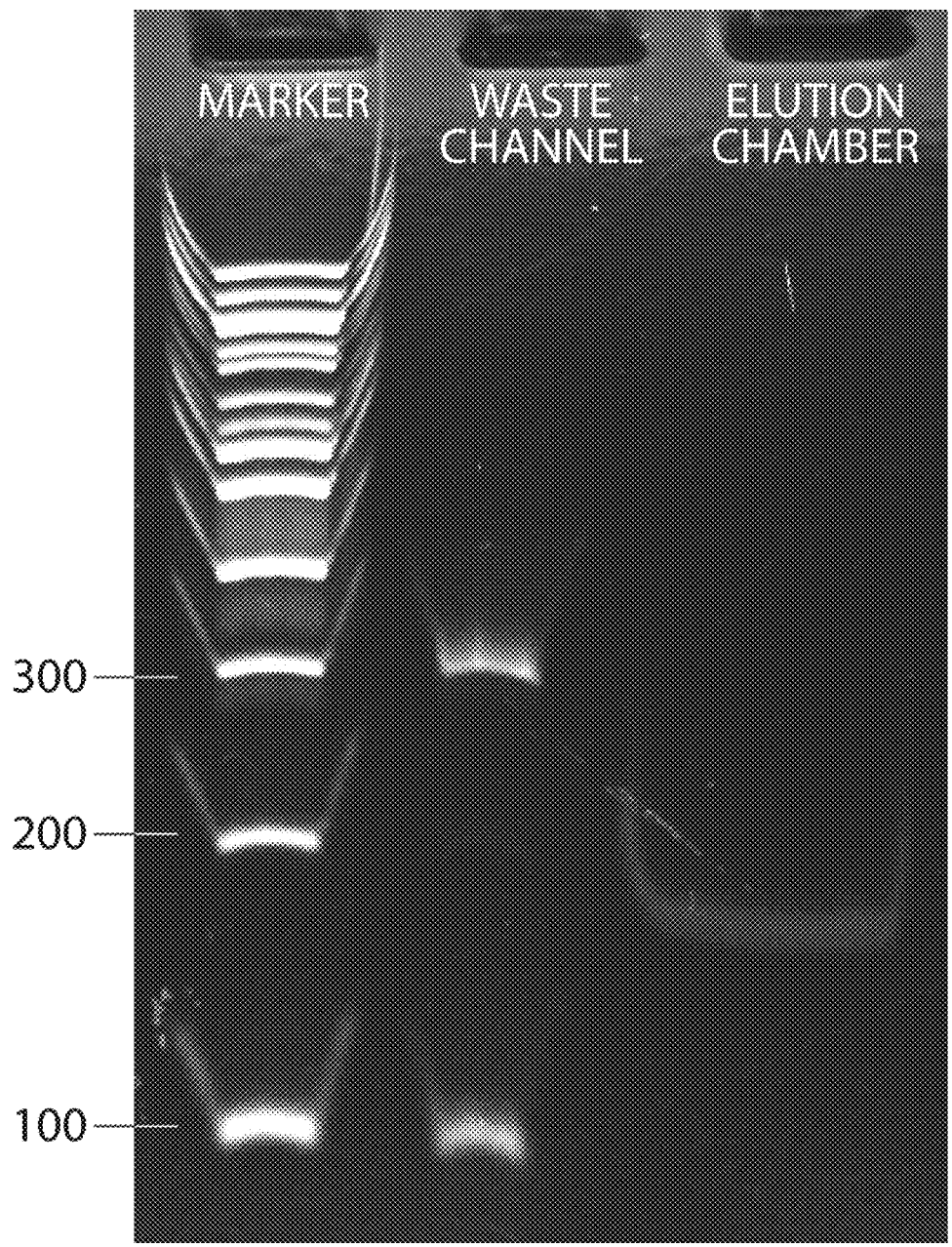
FIG. 6G is a photograph of an agarose gel analysis of the experiment of FIG. 6A-F confirming the specific capture of the 200 bp fraction in the elution chamber.
Figure 7:
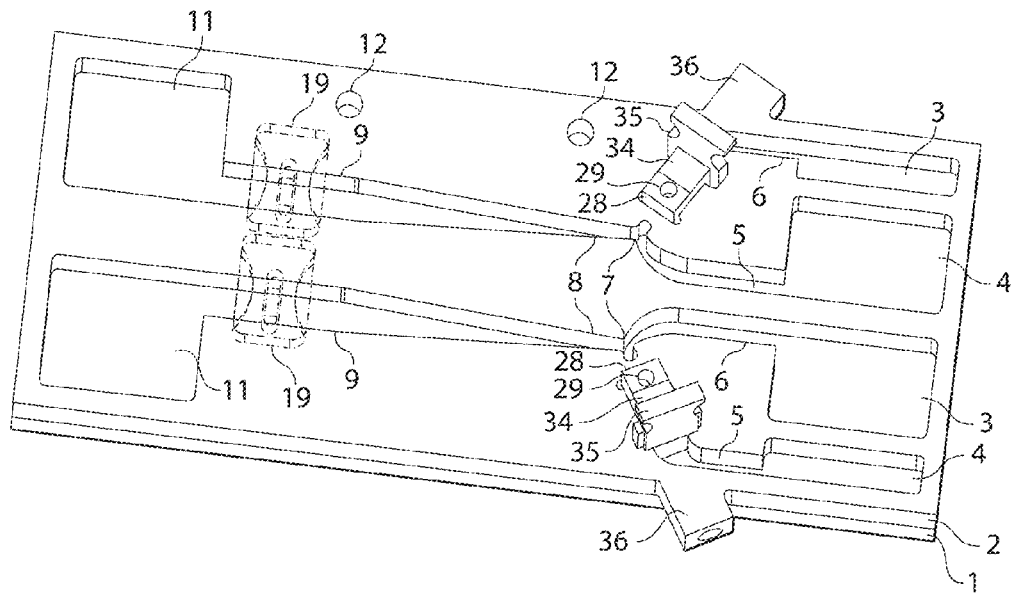
FIG. 7 is an illustration of a multichannel preparative electrophoresis cassette.
Figure 8A:
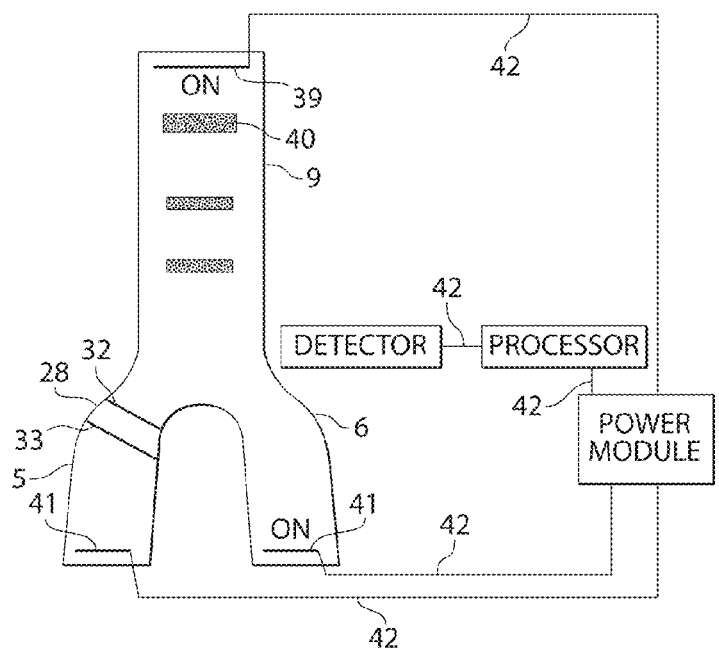
FIG. 8A-H is a series of illustrations showing the fractionation of a sample over time using an exemplary detection system.
Figure 8B:
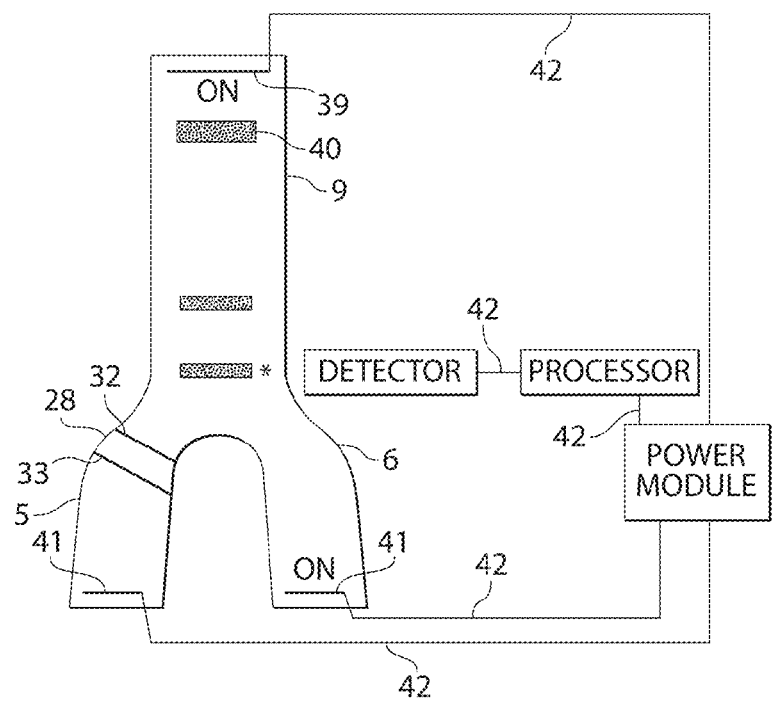
Figure 8C:
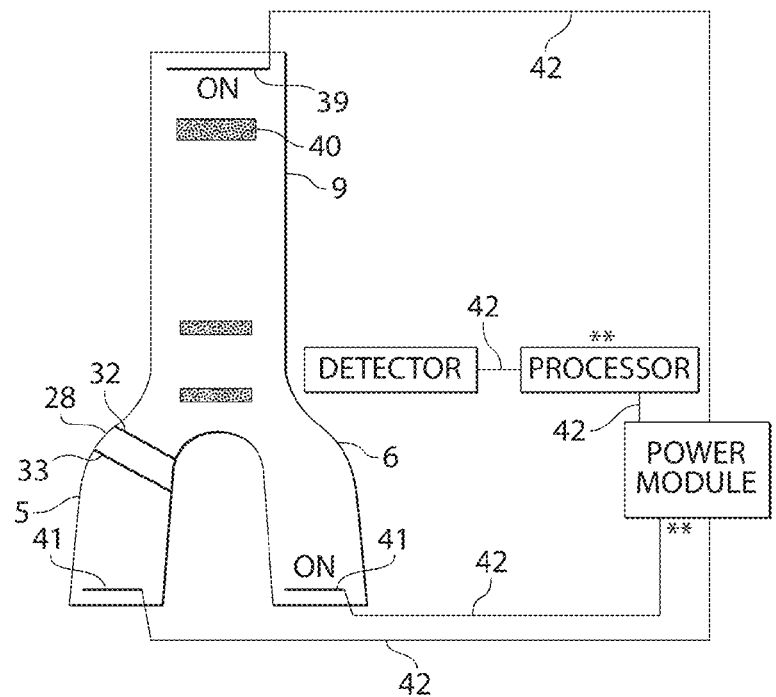
Figure 8D:
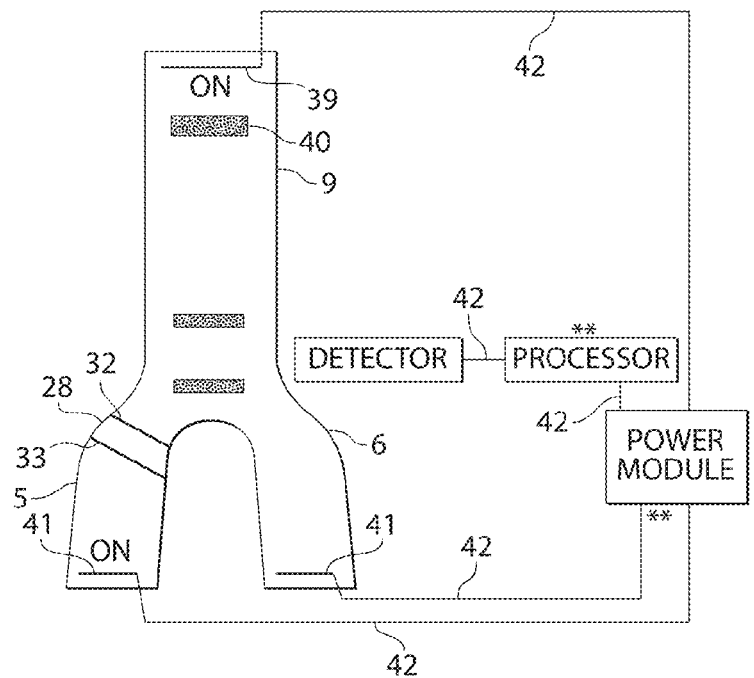
Figure 8E:
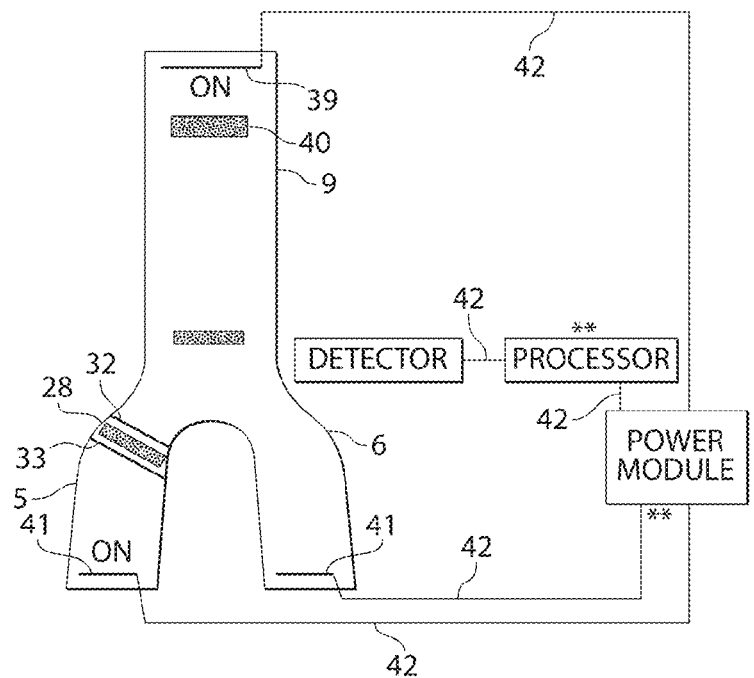
Figure 8F:
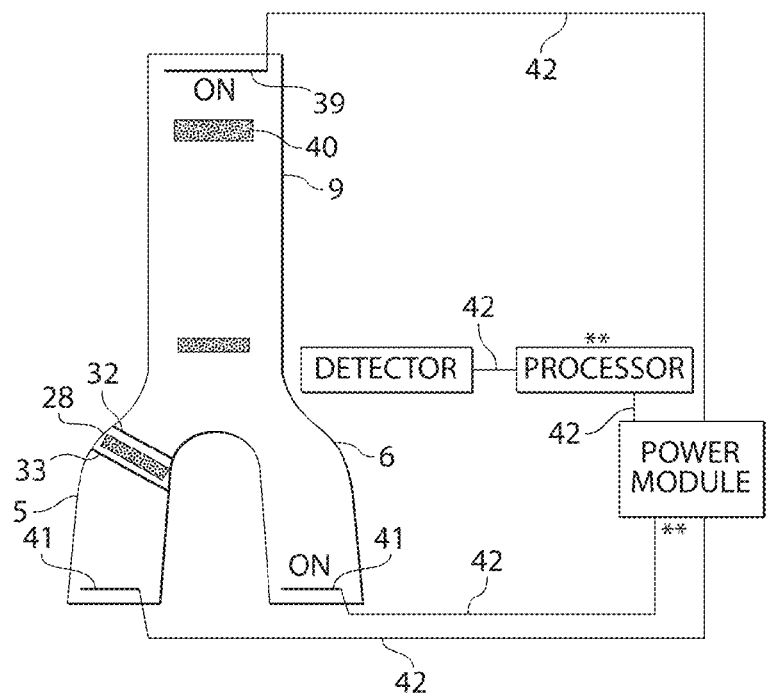
Figure 8G:
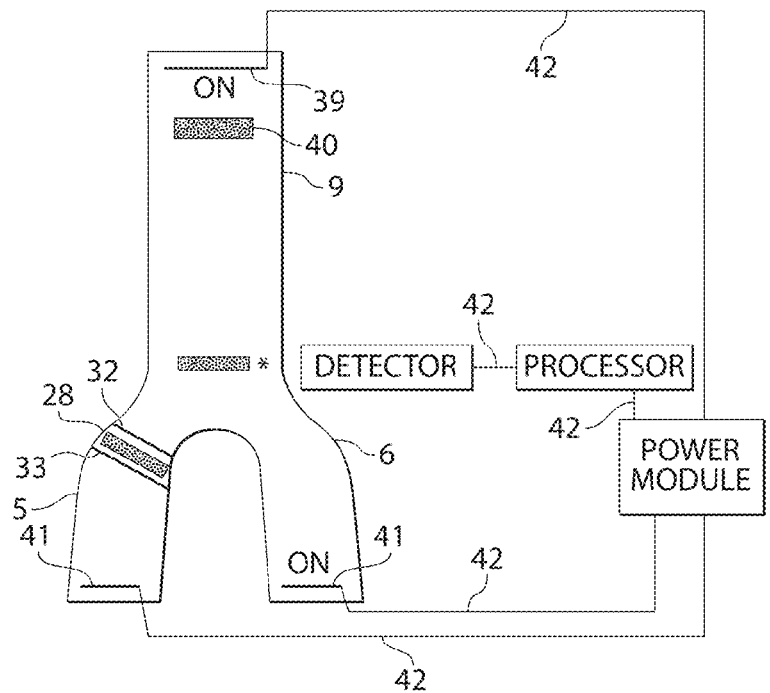
Figure 8H:
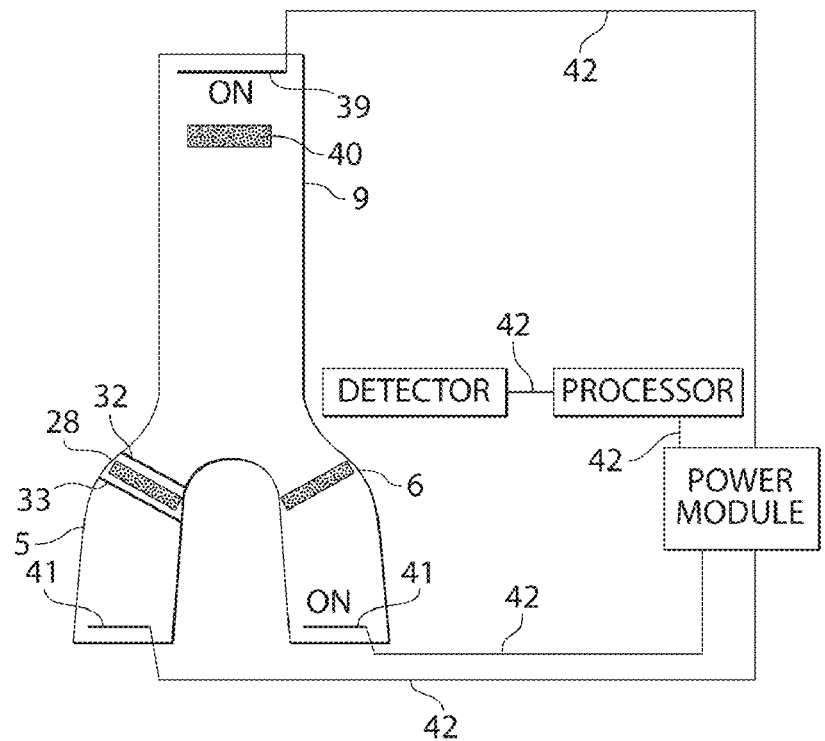
Figure 9:
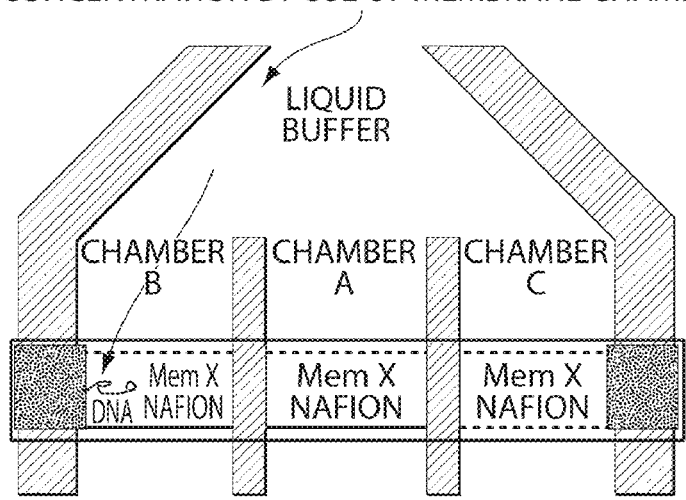
FIG. 9 is an illustration depicting the collection of a DNA fraction within an elution chamber having a DNA permeable membrane, a sample collection chamber for retaining DNA, and a DNA impermeable membrane, such as Nafion, to prevent DNA escape.
Figure 10:
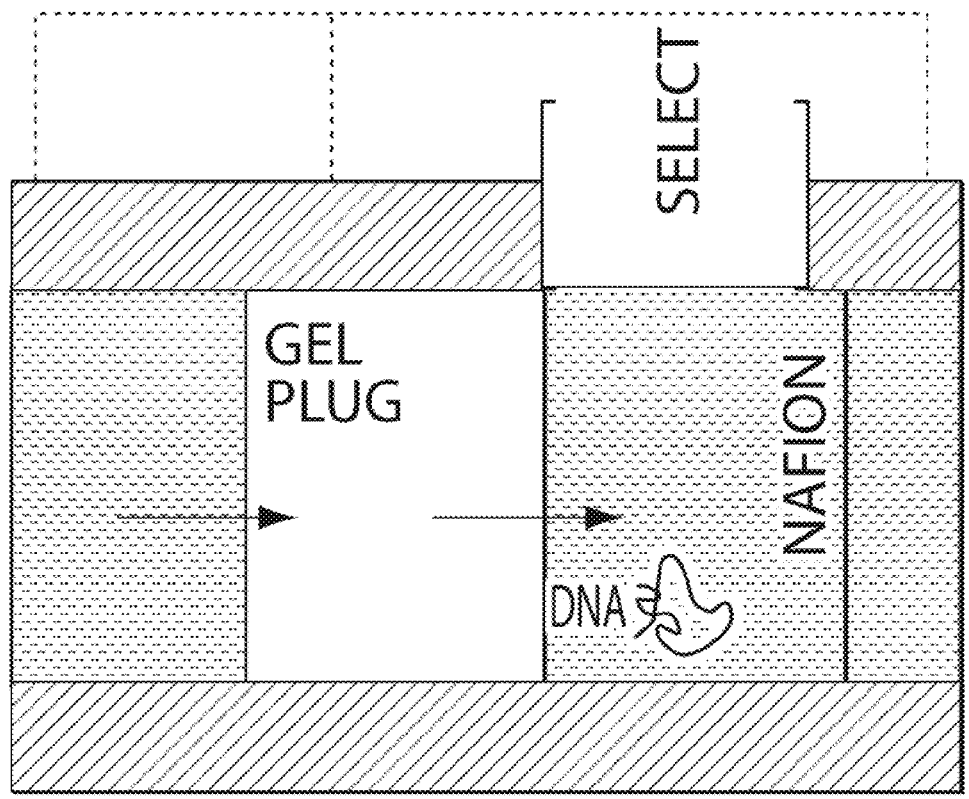
FIG. 10 is an illustration depicting the collection of a DNA fraction within an elution chamber having a gel plug, a buffer-filled sample collection chamber for retaining DNA, and a DNA impermeable membrane, such as Nafion, to prevent escape.
Figure 11:
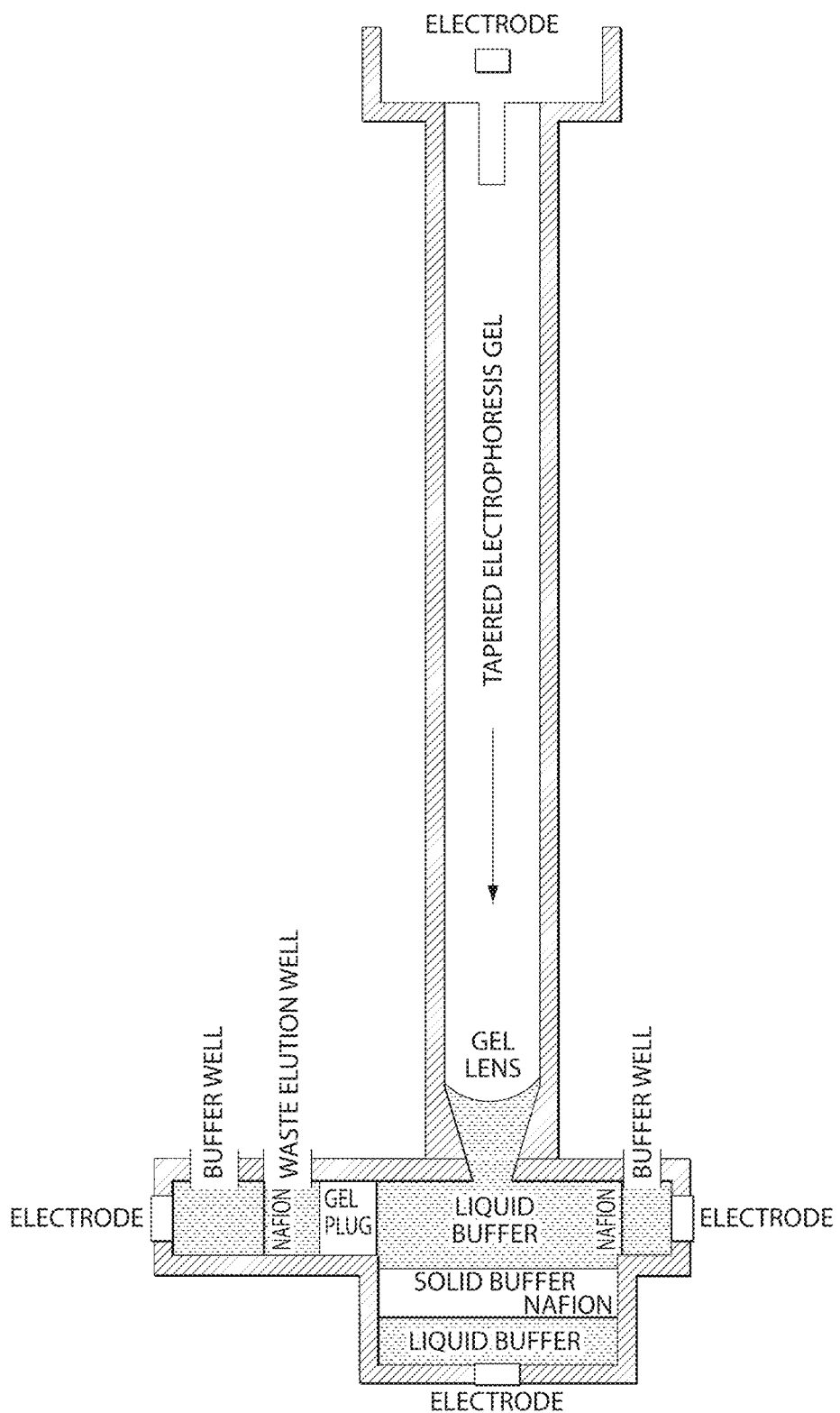
FIG. 11 is a schematic representation depicting an electrophoresis system with a T-shaped elution channel and a gel lens. This electrophoresis system contains an electrode chamber at the T-junction. Fractions are collected unilaterally.
Figure 12:
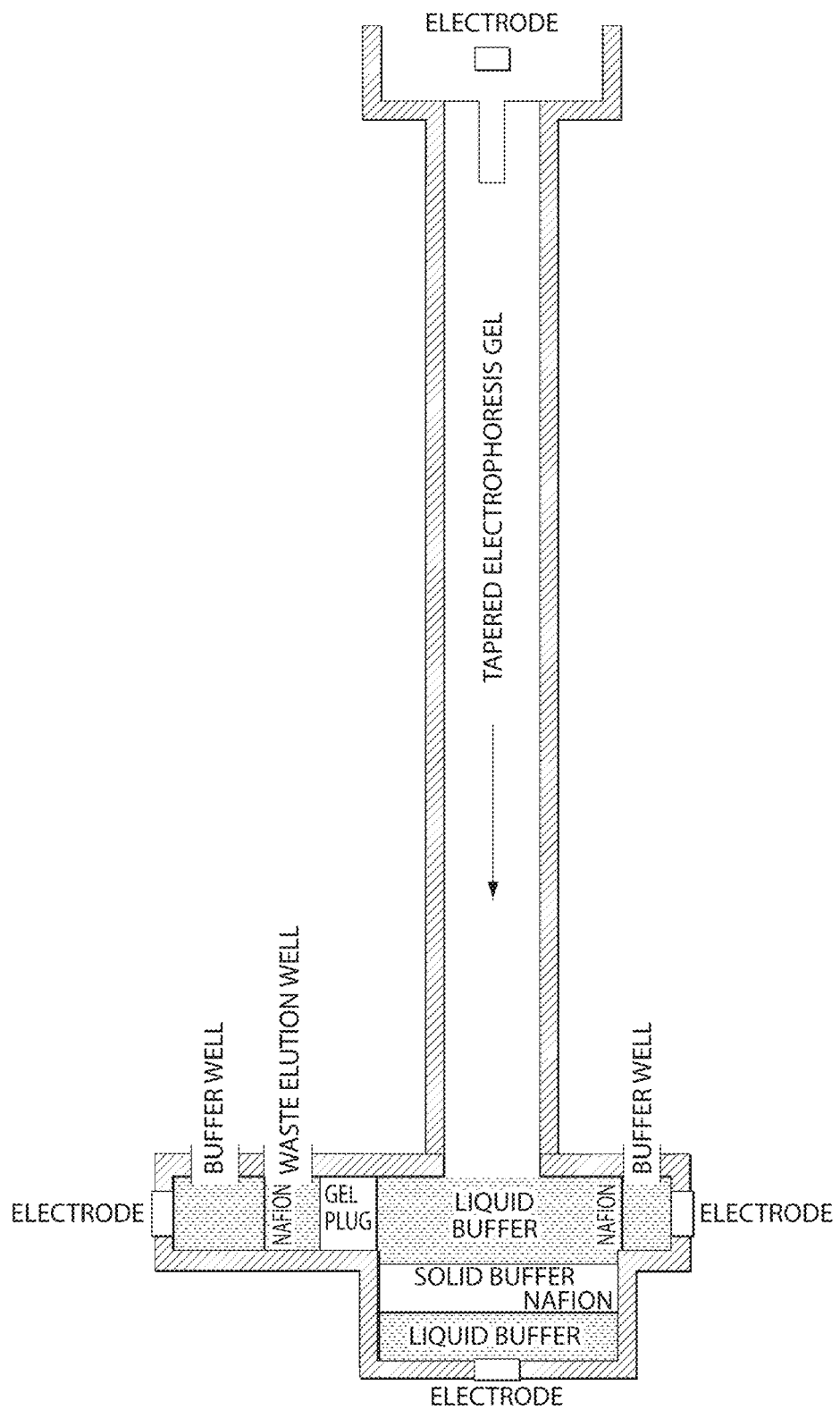
FIG. 12 is a schematic representation depicting an electrophoresis system with a T-shaped elution channel without a gel lens. This electrophoresis system contains an electrode chamber at the T-junction. Fractions are collected unilaterally.
Figure 13:
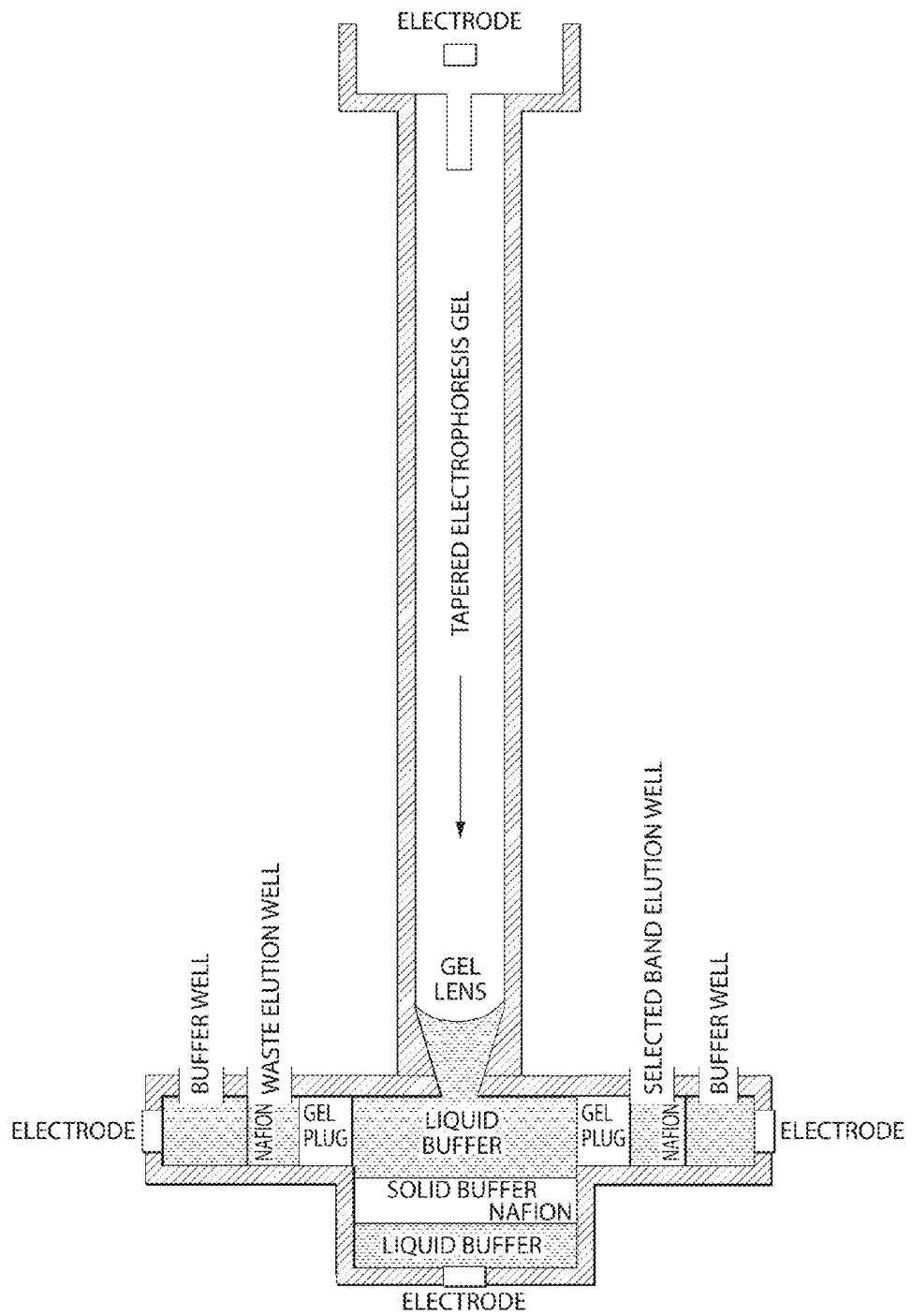
FIG. 13 is a schematic representation depicting an electrophoresis system with a T-shaped elution channel and a gel lens. This electrophoresis system contains an electrode chamber at the T-junction. Desired fractions are differentiated from the remaining sample by directing those fractions to the elution chamber (or selected-band elution well) rather than the waste reservoir (or waste elution well).
Figure 14:
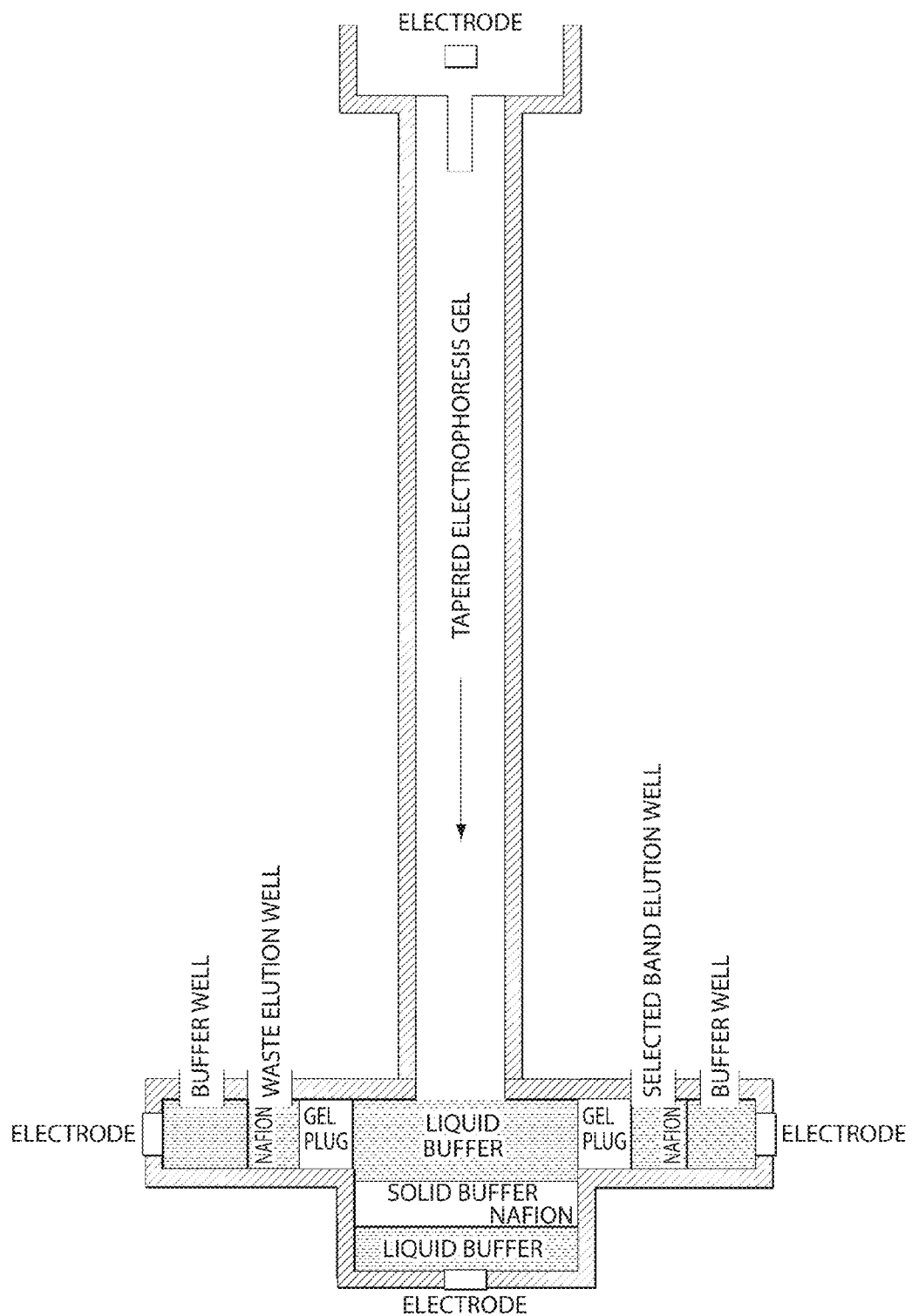
FIG. 14 is a schematic representation depicting an electrophoresis system with a T-shaped elution channel without a gel lens. This electrophoresis system contains an electrode chamber at the T-junction. Desired fractions are differentiated from the remaining sample by directing those fractions to the elution chamber (or selected-band elution well) rather than the waste reservoir (or waste elution well).
Figure 15:
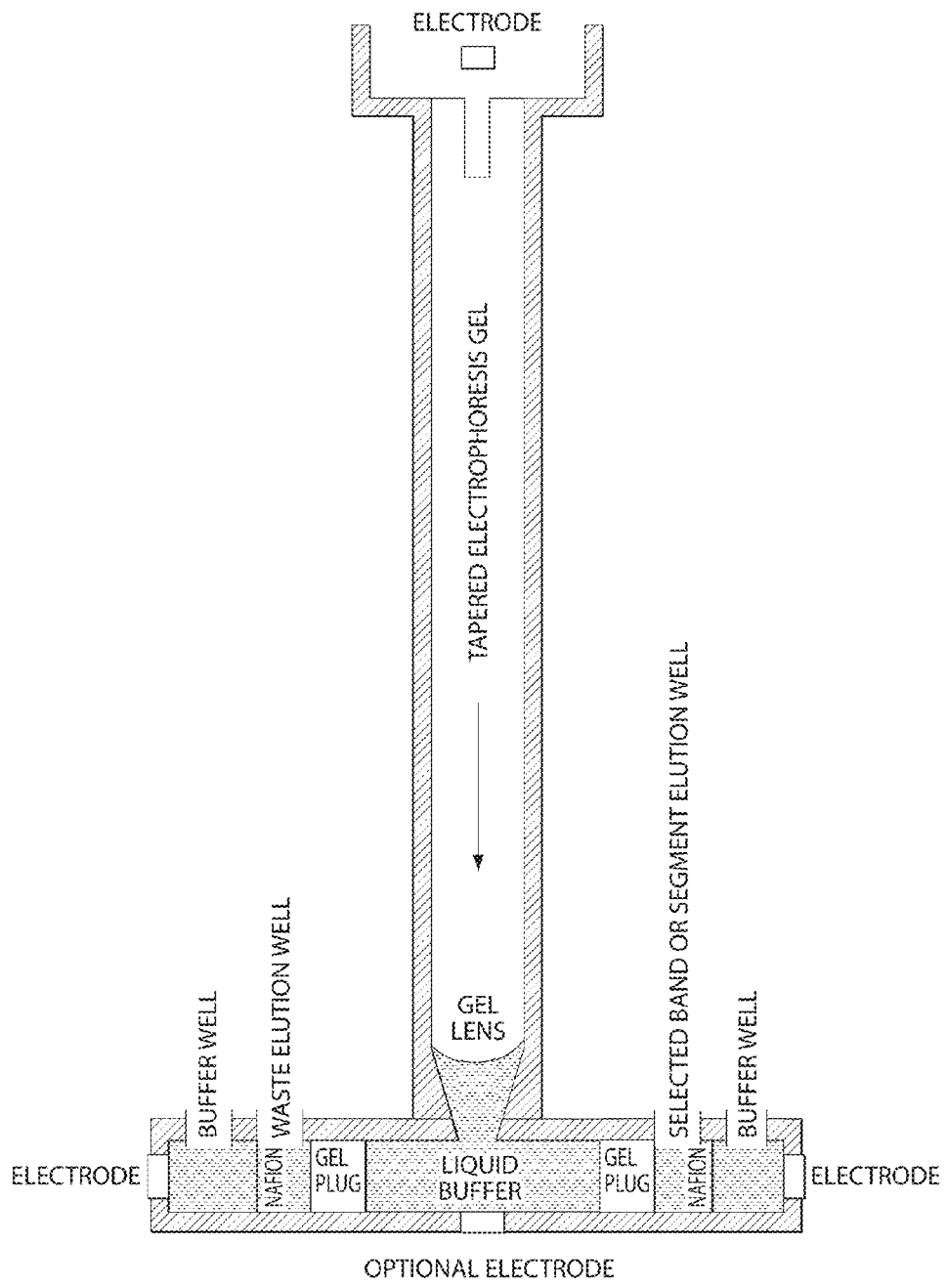
FIG. 15 is a schematic representation depicting an electrophoresis system with a T-shaped elution channel and a gel lens. This electrophoresis system is lacking an electrode module at the T-junction depicted in FIGS. 11-14, and contains an optional electrode in its place. Desired fractions are differentiated from the remaining sample by directing those fractions to the elution chamber (or selected-band elution well) rather than the waste reservoir (or waste elution well).
Figure 16:
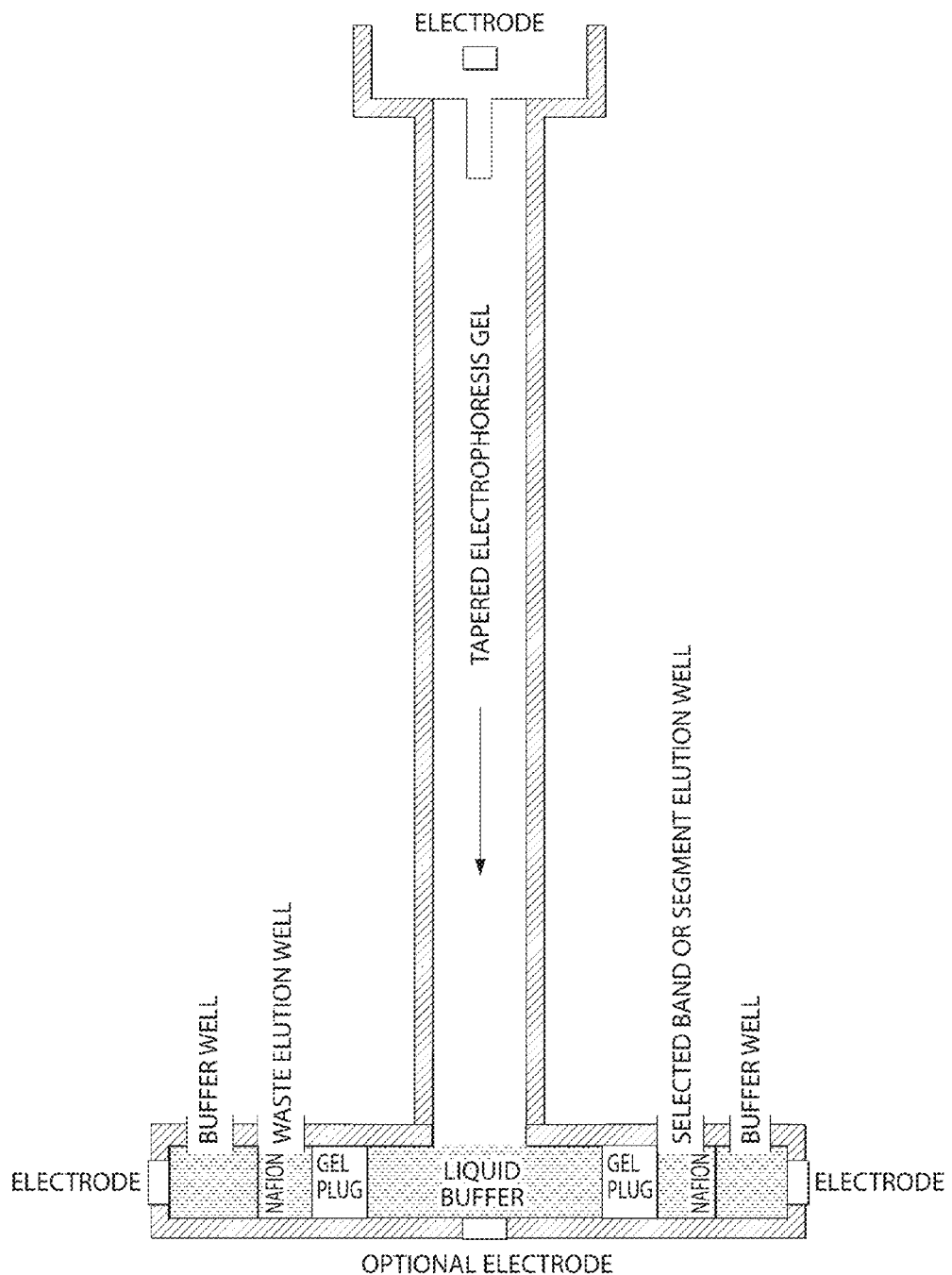
FIG. 16 is a schematic representation depicting an electrophoresis system with a T-shaped elution channel without a gel lens. This electrophoresis system is lacking an electrode module at the T-junction depicted in FIGS. 11-14, and contains an optional electrode in its place. Desired fractions are differentiated from the remaining sample by directing those fractions to the elution chamber (or selected-band elution well) rather than the waste reservoir (or waste elution well).
Figure 17:
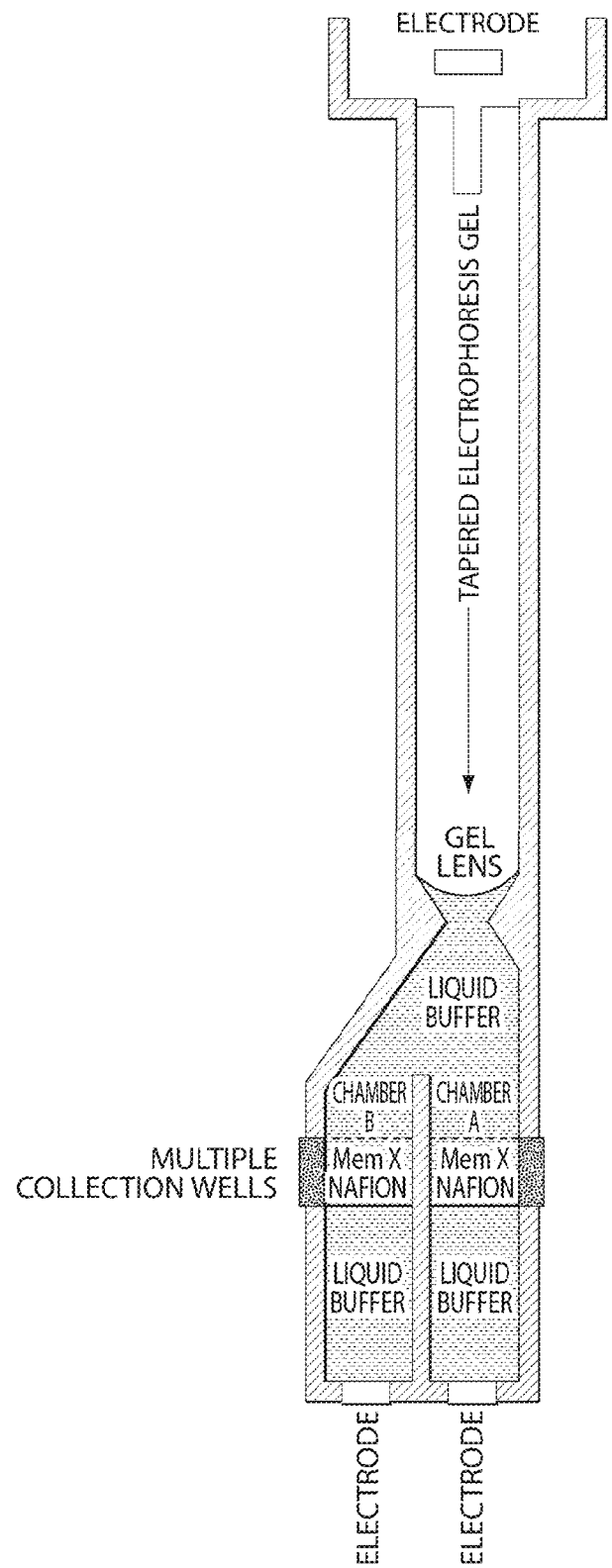
FIG. 17 is a schematic representation depicting an electrophoresis system with asymmetric elution channels and a gel lens. Fractions are captured by using sample collection chambers having differentially permeable membranes on either end. Desired fractions are differentiated from the remaining sample by directing those fractions to elution Chamber A rather than elution Chamber B, or vice versa.
Figure 18:
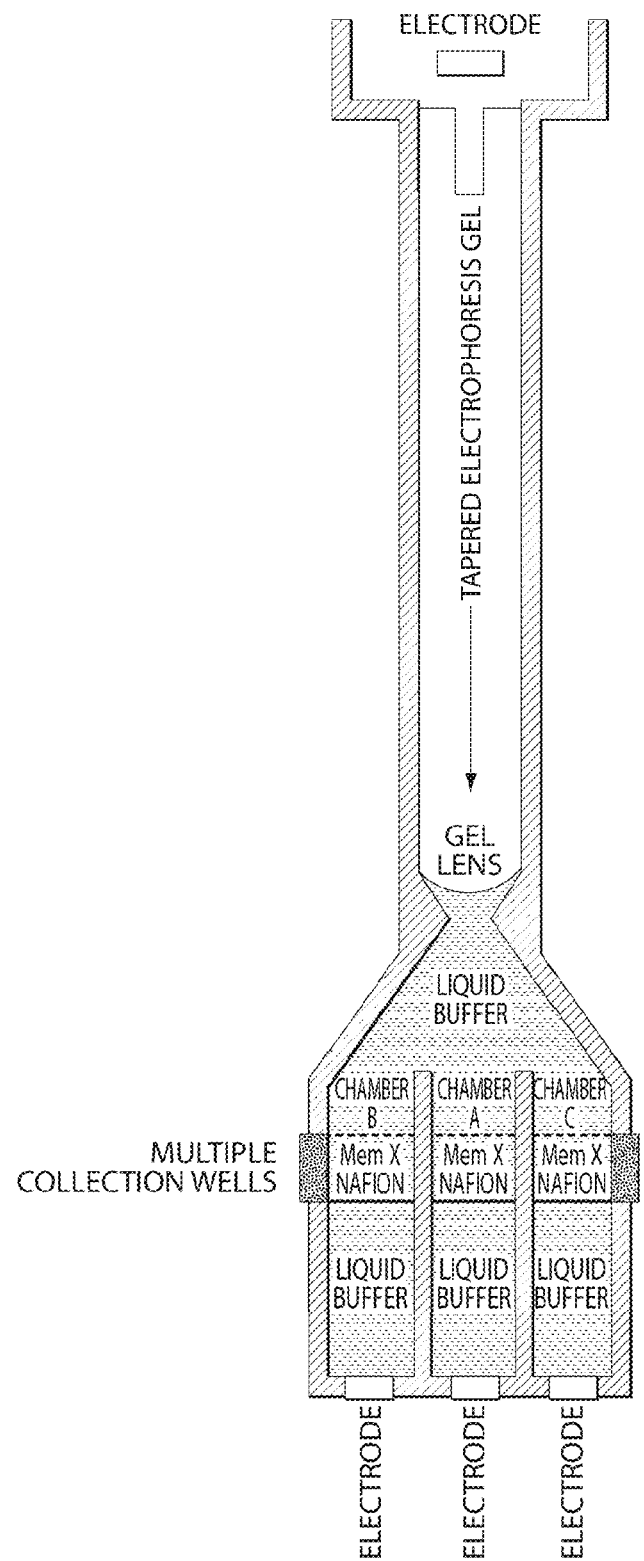
FIG. 18 is a schematic representation depicting an electrophoresis system with asymmetric elution channels and a gel lens. Fractions are captured by using sample collection chambers having differentially permeable membranes on either end. Desired fractions are differentiated from the remaining sample by directing those fractions to one or more designated elution chambers (e.g. Chamber A versus Chamber B or C). Although three elution chambers are depicted, the illustrated electrophoresis system can contain multiple channels of any number. Preferred embodiments contain up to 13 channels for sample or fraction collection.
Figure 19:
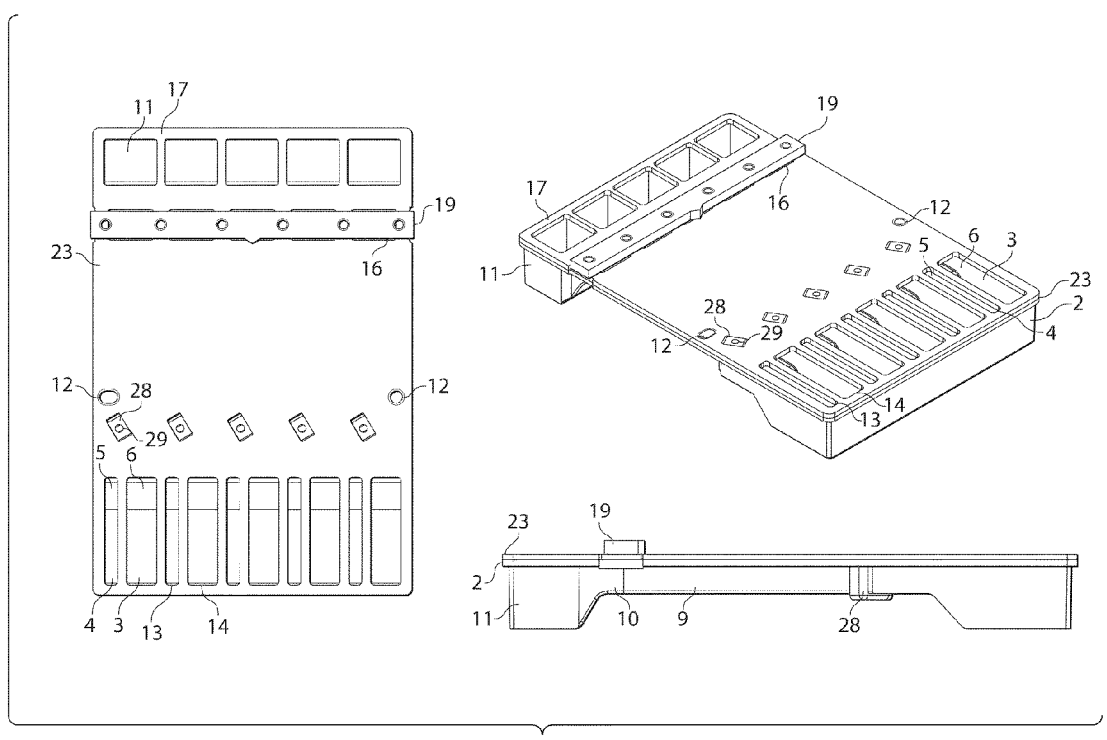
FIG. 19 is series of schematics of a multichannel preparative electrophoresis cassette, having 5 macrofluidic channels. The channel plate is contacted to the cover plate and the sample well insert traverses the sample well insert opening of the cover plate. Three perspectives are shown.
Figure 20:
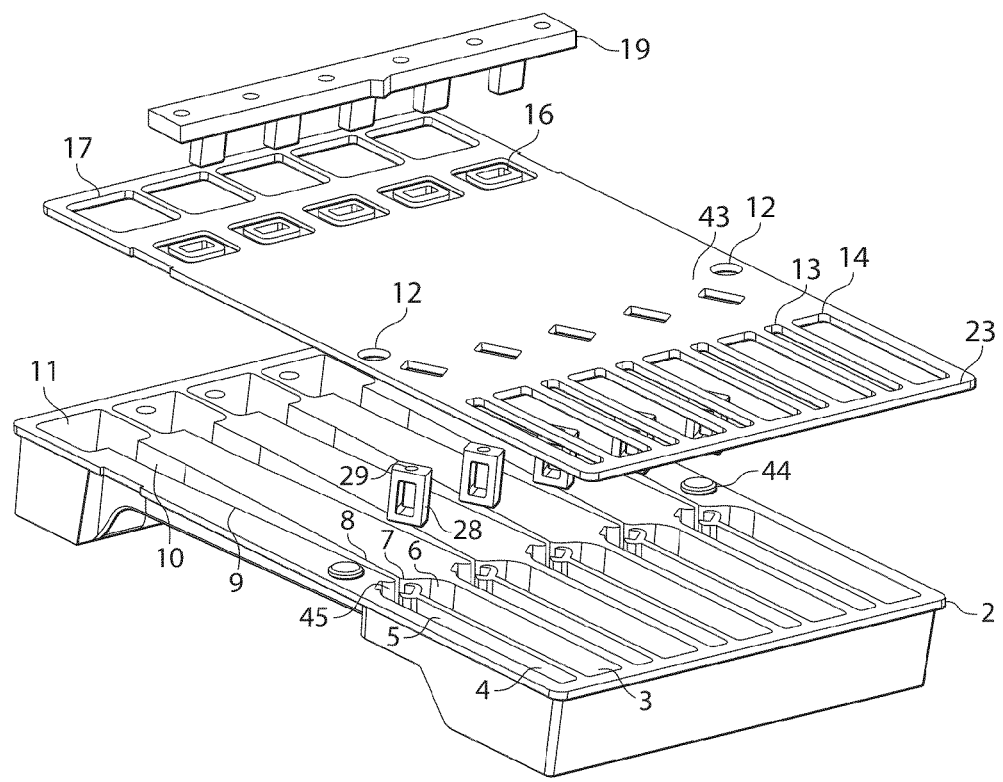
FIG. 20 is a blow-up schematic of the multichannel preparative electrophoresis cassette of FIG. 19. The channel plate, elution chambers, cover plate, and sample well insert are detached to reveal detail.
Figure 21:
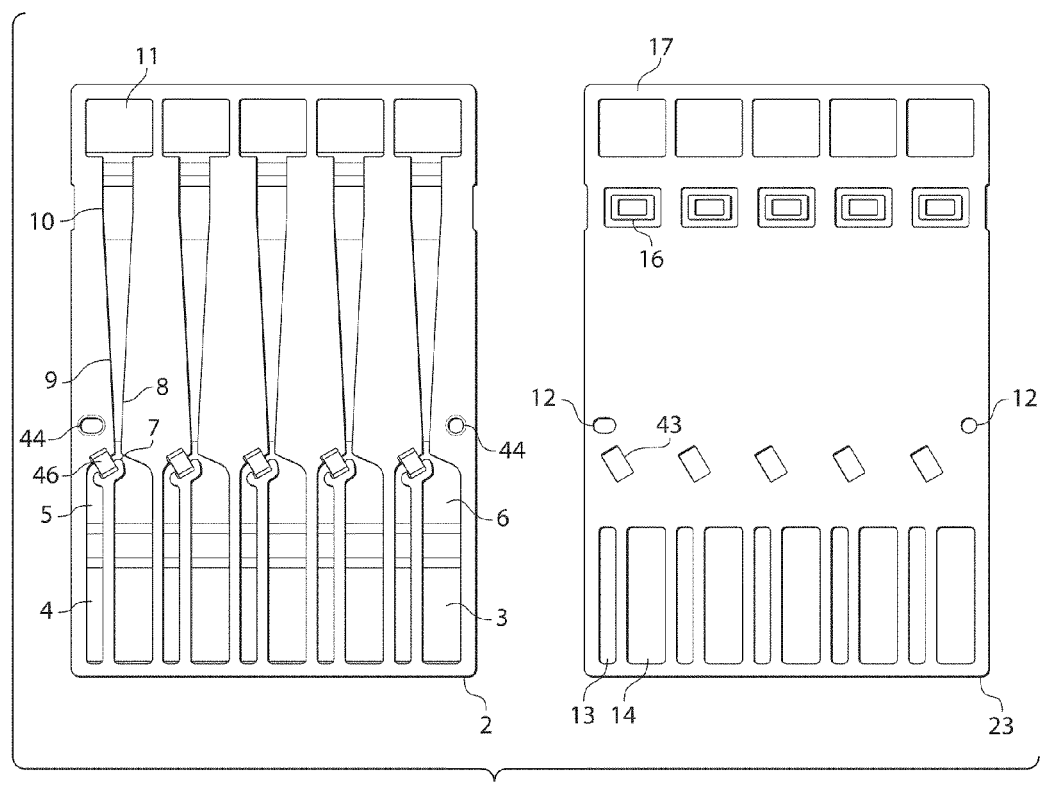
FIG. 21 is a series of schematics of a multichannel preparative electrophoresis cassette, having 5 macrofluidic channels. Left Panel: The channel plate shows 5 tapered macrofluidic separation channels each having an elution chamber. Right Panel: The cover plate with a configuration of that corresponds to the channel plate.
Figure 22:
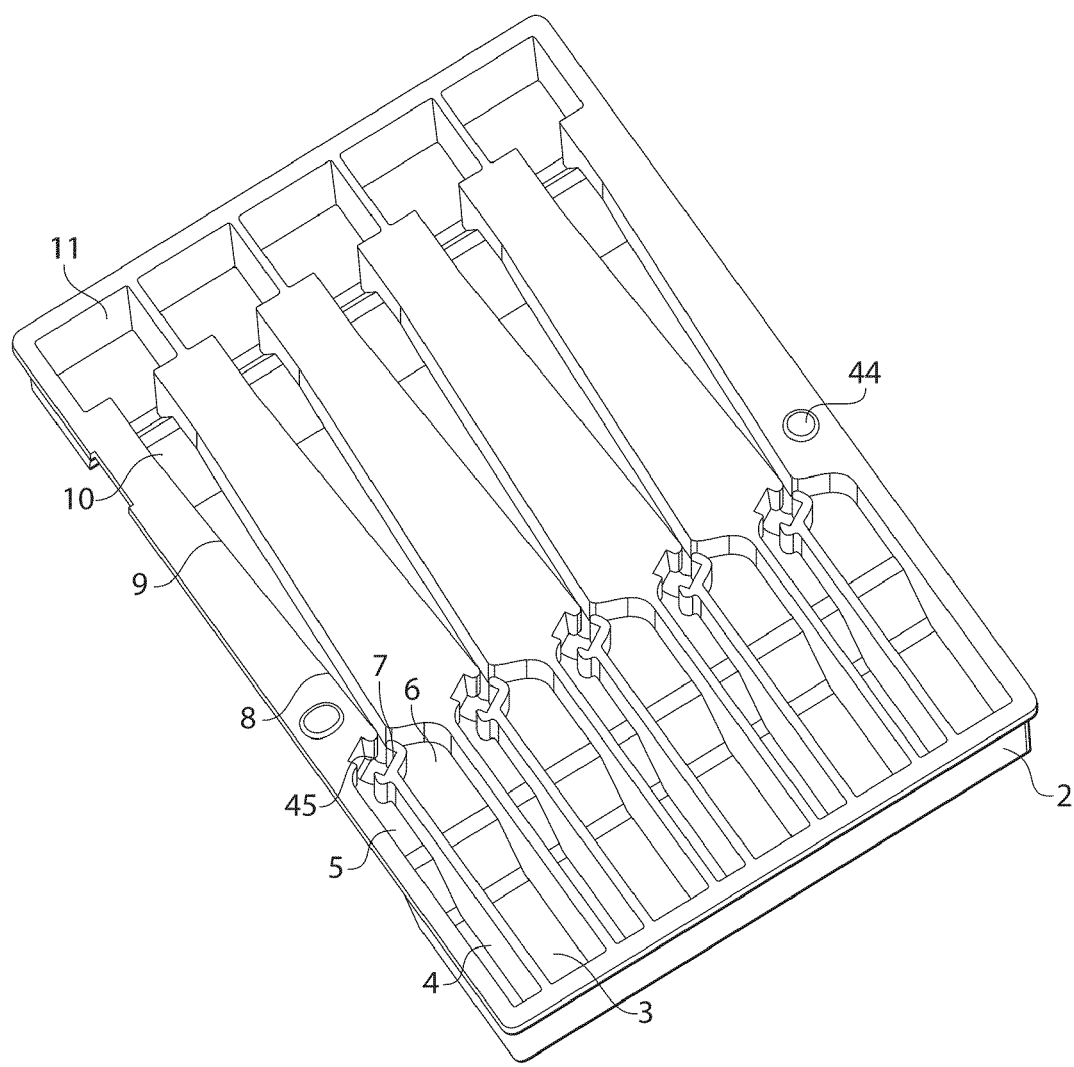
FIG. 22 is a schematic of a multichannel preparative electrophoresis cassette, having 5 macrofluidic channels. The channel plate shows 5 tapered macrofluidic separation channels each having an elution chamber cavity for housing an elution chamber.
Figure 23:
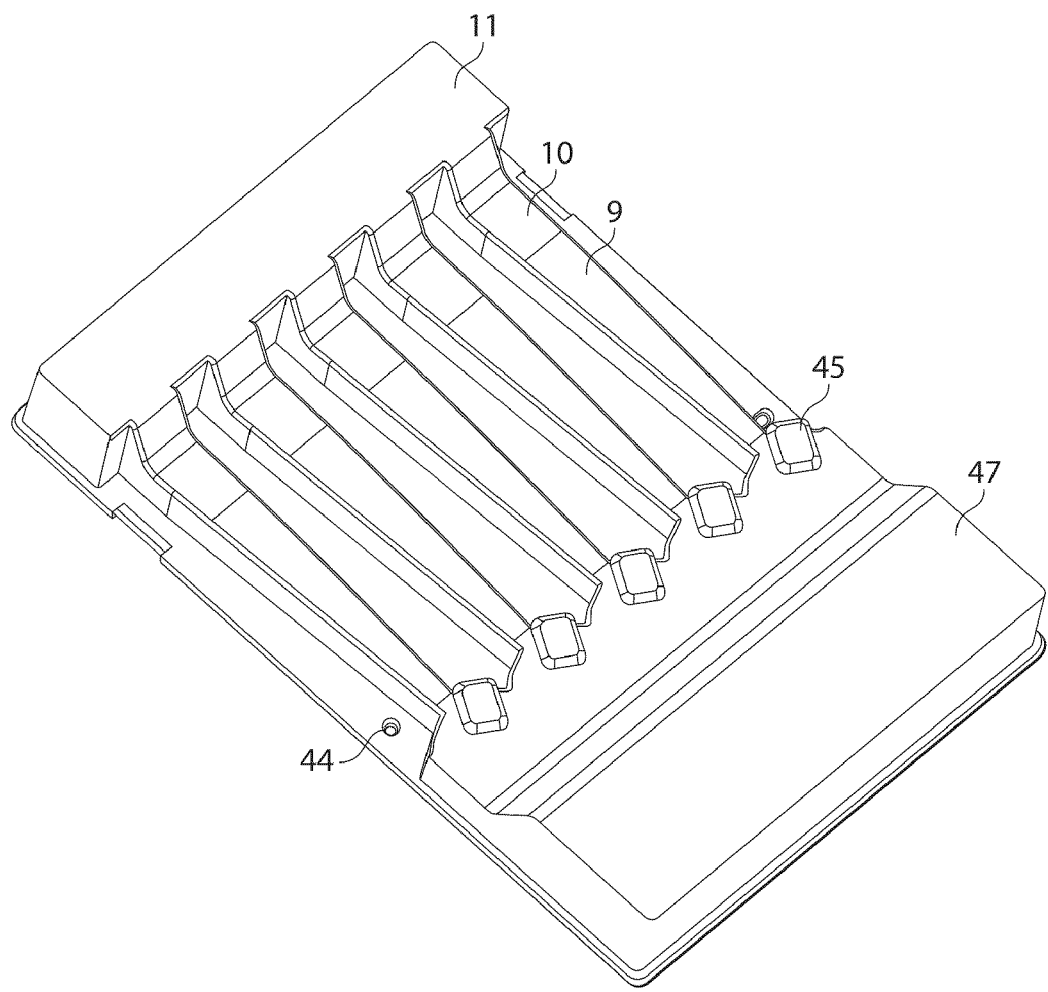
FIG. 23 is a schematic of the underside of the multichannel preparative electrophoresis cassette of FIG. 22.
Figure 24:
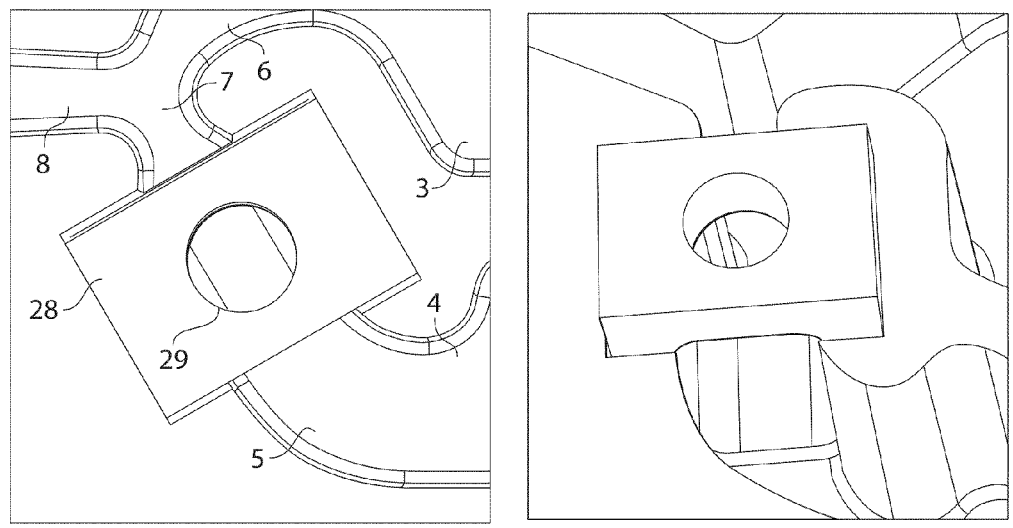
FIG. 24 is a series of schematics of an elution chamber having a sample collection chamber and a sample collection port in two perspectives.
Figure 25:
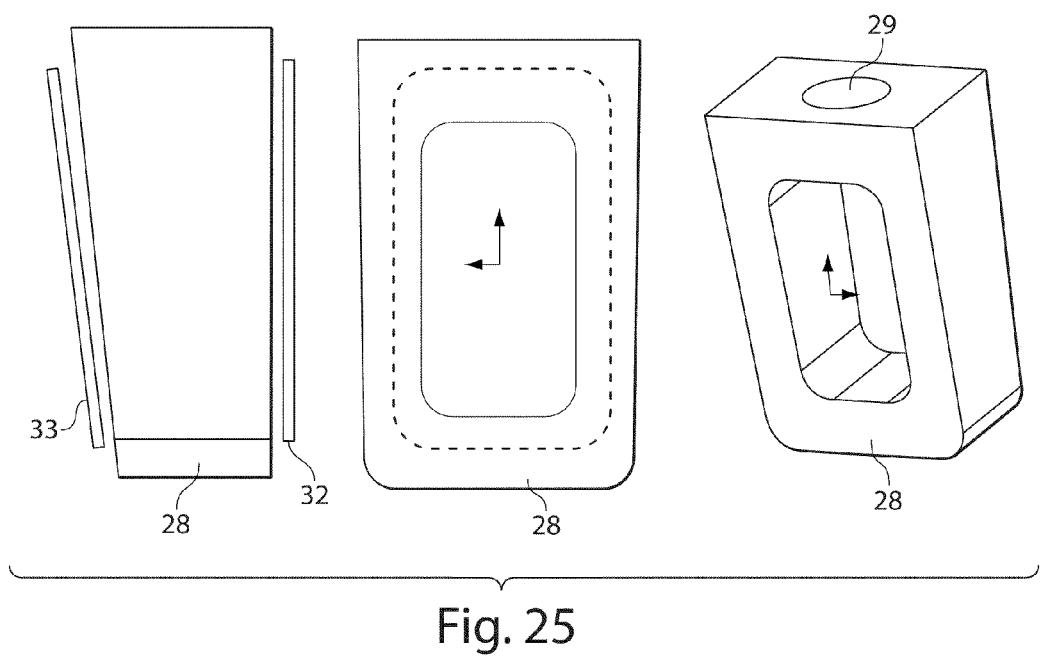
FIG. 25 is a series of schematics of an elution chamber having, with respect to the direction of electrophoresis, an analyte-permeable barrier, a sample-collection chamber, and an analyte-impermeable barrier. The sample collection chamber further contains a sample-collection port.
Figure 26:
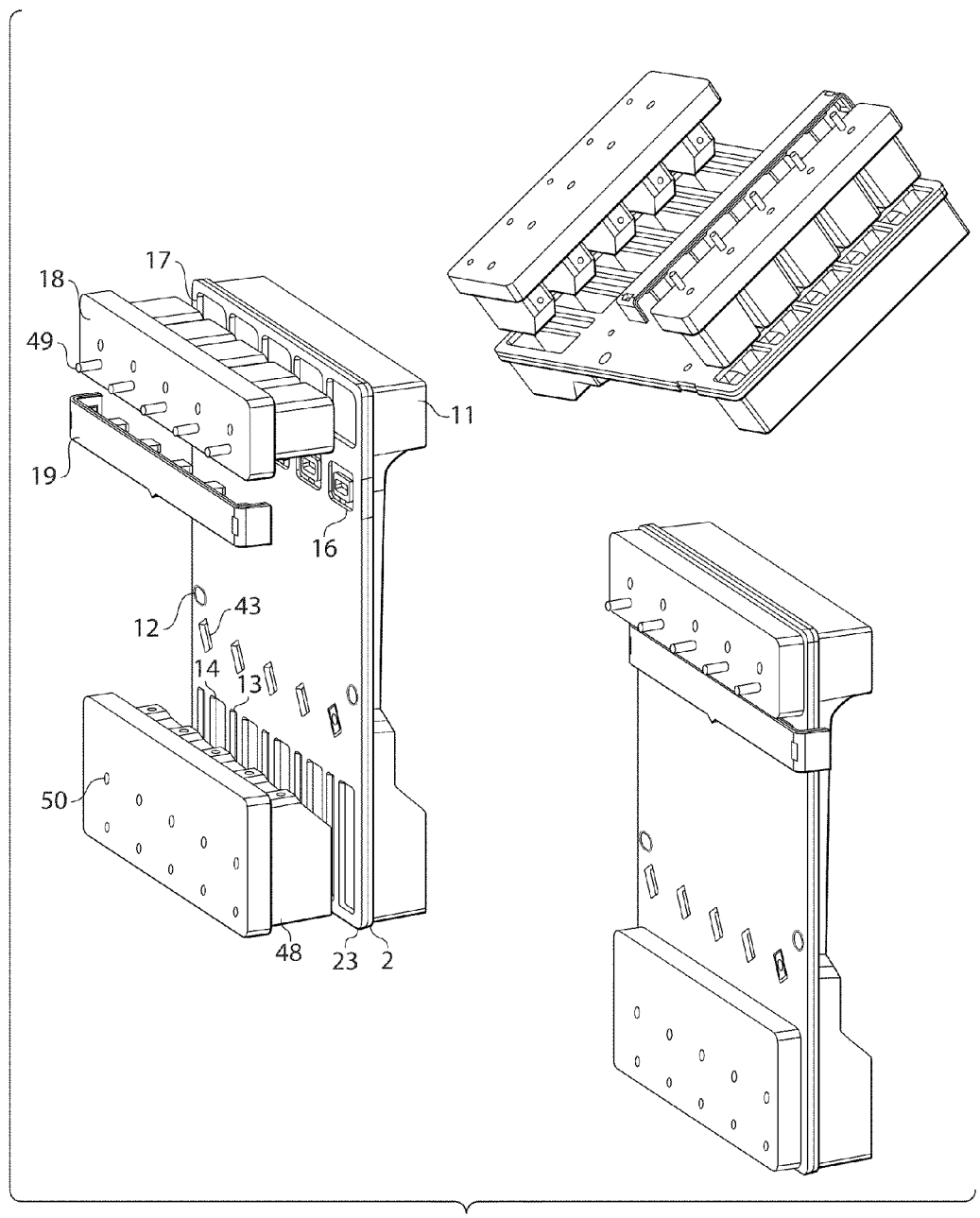
FIG. 26 is a series of schematics of an electrophoresis cassette contacted with a cover plate, wherein a buffer reservoir insert, a sample well insert, and a waste reservoir insert traverse the cover plate. Exemplary buffer reservoir inserts contain a vent. Furthermore, exemplary waste reservoir inserts contain at least one injection port. Three-perspectives are given of these components assembled and disassembled to show detail. Gels are caste by inserting a liquid gel matrix into the injection port and allowing the gel to harden into a solid form. Inserts are then removed and the resultant buffer reservoir, sample well, elution reservoir, and waste reservoir are filled with a buffer composition.
Figure 27:
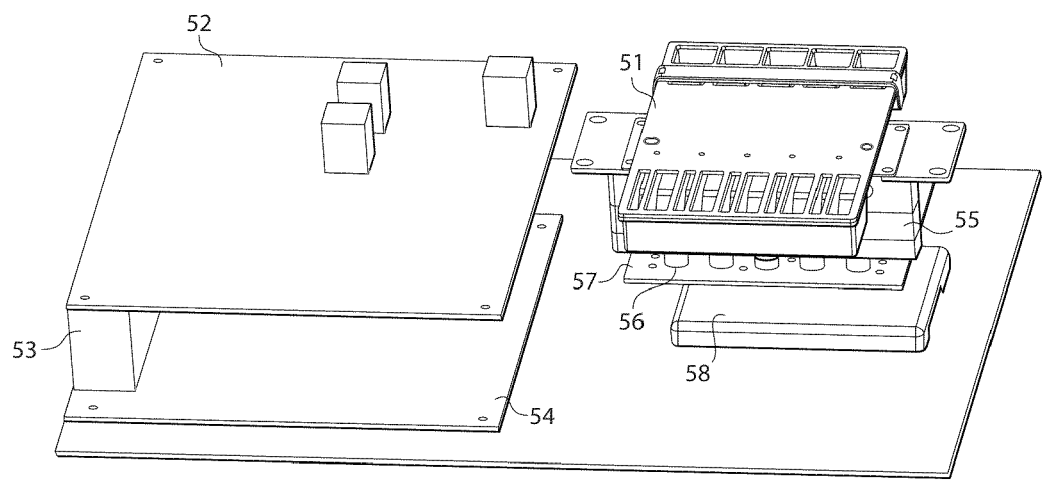
FIG. 27 is a schematic of an "uncovered" detection system, depicting an electophoresis cassette placed over light-emitting diodes and an optics housing, surrounded by the processor elements that signal detection and selective activation/deactivation of the electrode array.
Figure 28:
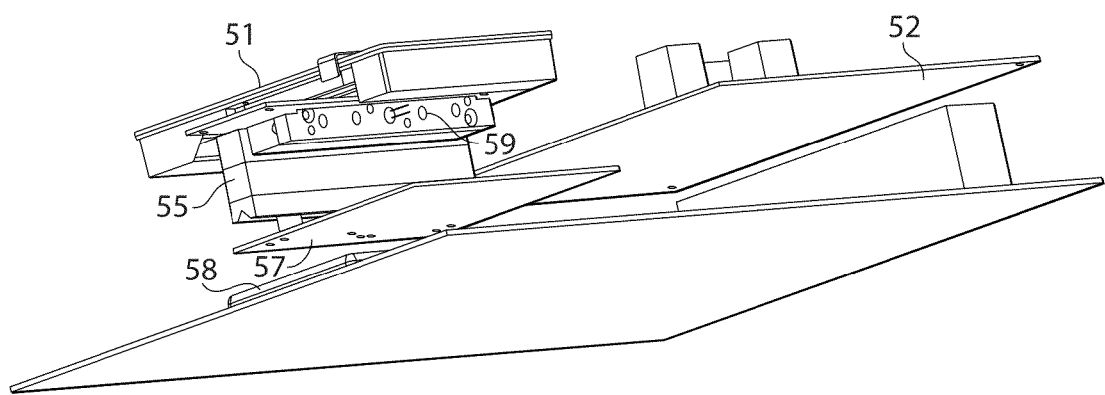
FIG. 28 is a schematic of the "uncovered" detection system of FIG. 27 from an alternative perspective.
Figure 29:
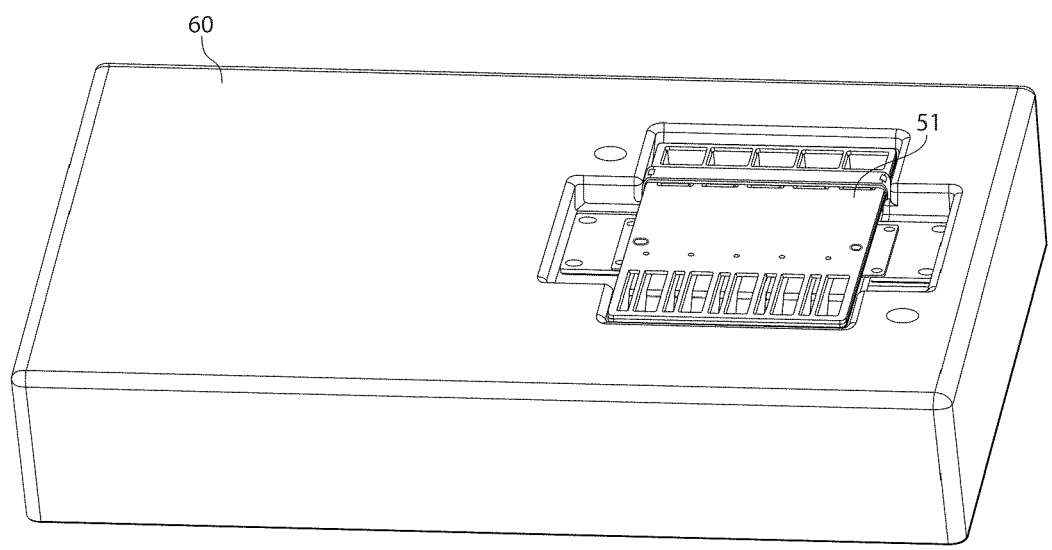
FIG. 29 is a schematic of the "covered" detection system of FIG. 27.
Figure 30:
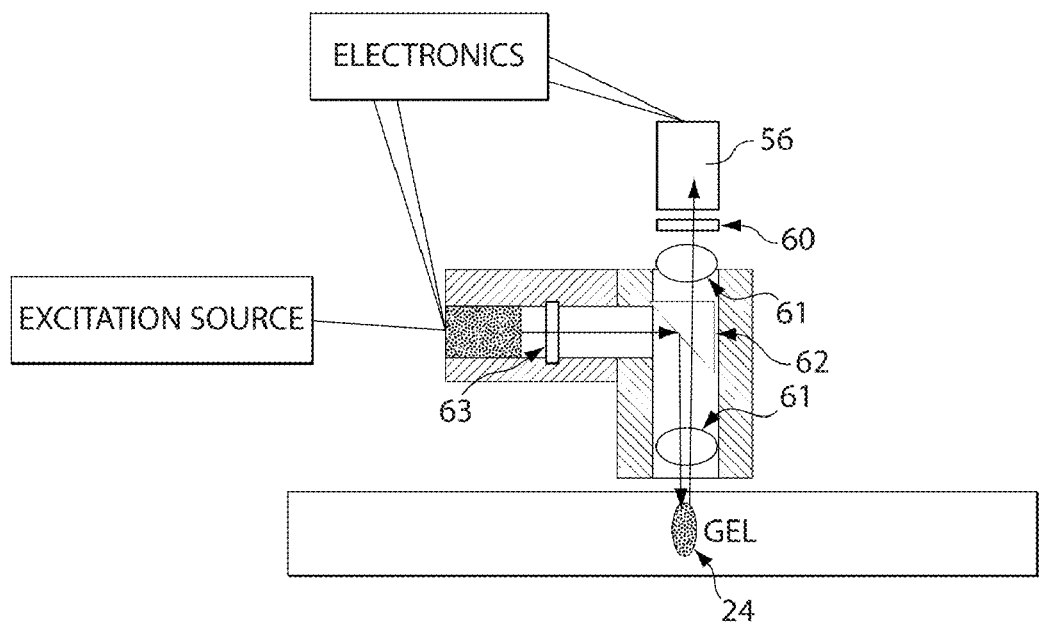
FIG. 30 is an illustration of the optical system of an exemplary electrophoresis system.
Figure 31:
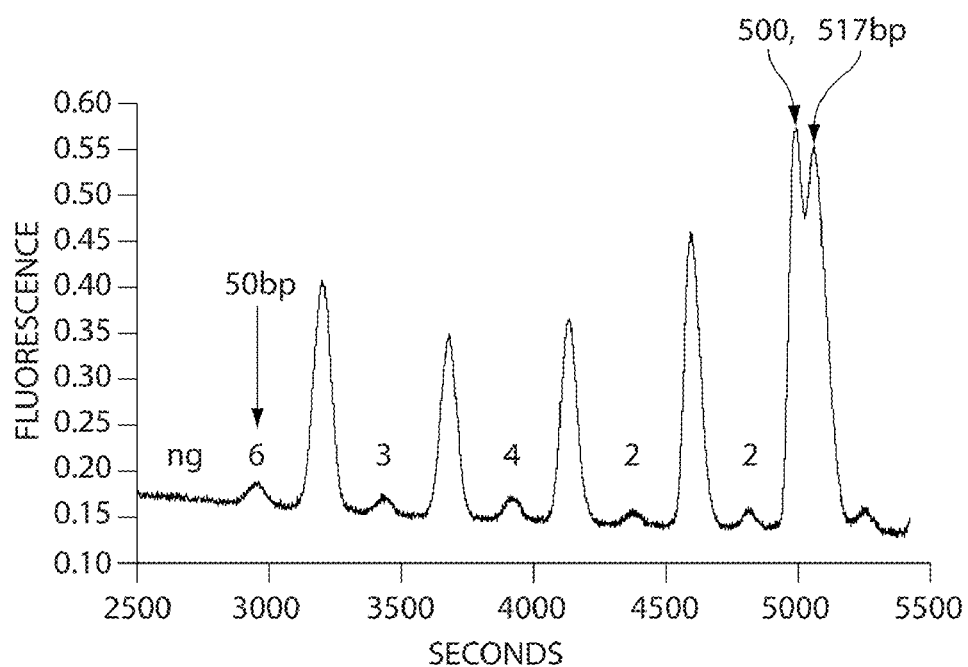
FIG. 31 is a graph of the fluorescence over time of mixed 50 and 100 bp ladders detected using the system of FIG. 31, demonstrating the sensitivity of detection at a concentration of 1 ng per fraction, or band, within the separation channel.
Figure 32:
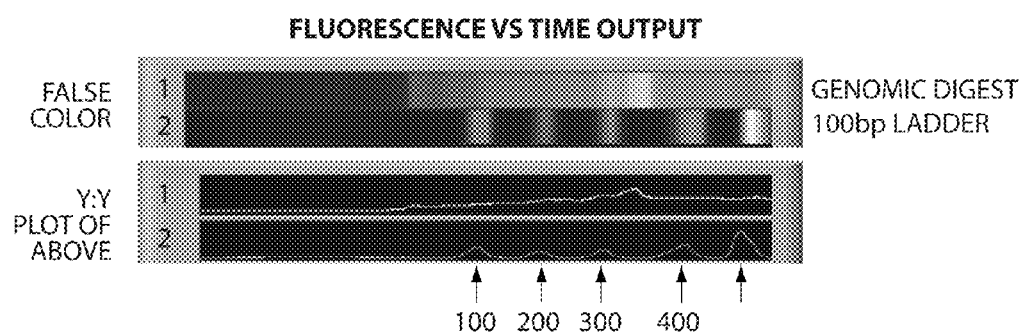
FIG. 32 is a series of graphs depicting the fluorescence versus time signal of digested genomic DNA compared to a 100 bp DNA ladder. These graphs show the real-time optical detection to control DNA purification.
Figure 33:
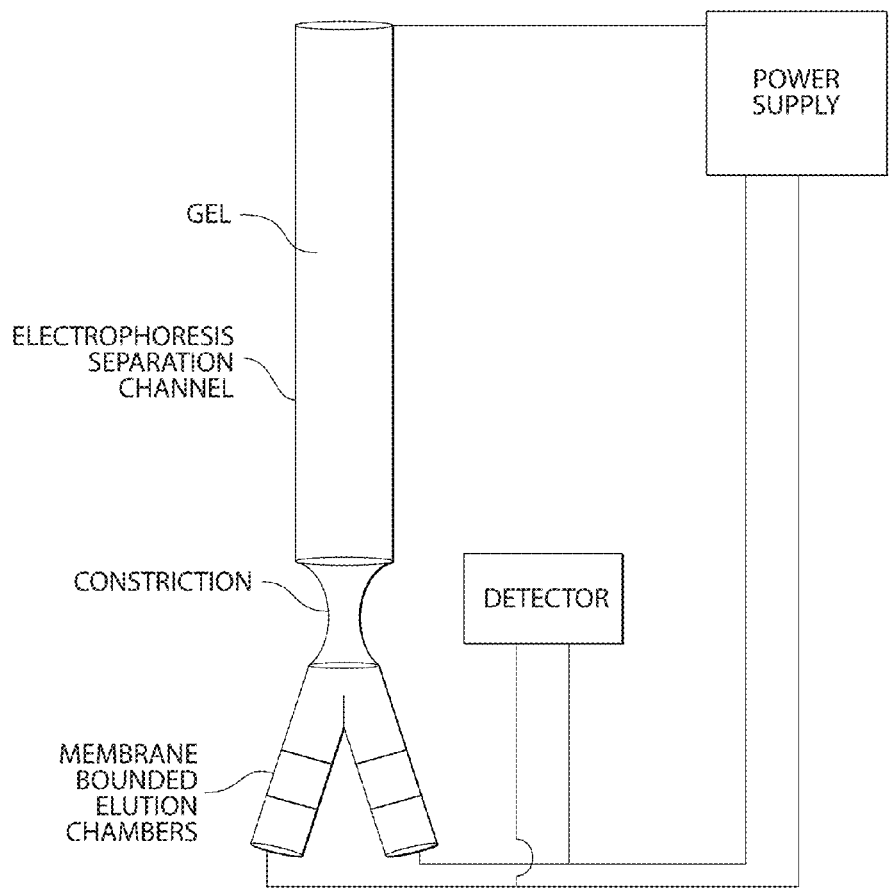
FIG. 33 is a schematic diagram of an exemplary basic electrophoresis system.

The purified sample (50 ul) was withdrawn from the elution chamber with a handheld micropipette DNA from the gel of the waste channel was extracted using a commercial kit (Qiagen QIAquick Gel Extraction kit) and eluted in 50 ul of 10 mM Tris-HCl buffer. Input DNA (1 ug of 100 bp DNA ladder, NEB) was diluted to 50 ul in TE buffer. All three samples were mixed with 10 ul of 40% sucrose in TE buffer containing a small amount of bromophenol blue loading dye and loaded on a 5% acrylamide gel (29:1, mon:bis, 0.5×KBB buffer) for analysis. The image of the ethidium-stained gel is shown in FIG. 6G. There is some distortion of the bands due to the extremely large sample volume (60 ul for all samples), and differences in salt: waste channel DNA and input ladder DNA was dissolved in 10 mM Tris-HCl, whereas purified DNA was loaded in electrophoresis buffer from elution chamber. However, the results show that the targeted 200 bp band was efficiently removed from the input sample (see absence of 200 bp band in waste channel DNA) and efficiently recovered from the elution chamber.

Example 4

Multichannel Cassettes for Automated Preparative Electrophoresis

In some embodiments of the invention, multichannel cassettes are used. Exemplary multichannel cassettes are shown in FIGS. 7, 19, 20, 21, 22, 23, 26, 28, 29, 30, and 31. Multichannel cassettes rapidly process multiple samples. Moreover, multichannel cassettes provide a means by which the molecular weight of an uncharacterized sample in a first macrofluidic channel of the cassette can be estimated by comparison with molecular weight markers run in a second macrofluidic channel of the same cassette.

Example 5

Casting Multichannel Cassettes

The macrofluidic separation channel, including the first and second physically and electrically separated ends, to the proximal sides of the elution chamber (up to the face of the permeable membrane) and the waste reservoir, respectively, are filled with agarose gel. To cast the gel, in accordance with FIG. 26, the channel plate is contacted with the cover plate, and a waste reservoir insert is inserted into the corresponding opening in the cover plate, a sample well insert is inserted into the corresponding opening in the cover, and a buffer reservoir insert is inserted into the corresponding opening in the cover plate. The buffer insert contains a vent and the waste insert contains an injection port. The inserts are designed to seal tightly against the cover plate to prevent leakage of the molten agarose solution. Molten agarose is injected into each channel through ports that extend through the waste reservoir insert and open into the bottom end of the second physically and electrically isolated portion of the separation channel. Molten agarose mixture is injected from syringes or automated liquid dispensing instruments through the injection port into the second physically and electrically isolated portion of the separation channel. During casting of the gel, the cassette is held in a vertical position (proximal end up), thereby filling the separation channel and the proximal regions of the first and second physically and electrically isolated portions from the bottom up. In the first physically and electrically isolated portion of the separation channel, the molten gel fills the space extending from the division point to the proximal side of the elution chamber. Care is maintained to avoid trapping air bubbles at any point. The injection and vent ports completely occupy the volume of the waste and buffer reservoirs, thereby precisely determining the boundaries of the gel column on either end, where the gel meets the ports.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. An electrophoresis cassette comprising:
a plate including at least one macrofluidic separation channel, the channel having a first physically and electrically isolated portion and a second physically and electrically isolated portion;
a constriction point provided between the separation channel and at least one of the first and second physically and electrically isolated portions; and
an elution chamber positioned on one or another of the physically and electrically isolated portions, the chamber comprising at least one of an elution cavity and an analyte-impermeable barrier.

2. The cassette of claim 1, wherein the elution chamber further comprises at least one of an analyte-permeable barrier, a sample collection chamber including a sample removal port, and an analyte-impermeable barrier.

3. The cassette of claim 1, further comprising a buffer reservoir for each of the macrofluidic separation channels.

4. The cassette of claim 1, further comprising a cover for the plate.

5. The cassette of claim 3, further comprising at least one of a sample well cavity, an elution reservoir and a waste reservoir.

6. The cassette of claim 5, further comprising a division point provided between the macrofluidic channel and the elution reservoir and the waste reservoir.

7. The cassette of claim 5, wherein the elution reservoir and the waste reservoir are provided at an end of the first physically and electrically isolated portions and the second physically and electrically isolated portions, respectively.

8. The cassette of claim 1, further comprising a cover for the plate, wherein the cover includes a configuration that corresponds to the configuration of the top of the plate.

9. The cassette of claim 3, further comprising a cover for the plate, wherein the cover includes at least one of an opening, a protrusion and a recess that align with at least one of the buffer reservoirs.

10. The cassette of claim 5, further comprising a cover for the plate, wherein the cover includes at least one of an opening, a protrusion and a recess that align with at least one of the macrofluidic channel, the buffer reservoir, the sample well cavity, the sample removal port, the elution reservoir, the waste reservoir, and the first and second physically and electrically isolated portions.

11. The cassette of claim 1, wherein the separation channel is tapered from one end to the constriction point.

12. The cassette of claim 6, wherein the constriction point is the division point.

13. The cassette of claim 1, wherein the cassette is disposable.

14. The cassette of claim 5, wherein the cassette further comprises:
a negative electrode positioned between the buffer reservoir and a corresponding end of the separation channel;
a positive electrode positioned between an end of the first physically and electrically isolated portion and the elution reservoir; and
a positive electrode positioned between an end of the second physically and electrically isolated portion and the waste reservoir.

15. The cassette of claim 1, wherein the microfluidic channel includes at least one of a gel matrix composition, a liquid buffer composition, a solid buffer composition.

16. The cassette of claim 15, wherein at least one of a gel matrix composition, a liquid buffer composition, a solid buffer composition comprises at least one of a fluorophore or a chromophore.

17. The cassette of claim 6, wherein at least one macrofluidic separation channel further comprises a gel matrix composition.

18. The cassette of claim 17, wherein the gel matrix composition fills a volume of the macrofluidic separation channel, including at least one of the first and second physically and electrically isolated portions.

19. The cassette of claim 17, wherein the gel matrix composition defines at least one sample well within at least one sample well cavity.

20. The cassette of claim 17, wherein at least one macrofluidic channel further comprises a buffer composition.

21. The cassette of claim 20, wherein the buffer composition fills a volume of at least one buffer reservoir, at least one sample well, at least one elution reservoir, and at least one waste reservoir.

22. The cassette of claim 20, wherein at least one elution chamber further comprises an elution buffer composition.

23. The cassette of claim 22, wherein the elution buffer composition fills a volume of at least one elution chamber.

24. The cassette of claim 22, wherein the cassette further comprises a removable seal.

25. The cassette of claim 24, wherein the seal encloses at least one of an opening, a protrusion and a recess of the cover.

26. The cassette of claim 1, wherein at least one macrofluidic separation channel is optically-transparent.

27. The cassette of claim 26, wherein the separation channel is optically-transparent on at least one side.

28. The cassette of claim 26, wherein the separation channel is optically-transparent on only one side.

29. The cassette of claim 1, wherein the cassette comprises between 1 and 5 macrofluidic separation channels.

30. The cassette of claim 1, wherein the cassette comprises between 1 and 9 macrofluidic separation channels.

31. The cassette of claim 1, wherein the cassette comprises between 1 and 13 macrofluidic separation channels.

32. The cassette of claim 6, wherein the macrofluidic channel further comprises a lens positioned between the sample well cavity and the division point.

33. The cassette of claim 32, wherein said the lens comprises a gel matrix composition.

34. The cassette of claim 2, wherein the analyte-permeable barrier of the elution chamber comprises a hydrophilic membrane or filter.

35. The cassette of claim 34, wherein the analyte-permeable barrier comprises a least one pore having a diameter range of between 0.4 micron to 50 microns.

36. The cassette of claim 34, wherein the analyte-permeable barrier comprises a least one pore having a diameter range of between 0.4 micron to 1 micron.

37. The cassette of claim 1, wherein the analyte-impermeable barrier of the elution chamber is a membrane, filter, film, or any combination thereof.

38. The cassette of claim 37, wherein the analyte-impermeable barrier is an ultrafiltration membrane or a conductive film.

39. The cassette of claim 38, wherein the ultrafiltration membrane comprises a least one pore having a diameter range of between 0.001 micron to 0.1 micron.

40. The cassette of claim 38, wherein the ultrafiltration membrane has a molecular weight cutoff of between 1,000 to 30,000 daltons.

41. The cassette of claim 38, wherein the ultrafiltration membrane has a molecular weight cutoff of between 3,000 to 10,000 daltons.

42. The cassette of claim 38, wherein the analyte-impermeable barrier comprises a conductive film having the same charge as the analyte.

43. The cassette of claim 38, wherein the analyte-impermeable barrier comprises a conductive film contacted with negatively-charged sulfate groups.

44. The cassette of claim 38, wherein the analyte-impermeable barrier is Nafion.

45. A method of making an electrophoresis cassette, comprising:
providing an electrophoresis cassette of claim 1, wherein the cassette further comprises a buffer reservoir insert, a sample well insert, a waste reservoir insert, and a cover, wherein the buffer reservoir insert includes a vent, wherein the buffer reservoir insert traverses an opening in the cover plate aligned with the buffer reservoir, wherein the sample well insert traverses an opening in the cover plate aligned with the sample well cavity, wherein the waste reservoir insert includes an injection port, and wherein the waste reservoir insert traverses an opening in the cover plate aligned with the waste reservoir;
inserting a gel matrix composition through an injection port;
solidifying the gel matrix composition, wherein the gel matrix composition transforms from a liquid to a solid;
removing the buffer reservoir insert, sample well insert, and waste reservoir insert, wherein a sample well is generated;
filling the buffer reservoir, the elution reservoir, and the waste reservoir with a buffer composition;
filling the elution chamber with an elution buffer composition; and
sealing the electrophoresis cassette.

46. The method of claim 45, further comprising the steps of:
providing a casting fixture, wherein the fixture includes a front plate that contacts the top of the cassette, wherein the front plate comprises at least one opening that aligns with at least one of the vent of the buffer reservoir insert and the separation channel, and
a back plate that contacts the bottom of the cassette, wherein the back plate comprises at least one opening;
attaching the casting fixture to electrophoresis cassette, wherein the back plate contacts the bottom of the electrophoresis cassette and the front plate contacts the top of the electrophoresis cassette, and wherein the back and front plates are attached to each other;
wherein the casting fixture is provided and attached prior to the injecting step and,
detaching the casting fixture from the electrophoresis cassette prior to the removing step.

47. The method of claim 45, wherein the buffer reservoir insert fills a volume of the buffer reservoir.

48. The method of claim 45, wherein the sample well insert fills a volume of the sample well cavity.

49. The method of claim 45, wherein the waste reservoir insert fills a volume of the waste reservoir.

50. The method of claim 46, wherein the casting fixture is horizontal or vertical during the inserting and solidifying steps.

51. The method of claim 45, wherein the electrophoresis cassette comprises between 1 and 5 macrofluidic separation channels.

52. The method of claim 45, wherein the electrophoresis cassette comprises between 1 and 9 macrofluidic separation channels.

53. The method of claim 45, wherein the electrophoresis cassette comprises between 1 and 13 macrofluidic separation channels.

54. A detection system for detecting a property of an analyte within a sample comprising:
a cassette according to claim 1;
an electrode array comprising at least one of a negative electrode and a positive electrode, wherein the negative electrode aligns with a position on the cassette between the buffer reservoir and a corresponding end of the separation channel, and wherein the positive electrode aligns with a physically and electrically isolated portion of the separation channel;
a detector positioned near the separation channel of the electrophoresis cassette, wherein the detector detects a property of an analyte;
a processor configured to activate or deactivate power to at least one positive electrode based upon a signal received from the detector; and
a power module comprising at least one of a power supply and a relay to provide power to at least one of the processor, the negative electrode and at least one positive electrode.

55. The system of claim 54, wherein the property is an optical property of an analyte.

56. The system of claim 54, wherein the sample comprises a fluorescent compound and the analyte forms a complex with the fluorescent compound.

57. The system of claim 56, wherein the fluorescent compound is a fluorophore.

58. The system of claim 54, wherein the sample comprises a light-absorbing compound and the analyte forms a complex with the light-absorbing compound.

59. The system of claim 58, wherein the light-absorbing compound is a chromophore.

60. The system of claim 55, wherein the optical property is the emission of light.

61. The system of claim 55, wherein the optical property is the absorption of light.

62. The system of claim 54, wherein the analyte is a sample or a molecular weight marker.

63. The system of claim 62, wherein the detector detects a property of the molecular weight marker within a first macrofluidic channel and an sends a signal to the processor.

64. The system of claim 63, wherein the processor receives the signal from the detector and applies an algorithm to determine the molecular weight of at least one of an analyte at the division point of a second macrofluidic channel.

65. A method of fractionating analytes within a sample, comprising:
  providing an electrophoresis cassette of claim 1, wherein the cassette further comprises a buffer reservoir insert, a sample well insert, a waste reservoir insert, and a cover, wherein the buffer reservoir insert includes a vent, wherein the buffer reservoir insert traverses an opening in the cover plate aligned with the buffer reservoir, wherein the sample well insert traverses an opening in the cover plate aligned with the sample well cavity, wherein the waste reservoir insert includes an injection port, and wherein the waste reservoir insert traverses an opening in the cover plate aligned with the elution reservoir and the waste reservoirs;
  inserting a gel matrix composition through an injection port;
  solidifying the gel matrix composition, wherein the gel matrix composition transforms from a liquid to a solid;
  removing the buffer reservoir insert, sample well insert, and waste reservoir insert, wherein a sample well is generated;
  filling the buffer reservoir, the elution reservoir, and the waste reservoir with a buffer composition;
  filling the elution chamber with an elution buffer composition; and
  inserting the electrophoresis cassette into a detection system;
  programming the processor of the detection system to selectively activate the positive electrode of the electrode array aligned with the physically and electrically isolated portion of the separation channel comprising the elution chamber when the processor determines that at least one of an analyte of the desired molecular weight is traversing the division point of the separation channel;
  applying the sample to the sample well;
  applying a voltage across the electrophoresis cassette;
  collecting analytes of the sample having a desired electrophoretic mobility in the elution chamber,
  thereby fractionating analytes within a sample.

66. The method of claim 65, further comprising the steps of:
  providing a casting fixture, wherein the fixture includes a front plate that contacts the top of the cassette, wherein the front plate comprises at least one opening that aligns with at least one of the vent of the buffer reservoir insert and the separation channel, and a back plate that contacts the bottom of the cassette, wherein the back plate comprises at least one opening;
  attaching the casting fixture to electrophoresis cassette, wherein the back plate contacts the bottom of the electrophoresis cassette and the front plate contacts the top of the electrophoresis cassette, and wherein the back and front plates are attached to each other;
  wherein the casting fixture is provided and attached prior to the injecting step and,
  detaching the casting fixture from the electrophoresis cassette prior to the removing step.

67. The method of claim 65, wherein the sample comprises a detectable compound.

68. The method of claim 65, wherein the sample comprises at least one of a complex of an analyte and a fluorescent compound.

69. The method of claim 68, wherein the fluorescent compound is a fluorophore.

70. The method of claim 65, wherein the sample comprises at least one of a complex of an analyte and a light-absorbing compound.

71. The method of claim 70, wherein the light-absorbing compound is a chromophore.

72. The method of claim 65, wherein at least one of the gel matrix composition, the buffer composition, or the elution buffer composition comprises at least one of a fluorophore that complexes to at least one of an analyte.

73. The method of claim 65, wherein at least one of the gel matrix composition, the buffer composition, or the elution buffer composition comprises at least one of a chromophore that complexes to at least one of an analyte.

74. The method of claim 65, wherein the sample comprises a molecular weight marker.

75. The method of claim 65, wherein the processor of the detection system selectively activates the positive electrode of the electrode array aligned with the physically and electrically isolated portion of the separation channel comprising the elution chamber when an analyte having a specified electrophoretic mobility is detected and wherein the specified electrophoretic mobility is distinct for each macrofluidic channel.

76. The method of claim 65, wherein the analyte is a polynucleic acid or a polypeptide.

77. The method of claim 76, wherein the polynucleic acid comprises deoxyribonucleic acid (DNA) or ribonucleic acid (RNA).

78. The method of claim 76, wherein the polynucleic acid is double or single stranded.

79. The method of claim 76, wherein the polypeptide is native or denatured.

80. A device comprising an electrophoresis cassette, the electrophoresis cassette including:
  (a) a channel plate comprising a macrofluidic channel, wherein the macrofluidic channel comprises, from proximal to distal, a buffer reservoir, a first end of a separation channel, a sample well cavity, a constriction point, a division point, an elution chamber cavity, alternatively a combination of a second physically and electrically isolated end of the separation channel and an elution reservoir or a combination of a third physically and electrically isolated end of the separation channel and a waste reservoir;
  (b) an elution chamber comprising, from proximal to distal, an analyte-permeable barrier, a sample collection chamber having a sample removal port, and an analyte-impermeable barrier, wherein an elution module is attached to the elution chamber cavity;
  (c) a cover plate that contacts the top of the channel plate, wherein the cover plate comprises at least one of an opening, a protrusion, and a recess that align, from proximal to distal, with the buffer reservoir, the sample well cavity, the elution chamber, alternatively a combination of the second physically and electrically isolated end of the separation channel and the elution reservoir or a combination of the third physically and electrically isolated end of the separation channel and the waste reservoir;
(d) a gel matrix composition that fills the macrofluidic separation channel and defines a sample well within the sample well cavity;
(e) a liquid buffer composition that fills the buffer reservoir, the sample well, the elution reservoir or the waste reservoir;
(f) an elution buffer composition that fills the elution chamber; and
(g) a seal that encloses the electrophoresis cassette.

* * * * *

UNITED STATES PATENT AND TRADEMARK OFFICE
CERTIFICATE OF CORRECTION

PATENT NO. : 8,361,298 B2
APPLICATION NO. : 12/576148
DATED : January 29, 2013
INVENTOR(S) : Douglas G. Sabin et al.

It is certified that error appears in the above-identified patent and that said Letters Patent is hereby corrected as shown below:

In the Claims:

Claim 15, column 22, line 27, --and-- should be inserted before "a solid buffer composition."

Claim 16, column 22, line 29, --and-- should be inserted before "a solid buffer composition comprises at least one of a fluorophore or a chromophore."

Claim 65, column 25, at line 25, "reservoirs" should read --reservoir--

Signed and Sealed this
Eighteenth Day of June, 2013

Teresa Stanek Rea
*Acting Director of the United States Patent and Trademark Office*